(12) United States Patent
Burkart et al.

(10) Patent No.: US 12,172,988 B2
(45) Date of Patent: Dec. 24, 2024

(54) ANTICANCER AND ANTIFUNGAL SPLICE MODULATORS

(71) Applicant: The Regents of the University of California, Oakland, CA (US)

(72) Inventors: Michael D. Burkart, La Jolla, CA (US); Warren C. Chan, La Jolla, CA (US); James J. La Clair, La Jolla, CA (US); Kelsey A. Trieger, La Jolla, CA (US); Catriona Jamieson, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 21 days.

(21) Appl. No.: 17/574,100

(22) Filed: Jan. 12, 2022

(65) Prior Publication Data

US 2022/0227742 A1    Jul. 21, 2022

Related U.S. Application Data

(60) Provisional application No. 63/136,615, filed on Jan. 12, 2021.

(51) Int. Cl.
*C07D 407/12* (2006.01)
(52) U.S. Cl.
CPC .................................. *C07D 407/12* (2013.01)
(58) Field of Classification Search
CPC ..................................................... C07D 407/12
USPC ........................................................ 514/450
See application file for complete search history.

(56) References Cited

U.S. PATENT DOCUMENTS 9,604,973 B2 * 3/2017 Burkart ................ C07D 313/00

FOREIGN PATENT DOCUMENTS

WO    WO-2006060890 A1 *  6/2006  ........... B67D 1/0857

OTHER PUBLICATIONS

Chan, W.C. et al. (Dec. 23, 2020). "Scalable Synthesis of 17S-FD-895 Expands the Structural Understanding of Splice Modulatory Activity," *Cell Reports Physical Science* 1(12): 100277, with Supporting Information, 145 pages.
Chan, W.C. et al. (May 25, 2023, e-published May 8, 2023). "Stereochemical Control of Splice Modulation in FD-895 Analogues," *Journal of Medicinal Chemistry* 66(10):6577-6590.
Crews, L.A. et al. (Nov. 3, 2016, e-published Aug. 25, 2016). "RNA Splicing Modulation Selectively Impairs Leukemia Stem Cell Maintenance in Secondary Human AML," *Cell Stem Cell* 19(5):599-612.
Sim, J. et al. (Sep. 30, 2021). "Total Syntheses of Pladienolide-Derived Spliceosome Modulators," *Molecules* 26(19):5938.

* cited by examiner

*Primary Examiner* — Kahsay Habte
(74) *Attorney, Agent, or Firm* — Mintz, Levin, Cohn, Ferris, Glovsky and Popeo, P.C.

(57) ABSTRACT

Provided herein, inter alia, are splice modulator compounds. The compounds include optically pure, stereospecific analogs of FD-895. The methods provided herein allow, for example, for scalable preparation of said compounds, and further allow, for example, use of said compounds for inhibiting spliceosome activity.

12 Claims, 26 Drawing Sheets

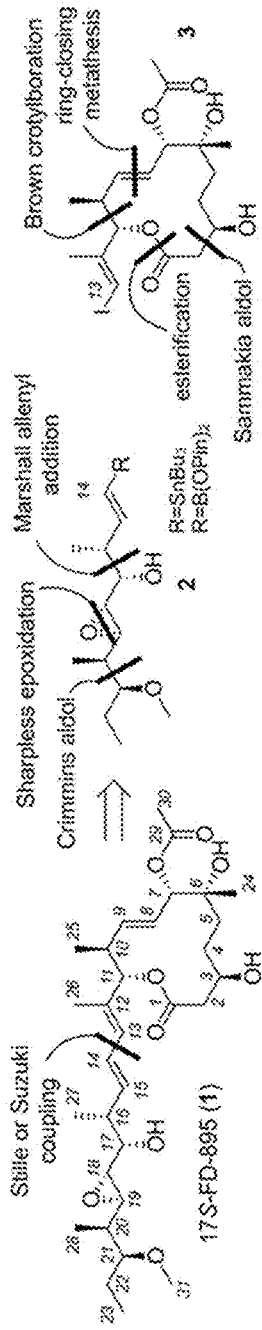
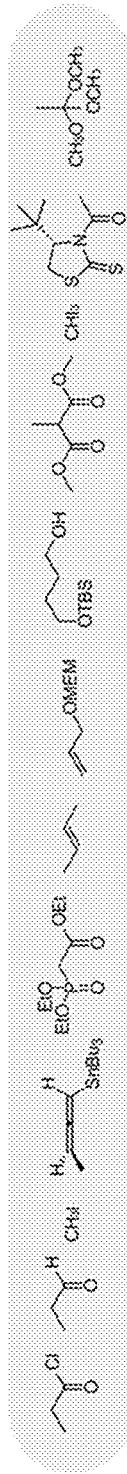
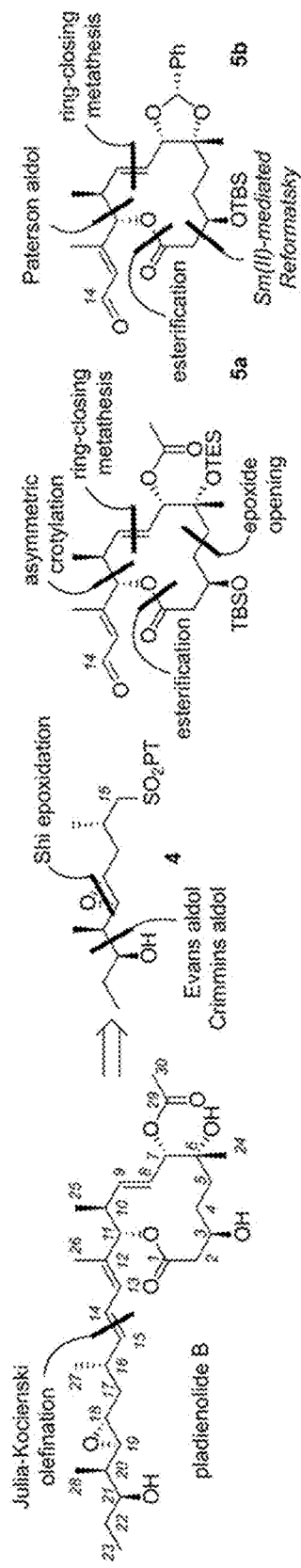
FIG. 1A
FIG. 1B

ANTICANCER AND ANTIFUNGAL SPLICE MODULATORS

CROSS REFERENCE TO RELATED APPLICATIONS

This application claims the benefit of U.S. Provisional application No. 63/136,615, filed Jan. 12, 2020, which is incorporated herein in its entirety and for all purposes.

BACKGROUND

While splice modulators have entered clinical trials, limited clinical efficacy in splicing factor mutation driven malignancies, such as acute myeloid leukemia, has remained a challenge. There is a pressing unmet medical need for developing potent small molecule splice modulators for the treatment of a broad array of malignancies characterized by splicing deregulation. However, the inability to practically access gram scale lead molecules with viable pharmacological properties continues to hinder their application. Disclosed herein, inter alia, are solutions to these and other problems in the art.

BRIEF SUMMARY OF THE INVENTION

Provided herein are, inter alia, splice modulator compounds. The compounds include optically pure, stereospecific non-natural analogs of FD-895, which are potent in vivo active splice modulators. The strategy described herein provides material to enable clinical translation, and further allows lead validation by expanding the structure-activity relationships that guide splice modulation.

In an aspect is provided a compound having a formula (I)

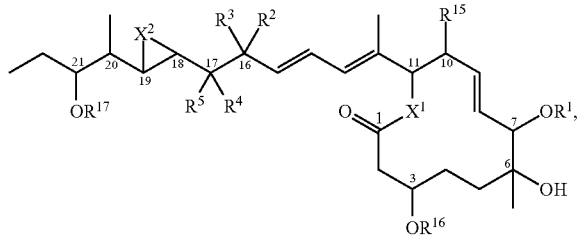

or a pharmaceutically acceptable salt thereof.

$X^1$ is —NH—, —O—, or $CH_2$. $X^2$ is —O— or —C($R^6$)($R^7$)—. $R^6$ and $R^7$ are independently hydrogen, halogen, substituted or unsubstituted alkyl, substituted or unsubstituted aryl, —$OR^{12}$, —OC(O)$R^{12}$, —OC(O)O$R^{12}$, or —OC(O)N$R^{13}R^{14}$. $R^1$, $R^{16}$ and $R^{17}$ are independently hydrogen, —C(O)$R^8$, or substituted or unsubstituted alkyl. $R^2$, $R^3$, $R^4$, and $R^5$ are independently hydrogen, substituted or unsubstituted alkyl, —$OR^9$, —OC(O)$R^9$, —OC(O)O$R^9$, or —OC(O)N$R^{10}R^{11}$. $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, or substituted or unsubstituted alkyl. In embodiments, the compound is optically pure; and
  i. the carbon at position 3 has an (S) stereochemistry;
  ii. the carbon at position 6 has an (S) stereochemistry;
  iii. the carbon at position 7 has an (R) stereochemistry;
  iv. the carbon at position 10 has an (R) stereochemistry;
  v. the carbon at position 11 has an (R) stereochemistry;
  vi. the carbon at position 18 has an (S) stereochemistry and the carbon at position 19 has an (S) stereochemistry;
  vii. the carbon at position 20 has (S) stereochemistry; and/or
  viii. the carbon at position 21 has (R) stereochemistry.

In another aspect is provided a pharmaceutical composition including the compound as described herein and a pharmaceutical excipient.

In another aspect is provided a method of treating cancer, and the method includes administering to a subject matter in need thereof a therapeutically effective amount the compound as described herein.

Other aspects are disclosed infra.

BRIEF DESCRIPTION OF THE DRAWINGS

FIGS. 1A and 1B show synthesis design of splice modulator compounds.

DETAILED DESCRIPTION

Definition

Figure 2:
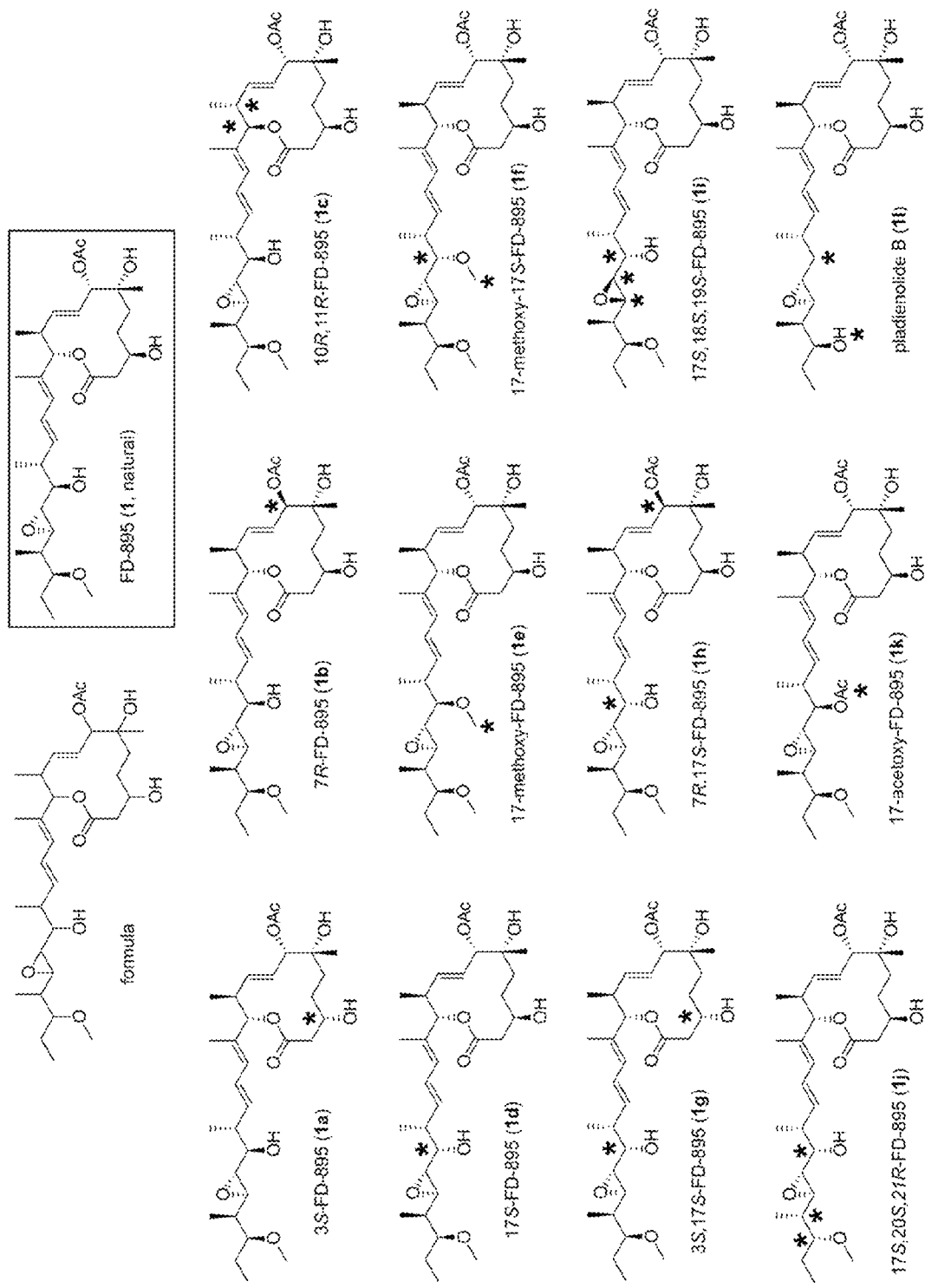
FIG. 2 shows various FD-895 diastereomers at several chiral centers (*).

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_5$O$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⁓" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

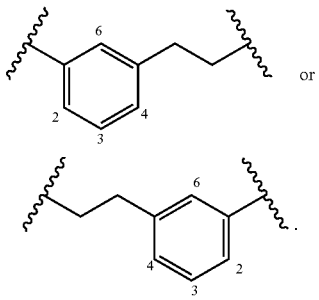

or

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$ NR'R", —NRSO$_2$R', —NR'NR"R'", —ONR'R", —NR'C(O) NR"NR'"R"", —CN, —NO$_2$, —NR'SO$_2$R", —NR'C(O)R", —NR'C(O)—OR", —NR'OR", in a number ranging from zero to (2 m'+1), where m' is the total number of carbon atoms in such radical. R, R', R", R'", and R'" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$ NR'R", —NRSO$_2$R', —NR'NR"R'", —ONR'R", —NR'C(O) NR"NR'"R"", —CN, —NO$_2$, —R', —N$_3$, —CH(Ph)$_2$, fluoro (C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkyl ene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "optically pure" refers to the presence of non-racemic configuration of a compound, and the compound has a predominant form of one specific stereoisomeric configuration (e.g., R or S) at one or more stereoisomeric (chiral) centers. In certain embodiments, the term "optically pure" means sufficiently homogeneous, predominant stereoisomeric configuration of a compound, so the "optically pure" compound appears free of readily detectable impurities (i.e. compound having non-predominant stereoisomeric configuration), which can be determined by standard analytical methods, such as thin layer chromatography (TLC), gel electrophoresis, high performance liquid chromatography (HPLC), nuclear magnetic resonance (NMR), and mass spectrometry (MS). In certain embodiments, when the compound is "optically pure" at least about 95 weight %, at least about 96 weight %, at least about 97 weight %, at least about 98 weight %, at least about 99 weight %, or at least about 99.5 weight % based on total weight of the compound of one stereoisomeric configuration predominates.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$), etc., wherein each of $R^{13.A}$, $R^{13.B}$, $R^{13.C}$, $R^{13.D}$, etc. is defined within the scope of the definition of $R^{13}$ and optionally differently.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$cu, $^{64}$cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lb, $^{177}$Lb, $^{186}$Re, $^{188}$Re, $^{189}$Re, $^{194}$Ir, $^{198}$Ab, $^{199}$Ab, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("US-PIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99}$Tc, $^{99}$Mo, $^{105}$Pd, $^{105}$Rb, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. Non-limiting examples of coupling reagents include benzotriazol-1-yl-oxytripyrrolidinophosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-tris-pyrrolidinophosphonium hexafluorophosphate (PyClock), 1-[Bis(dimethylamino)methylene]-1H-1,2,3-triazolo[4,5-b]pyridinium 3-oxid hexafluorophosphate (HATU), or 2-(1H-benzotriazol-1-yl)-1,1,3,3-tetramethyluronium hexafluorophosphate (HBTU).

The term "solution" is used in accor and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "associated" or "associated with" in the context of a substance or substance activity or function associated with a disease (e.g. infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g. compound as described herein) effective as an antibiotic.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, metastatic bone cancer, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "lymphoma" refers broadly to a group of blood cell tumors that develop from cells of the immune system found in lymph, i.e. lymphocytes (e.g. natural killer cells (NK cells), T cells, and B cells). Lymphoma is typically classified into Hodgkin's lymphomas (HL) and the non-Hodgkin lymphomas (NHL) or based on whether it develops in B-lymphocytes (B-cells) or T-lymphocytes (T-cells). Exemplary lymphomas (Hodgkin's lymphomas and non-Hodgkin's lymphomas) that may be treated with a compound or method provided herein include, for example, nodular-sclerosis classical Hodgkin lymphoma, mixed cellularity classical Hodgkin lymphoma, lymphocyte-rich classical Hodgkin lymphoma, lymphocyte-depleted classical Hodgkin lymphoma, aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, and acute lymphoblastic lymphoma.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "DNA" and "RNA" refer to deoxyribonucleic acid and ribonucleic acid, respectively.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products in real time.

The terms "spliceosome" or "spliceosomal" are used according to their common and ordinary meaning and refer to the component or complex in a cell involved in removal of introns from transcribed pre-mRNA. A spliceosome may include a complex of small nuclear RNA (snRNA) and protein subunits.

The term "splicing" is used according to its common and ordinary meaning and refer to a process in a cell involved in removal of introns from transcribed pre-mRNA. During the splicing, the removal of introns and joining of exons from nascent pre-mRNA occur simultaneously or sequentially. Splicing plays an important role in human biology and its relevance in developing and proliferation of cancer cells.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a particular protein or nucleic acid target. In some embodiment, inhibition of the invention refers to an inhibition upon a splicing process in a cell, preferably in a cancer cell, using an inhibitor (e.g., antagonist, antibodies, RNAi molecules or small molecules). Thus, inhibition includes, at least in part, partially or totally blocking stimulation, decreasing, preventing, or delaying activation, or inactivating, desensitizing, or down-regulating signal transduction or enzymatic activity or the amount of a protein or protein complex (e.g. spliceosome).

A "test compound" as used herein refers to an experimental compound as described herein that can be used in a screening process to identify activity, non-activity, or other modulation of a particularized biological target or pathway.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, "biomolecule" is used in its customary sense and refers to a molecule found in nature or derivatives thereof, including macromolecules such as proteins, carbohydrates, lipids, and nucleic acids, as well as small molecules such as primary metabolites, secondary metabolites, and natural products. A biomolecule may be present as a moiety attached to the remainder of a compound. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Compounds

Provided herein are novel compounds of FD-895 of diastereomers. In embodiments, the compounds are useful as in vivo active splice modulator. In embodiments, the compounds are useful as comparator compounds to identify (e.g. for comparing the activity of analogs as set forth in the Examples section below). The strategy described herein provides, for example, material to enable clinical translation, and further allows lead validation by expanding the structure-activity relationships that guide splice modulation.

In an aspect, provided is a compound having the formula

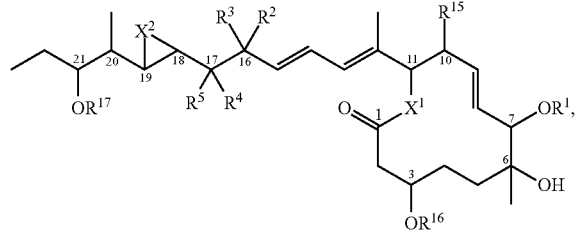

(I)

or a pharmaceutically acceptable salt thereof.

$X^1$ is —NH—, —O—, or $CH_2$. $X^2$ is —O— or —C($R^6$)($R^7$)—. $R^6$ and $R^7$ are independently hydrogen, halogen, substituted or unsubstituted alkyl, substituted or unsubstituted aryl, —$OR^{12}$, —$OC(O)R^{12}$, —$OC(O)OR^{12}$, or —$OC(O)NR^{13}R^{14}$. $R^1$, $R^{16}$, and $R^{17}$ are independently hydrogen, —$C(O)R^8$, or substituted or unsubstituted alkyl. $R^2$, $R^3$, $R^4$, and $R^5$ are independently hydrogen, substituted or unsubstituted alkyl, —$OR^9$, —$OC(O)R^9$, —$OC(O)OR^9$, or —$OC(O)NR^{10}R^{11}$. $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, or substituted or unsubstituted alkyl.

In embodiments, the compound is an optically pure; and
i. the carbon at position 3 has an (S) stereochemistry;
ii. the carbon at position 6 has an (S) stereochemistry;
iii. the carbon at position 7 has an (R) stereochemistry;
iv. the carbon at position 10 has an (R) stereochemistry;
v. the carbon at position 11 has an (R) stereochemistry;
vi. the carbon at position 18 has an (S) stereochemistry and the carbon at position 19 has an (S) stereochemistry;
vii. the carbon at position 20 has (S) stereochemistry; and/or
viii. the carbon at position 21 has (R) stereochemistry.

In embodiments, the carbon at position 17 has (S) stereochemistry. In embodiments, the carbon at position 3 has (S) stereochemistry and the carbon at position 17 has (S) stereochemistry. In embodiments, the carbon at position 6 has (S) stereochemistry and the carbon at position 17 having (S) stereochemistry. In embodiments, the carbon at position 7 has (R) stereochemistry and the carbon at position 17 has (S) stereochemistry. In embodiments, the carbon at 10 position has (R) stereochemistry and the carbon at 17 position has (S) stereochemistry. In embodiments, the carbon at position 11 has (R) stereochemistry and the carbon at position 17 has (S) stereochemistry. In embodiments, the carbon at position 10 has (R) stereochemistry, the carbon at position 11 has (R) stereochemistry and the carbon at position 17 has (S) stereochemistry. In embodiments, the carbon at position 18 has (S) stereochemistry, the carbon at position 19 has (S) stereochemistry, and the carbon at position 17 having (S) stereochemistry. In embodiments, the carbon at position 20 has (S) stereochemistry and the carbon at position 17 has (S) stereochemistry. In embodiments, the carbon at position 21 has (R) stereochemistry and the carbon at position 17 has (S) stereochemistry. In embodiments, the carbon at 20 position has (S) stereochemistry, the carbon at 21 position has (R) stereochemistry and the carbon at 17 position has (S) stereochemistry.

In embodiments, $X^1$ is —NH—. In embodiments, $X^1$ is —O—. In embodiments, $X^1$ is —$CH_2$—. In embodiments, $X^2$ is —O—. In embodiments, $X^2$ is —C($R^6$)($R^7$)—. In embodiments, $X^1$ is —O— and $X^2$ is —O—.

In embodiments, $R^2$ is hydrogen. In embodiments, $R^2$ is substituted or unsubstituted $C_1$-$C_4$ alkyl. In embodiments, $R^2$ is substituted $C_1$-$C_4$ alkyl. In embodiments, $R^2$ is unsubstituted $C_1$-$C_4$ alkyl. In embodiments, $R^2$ is methyl. In embodiments, $R^2$ is ethyl. In embodiments, $R^2$ is propyl. In embodiments, $R^2$ is isopropyl. In embodiments, $R^2$ is butyl. In embodiments, $R^2$ is t-butyl.

In embodiments, $R^2$ is —$OR^9$. In embodiments, $R^2$ is —$OC(O)R^9$. In embodiments, $R^2$ is —$OC(O)OR^9$. In embodiments, $R^9$ is hydrogen. In embodiments, $R^9$ is unsubstituted $C_1$-$C_4$ alkyl. In embodiments, $R^9$ is methyl. In embodiments, $R^9$ is ethyl. In embodiments, $R^9$ is propyl. In embodiments, $R^9$ is isopropyl. In embodiments, $R^9$ is butyl. In embodiments, $R^9$ is t-butyl. In embodiments, $R^2$ is —OH. In embodiments, $R^2$ is —$OCH_3$. In embodiments, $R^2$ is —$OC(O)CH_3$.

In embodiments, $R^2$ is —$OC(O)NR^{10}R^{11}$. In embodiments, $R^{10}$ is hydrogen. In embodiments, $R^{10}$ is unsubstituted $C_1$-$C_4$ alkyl. In embodiments, $R^{10}$ is methyl. In embodiments, $R^{10}$ is ethyl. In embodiments, $R^{10}$ is propyl. In embodiments, $R^{10}$ is isopropyl. In embodiments, $R^{10}$ is butyl. In embodiments, $R^{10}$ is t-butyl. In embodiments, $R^{11}$ is hydrogen. In embodiments, $R^{11}$ is unsubstituted $C_1$-$C_4$ alkyl. In embodiments, $R^{11}$ is methyl. In embodiments, $R^{11}$ is ethyl. In embodiments, $R^{11}$ is propyl. In embodiments, $R^{11}$ is isopropyl. In embodiments, $R^{11}$ is butyl. In embodiments, $R^{11}$ is t-butyl. In embodiments, $R^2$ is —$OC(O)NH_2$. In embodiments, $R^2$ is —$OC(O)NHCH_3$.

In embodiments, $R^3$ is hydrogen. In embodiments, $R^3$ is substituted or unsubstituted $C_1$-$C_4$ alkyl. In embodiments, $R^3$ is substituted $C_1$-$C_4$ alkyl. In embodiments, $R^3$ is unsubstituted $C_1$-$C_4$ alkyl. In embodiments, $R^3$ is methyl. In embodiments, $R^3$ is ethyl. In embodiments, $R^3$ is propyl. In embodiments, $R^3$ is isopropyl. In embodiments, $R^3$ is butyl. In embodiments, $R^3$ is t-butyl.

In embodiments, $R^3$ is —$OR^9$. In embodiments, $R^3$ is —$OC(O)R^9$. In embodiments, $R^3$ is —$OC(O)OR^9$. In embodiments, $R^9$ is hydrogen. In embodiments, $R^9$ is unsubstituted $C_1$-$C_4$ alkyl. In embodiments, $R^9$ is methyl. In embodiments, $R^9$ is ethyl. In embodiments, $R^9$ is propyl. In embodiments, $R^9$ is isopropyl. In embodiments, $R^9$ is butyl. In embodiments, $R^9$ is t-butyl. In embodiments, $R^3$ is —OH. In embodiments, $R^3$ is —$OCH_3$. In embodiments, $R^3$ is —$OC(O)CH_3$.

In embodiments, $R^3$ is —$OC(O)NR^{10}R^{11}$. In embodiments, $R^{10}$ is hydrogen. In embodiments, $R^{10}$ is unsubstituted $C_1$-$C_4$ alkyl. In embodiments, $R^{10}$ is methyl. In embodiments, $R^{10}$ is ethyl. In embodiments, $R^{10}$ is propyl. In embodiments, $R^{10}$ is isopropyl. In embodiments, $R^{10}$ is butyl. In embodiments, $R^{10}$ is t-butyl. In embodiments, $R^{11}$ is hydrogen. In embodiments, $R^{11}$ is unsubstituted $C_1$-$C_4$ alkyl. In embodiments, $R^{11}$ is methyl. In embodiments, $R^{11}$ is ethyl. In embodiments, $R^{11}$ is propyl. In embodiments, $R^{11}$ is isopropyl. In embodiments, $R^{11}$ is butyl. In embodiments, $R^{11}$ is t-butyl. In embodiments, $R^3$ is —$OC(O)NH_2$. In embodiments, $R^3$ is —$OC(O)NHCH_3$.

In embodiments, $R^4$ is hydrogen. In embodiments, $R^4$ is substituted or unsubstituted $C_1$-$C_4$ alkyl. In embodiments, $R^4$ is substituted $C_1$-$C_4$ alkyl. In embodiments, $R^4$ is unsubstituted $C_1$-$C_4$ alkyl. In embodiments, $R^4$ is methyl. In embodiments, $R^4$ is ethyl. In embodiments, $R^4$ is propyl. In embodiments, $R^4$ is isopropyl. In embodiments, $R^4$ is butyl. In embodiments, $R^4$ is t-butyl. In embodiments, $R^4$ is —$OR^9$. In embodiments, $R^4$ is —$OC(O)R^9$. In embodiments, $R^4$ is —$OC(O)OR^9$. In embodiments, $R^9$ is hydrogen. In embodiments, $R^9$ is unsubstituted $C_1$-$C_4$ alkyl. In embodiments, $R^9$ is methyl. In embodiments, $R^9$ is ethyl. In embodiments, $R^9$ is propyl. In embodiments, $R^9$ is isopropyl. In embodiments, $R^9$ is butyl. In embodiments, $R^9$ is t-butyl. In embodiments, $R^4$ is —OH. In embodiments, $R^4$ is —$OCH_3$. In embodiments, $R^4$ is —$OC(O)CH_3$.

In embodiments, $R^4$ is —$OC(O)NR^{10}R^{11}$. In embodiments, $R^{10}$ is hydrogen. In embodiments, $R^{10}$ is unsubstituted $C_1$-$C_4$ alkyl. In embodiments, $R^{10}$ is methyl. In embodiments, $R^{10}$ is ethyl. In embodiments, $R^{10}$ is propyl. In embodiments, $R^{10}$ is isopropyl. In embodiments, $R^{10}$ is butyl. In embodiments, $R^{10}$ is t-butyl. In embodiments, $R^{11}$ is hydrogen. In embodiments, $R^{11}$ is unsubstituted $C_1$-$C_4$ alkyl. In embodiments, $R^{11}$ is methyl. In embodiments, $R^{11}$ is ethyl. In embodiments, $R^{11}$ is propyl. In embodiments, $R^{11}$ is isopropyl. In embodiments, $R^{11}$ is butyl. In embodiments, $R^{11}$ is t-butyl. In embodiments, $R^4$ is —$OC(O)NH_2$. In embodiments, $R^4$ is —$OC(O)NHCH_3$.

In embodiments, $R^5$ is hydrogen. In embodiments, $R^5$ is substituted or unsubstituted $C_1$-$C_4$ alkyl. In embodiments, $R^5$ is substituted $C_1$-$C_4$ alkyl. In embodiments, $R^5$ is unsubstituted $C_1$-$C_4$ alkyl. In embodiments, $R^5$ is methyl. In embodiments, $R^5$ is ethyl. In embodiments, $R^5$ is propyl. In embodiments, $R^5$ is isopropyl. In embodiments, $R^5$ is butyl. In embodiments, $R^5$ is t-butyl.

In embodiments, $R^5$ is —$OR^9$. In embodiments, $R^5$ is —$OC(O)R^9$. In embodiments, $R^5$ is —$OC(O)OR^9$. In embodiments, $R^9$ is hydrogen. In embodiments, $R^9$ is unsubstituted $C_1$-$C_4$ alkyl. In embodiments, $R^9$ is methyl. In embodiments, $R^9$ is ethyl. In embodiments, $R^9$ is propyl. In embodiments, $R^9$ is isopropyl. In embodiments, $R^9$ is butyl. In embodiments, $R^9$ is t-butyl. In embodiments, $R^5$ is —OH. In embodiments, $R^5$ is —$OCH_3$. In embodiments, $R^5$ is —$OC(O)CH_3$.

In embodiments, $R^5$ is —$OC(O)NR^{10}R^{11}$. In embodiments, $R^{10}$ is hydrogen. In embodiments, $R^{10}$ is unsubstituted $C_1$-$C_4$ alkyl. In embodiments, $R^{10}$ is methyl. In embodiments, $R^{10}$ is ethyl. In embodiments, $R^{10}$ is propyl. In embodiments, $R^{10}$ is isopropyl. In embodiments, $R^{10}$ is butyl. In embodiments, $R^{10}$ is t-butyl. In embodiments, $R^{11}$ is hydrogen. In embodiments, $R^{11}$ is unsubstituted $C_1$-$C_4$ alkyl. In embodiments, $R^{11}$ is methyl. In embodiments, $R^{11}$ is ethyl. In embodiments, $R^{11}$ is propyl. In embodiments, $R^{11}$ is isopropyl. In embodiments, $R^{11}$ is butyl. In embodiments, $R^{11}$ is t-butyl. In embodiments, $R^5$ is —$OC(O)NH_2$. In embodiments, $R^5$ is —$OC(O)NHCH_3$.

In embodiments, one of $R^2$ and $R^3$ is hydrogen and the other one of $R^2$ and $R^3$ is not hydrogen. In embodiments, $R^2$ is hydrogen and $R^3$ is substituted or unsubstituted alkyl, —$OR^9$, —$OC(O)R^9$, —$OC(O)OR^9$, or —$OC(O)NR^{10}R^{11}$. In embodiments, $R^2$ is hydrogen and $R^3$ is substituted or unsubstituted $C_1$-$C_4$ alkyl. In embodiments, $R^2$ is hydrogen and $R^3$ is unsubstituted $C_1$-$C_4$ alkyl. In embodiments, $R^2$ is hydrogen and $R^3$ is —$CH_3$ or —$CH_2CH_3$. In embodiments, $R^2$ is hydrogen and $R^3$ is —$CH_3$.

In embodiments, $R^3$ is hydrogen and $R^2$ is substituted or unsubstituted alkyl, —$OR^9$, —$OC(O)R^9$, —$OC(O)OR^9$, or —$OC(O)NR^{10}R^{11}$. In embodiments, $R^3$ is hydrogen and $R^2$ is substituted or unsubstituted $C_1$-$C_4$ alkyl. In embodiments, $R^3$ is hydrogen and $R^2$ is unsubstituted $C_1$-$C_4$ alkyl. In embodiments, $R^3$ is hydrogen and $R^2$ is —$CH_3$ or —$CH_2CH_3$. In embodiments, $R^3$ is hydrogen and $R^2$ is —$CH_3$.

In embodiments, the chiral carbon 16 where $R^2$ and $R^3$ are attached has (S) stereochemistry. In embodiments, the chiral carbon 16 where $R^2$ and $R^3$ are attached has (R) stereochemistry.

In embodiments, one of $R^4$ and $R^5$ is hydrogen and the other one of $R^4$ and $R^5$ is not hydrogen. In embodiments, $R^4$ is hydrogen and $R^5$ is substituted or unsubstituted alkyl, —$OR^9$, —$OC(O)R^9$, —$OC(O)OR^9$, or —$OC(O)NR^{10}R^{11}$. In embodiments, $R^4$ is hydrogen and $R^5$ is substituted or unsubstituted $C_1$-$C_4$ alkyl. In embodiments, $R^4$ is hydrogen and $R^5$ is unsubstituted $C_1$-$C_4$ alkyl. In embodiments, $R^4$ is hydrogen and $R^5$ is —$CH_3$ or —$CH_2CH_3$. In embodiments, $R^4$ is hydrogen and $R^5$ is —$CH_3$.

In embodiments, $R^5$ is hydrogen and $R^4$ is substituted or unsubstituted alkyl, —$OR^9$, —$OC(O)R^9$, —$OC(O)OR^9$, or —$OC(O)NR^{10}R^{11}$. In embodiments, $R^5$ is hydrogen and $R^4$ is substituted or unsubstituted $C_1$-$C_4$ alkyl. In embodiments, $R^5$ is hydrogen and $R^4$ is unsubstituted $C_1$-$C_4$ alkyl. In embodiments, $R^5$ is hydrogen and $R^4$ is —$CH_3$ or —$CH_2CH_3$. In embodiments, $R^5$ is hydrogen and $R^4$ is —$CH_3$.

In embodiments, the chiral carbon 17 where $R^4$ and $R^5$ are attached has (S) stereochemistry. In embodiments, the chiral carbon 17 where $R^4$ and $R^5$ are attached has (R) stereochemistry.

In embodiments, $R^2$ is hydrogen, and $R^4$ is hydrogen.

In embodiments, the carbon at position 3 has (S) stereochemistry. In embodiments, the compound has the formula (II-a), (II-a)

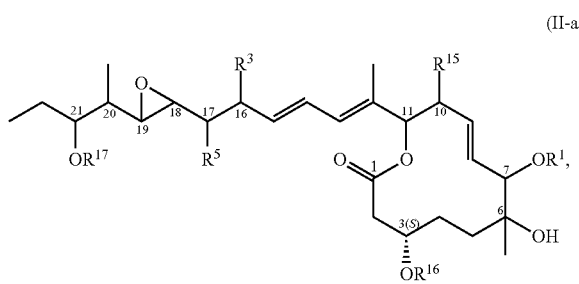

or a pharmaceutically acceptable salt thereof. $R^1$, $R^3$, $R^5$, $R^{15}$, $R^{16}$, and $R^{17}$ are as described above.

In embodiments, the carbon at position 6 has (S) stereochemistry. In embodiments, the compound has the formula (II-b), (II-b)

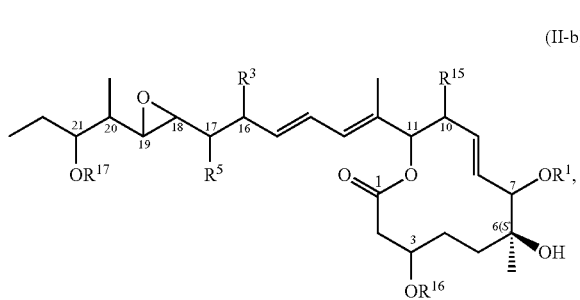

or a pharmaceutically acceptable salt thereof. $R^1$, $R^3$, $R^5$, $R^{15}$, $R^{16}$, and $R^{17}$ are as described above.

In embodiments, the carbon at position 7 has (R) stereochemistry. In embodiments, the compound has the formula (II-c), (II-c)

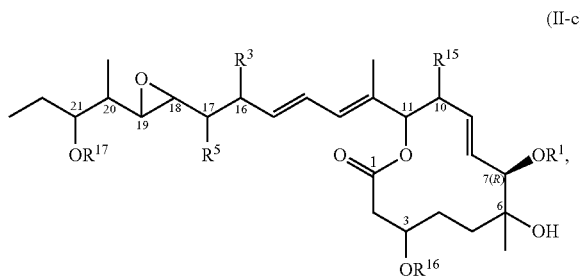

or a pharmaceutically acceptable salt thereof. $R^1$, $R^3$, $R^5$, $R^{15}$, $R^{16}$, and $R^{17}$ are as described above.

In embodiments, the carbon at position 10 has (R) stereochemistry. In embodiments, the compound has the formula (II-d), (II-d)

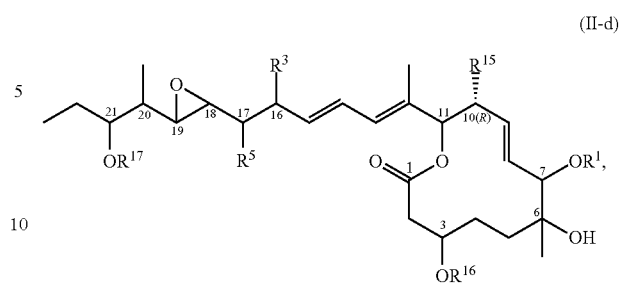

or a pharmaceutically acceptable salt thereof. $R^1$, $R^3$, $R^5$, $R^{15}$, $R^{16}$, and $R^{17}$ are as described above.

In embodiments, the carbon at position 11 has (R) stereochemistry. In embodiments, the compound has the formula (II-e), (II-e)

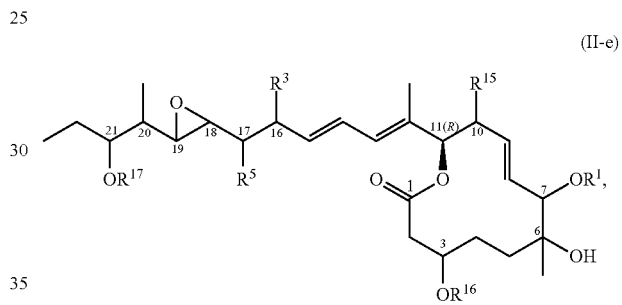

or a pharmaceutically acceptable salt thereof. $R^1$, $R^3$, $R^5$, $R^{15}$, $R^{16}$, and $R^{17}$ are as described above.

In embodiments, the c carbon at position 18 has (S) stereochemistry and the carbon at position 19 having (S) stereochemistry. In embodiments, the compound has the formula (II-f), (II-f)

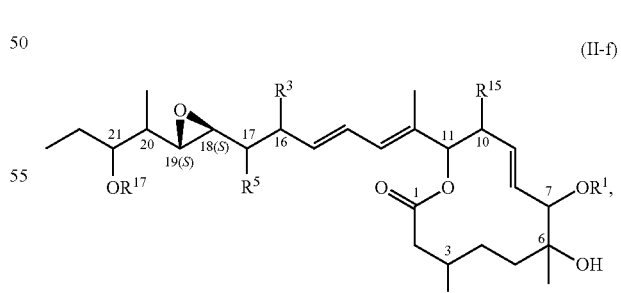

or a pharmaceutically acceptable salt thereof. $R^1$, $R^3$, $R^5$, $R^{15}$, $R^{16}$, and $R^{17}$ are as described above.

In embodiments, the carbon at position 20 has (S) stereochemistry. In embodiments, the compound has the formula (II-g),

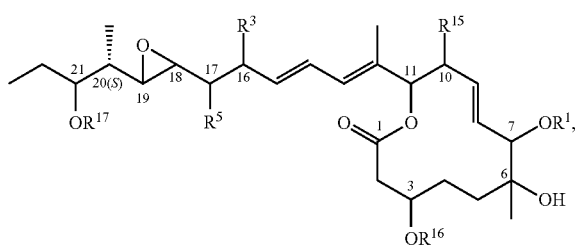

(II-g)

or a pharmaceutically acceptable salt thereof. $R^1$, $R^3$, $R^5$, $R^{15}$, $R^{16}$, and $R^{17}$ are as described above.

In embodiments, the carbon at position 21 has (R) stereochemistry. In embodiments, the compound has the formula (II-h),

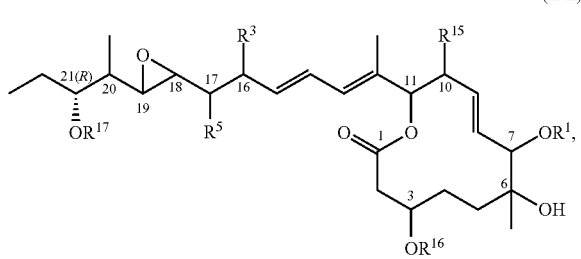

(II-h)

or a pharmaceutically acceptable salt thereof. $R^1$, $R^3$, $R^5$, $R^{15}$, $R^{16}$, and $R^{17}$ are as described above.

In embodiments, $R^{15}$ is hydrogen or $C_1$-$C_4$ unsubstituted alkyl. In embodiments, $R^{15}$ is hydrogen. In embodiments, $R^{15}$ is $C_1$-$C_4$ unsubstituted alkyl. In embodiments, $R^{15}$ is methyl. In embodiments, $R^{15}$ is ethyl. In embodiments, $R^{15}$ is propyl. In embodiments, $R^{15}$ is isopropyl. In embodiments, $R^{15}$ is butyl. In embodiments, $R^{15}$ is t-butyl.

In embodiments, $R^3$ is hydrogen or $C_1$-$C_4$ unsubstituted alkyl. In embodiments, $R^3$ is hydrogen. In embodiments, $R^3$ is $C_1$-$C_4$ unsubstituted alkyl. In embodiments, $R^3$ is methyl. In embodiments, $R^3$ is ethyl. In embodiments, $R^3$ is propyl. In embodiments, $R^3$ is isopropyl. In embodiments, $R^3$ is butyl. In embodiments, $R^3$ is t-butyl.

In embodiments, $R^5$ is —$OR^9$. In embodiments, $R^5$ is —$OC(O)R^9$. In embodiments, $R^9$ is hydrogen or $C_1$-$C_4$ unsubstituted alkyl. In embodiments, $R^9$ is hydrogen or methyl. In embodiments, $R^9$ is hydrogen. In embodiments, $R^9$ is $C_1$-$C_4$ unsubstituted alkyl. In embodiments, $R^9$ is methyl. In embodiments, $R^9$ is ethyl. In embodiments, $R^9$ is propyl. In embodiments, $R^9$ is isopropyl. In embodiments, $R^9$ is butyl. In embodiments, $R^9$ is t-butyl. In embodiments, $R^5$ is —OH. In embodiments, $R^5$ is —$OCH_3$. In embodiments, $R^5$ is —$OC(O)CH_3$. In embodiments, $R^5$ is —$OC(O)CH_2CH_3$.

In embodiments, $R^1$ is hydrogen. In embodiments, $R^1$ is —$C(O)R^8$. In embodiments, $R^8$ is $C_1$-$C_4$ unsubstituted alkyl. In embodiments, $R^8$ is methyl. In embodiments, $R^8$ is ethyl. In embodiments, $R^8$ is propyl. In embodiments, $R^8$ is isopropyl. In embodiments, $R^8$ is butyl. In embodiments, $R^8$ is t-butyl.

In embodiments, $R^{16}$ is hydrogen or $C_1$-$C_4$ unsubstituted alkyl. In embodiments, $R^{16}$ is hydrogen. In embodiments, $R^{16}$ is $C_1$-$C_4$ unsubstituted alkyl. In embodiments, $R^{16}$ is methyl. In embodiments, $R^{16}$ is ethyl. In embodiments, $R^{16}$ is propyl. In embodiments, $R^{16}$ is isopropyl. In embodiments, $R^{16}$ is butyl. In embodiments, $R^{16}$ is t-butyl.

In embodiments, $R^{17}$ is hydrogen or $C_1$-$C_4$ unsubstituted alkyl. In embodiments, $R^{17}$ is hydrogen. In embodiments, $R^{17}$ is $C_1$-$C_4$ unsubstituted alkyl. In embodiments, $R^{17}$ is methyl. In embodiments, $R^{17}$ is ethyl. In embodiments, $R^{17}$ is propyl. In embodiments, $R^{17}$ is isopropyl. In embodiments, $R^{17}$ is butyl. In embodiments, $R^{17}$ is t-butyl.

In embodiments, the compound is

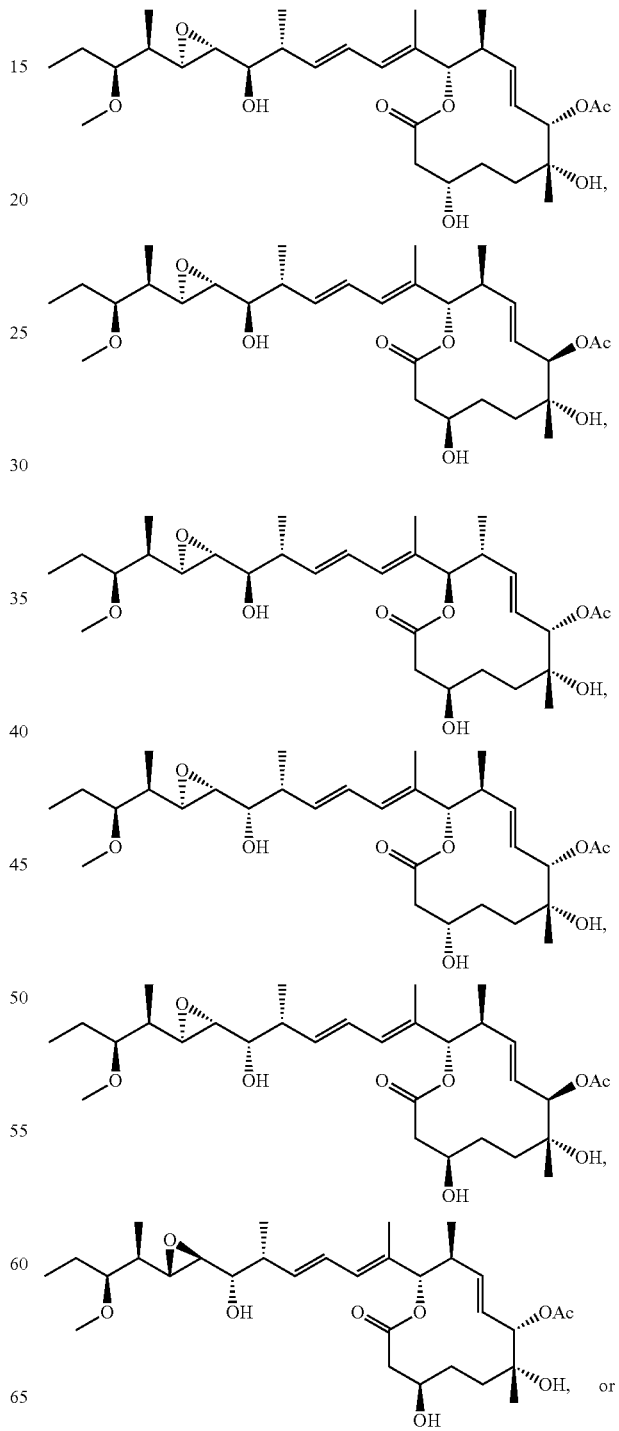

-continued

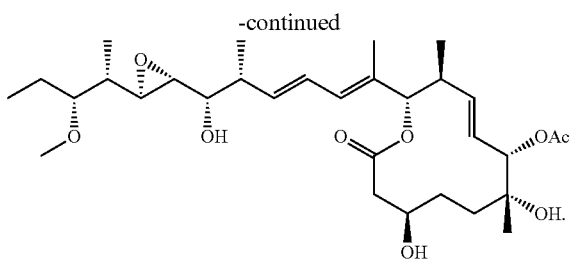

In embodiments, the compound is

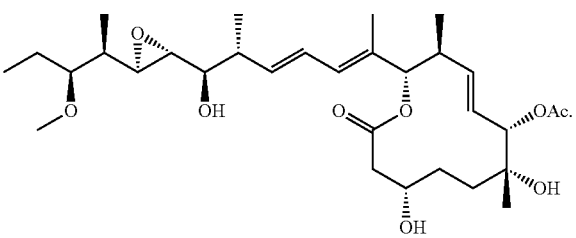 [SMILES: CC[C@H](OC)[C@@H](C)[C@H]1O[C@@H]1[C@H](O)[C@H](C)/C=C/C=C(\C)[C@H]1OC(=O)C[C@@H](O)CC[C@@](C)(O)[C@@H](OC(C)=O)/C=C/[C@@H]1C]

In embodiments, the compound is

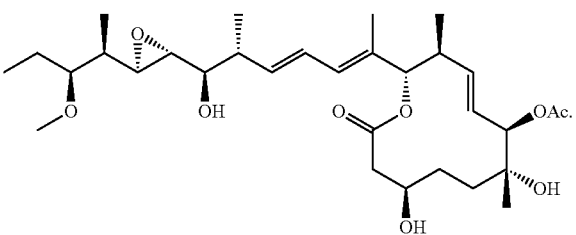 [SMILES: CC[C@H](OC)[C@@H](C)[C@H]1O[C@@H]1[C@H](O)[C@H](C)/C=C/C=C(\C)[C@H]1OC(=O)C[C@H](O)CC[C@@](C)(O)[C@H](OC(C)=O)/C=C/[C@@H]1C]

In embodiments, the compound is

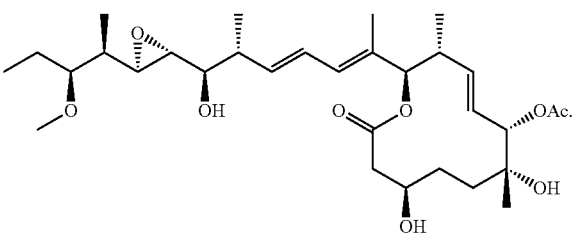 [SMILES: CC[C@H](OC)[C@@H](C)[C@H]1O[C@@H]1[C@H](O)[C@H](C)/C=C/C=C(\C)[C@@H]1OC(=O)C[C@H](O)CC[C@@](C)(O)[C@@H](OC(C)=O)/C=C/[C@H]1C]

In embodiments, the compound is

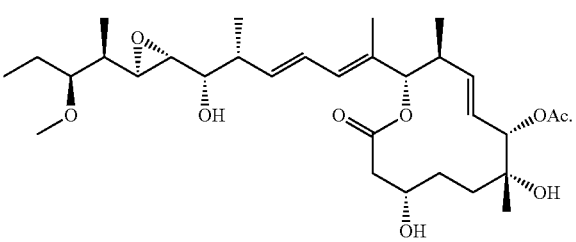 [SMILES: CC[C@H](OC)[C@@H](C)[C@H]1O[C@@H]1[C@@H](O)[C@H](C)/C=C/C=C(\C)[C@H]1OC(=O)C[C@@H](O)CC[C@@](C)(O)[C@@H](OC(C)=O)/C=C/[C@@H]1C]

In embodiments, the compound is

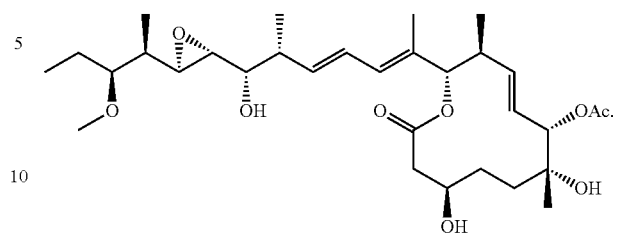

In embodiments, the compound is

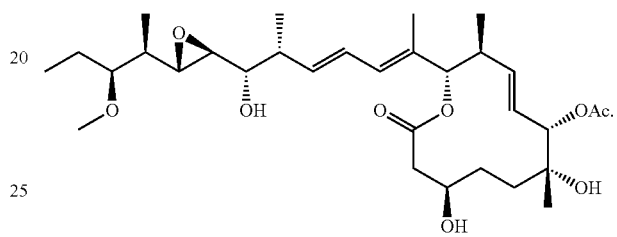

In embodiments, the compound is

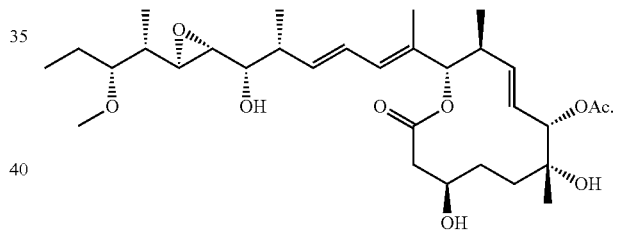

In embodiments, the carbon at position 3 has (S) stereochemistry. In embodiments, the compound has the formula (III-a),

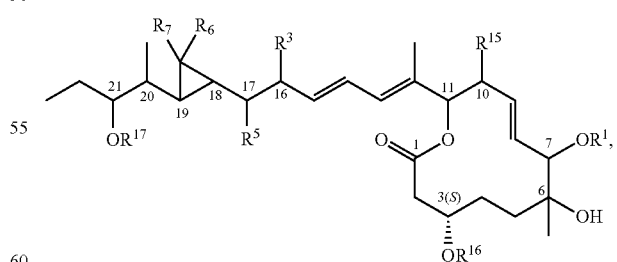

or a pharmaceutically acceptable salt thereof. $R^1$, $R^3$, $R^5$, $R^{15}$, $R^{16}$, and $R^{17}$ are as described above.

In embodiments, the carbon at position 6 has (S) stereochemistry. In embodiments, the compound has the formula (III-b),

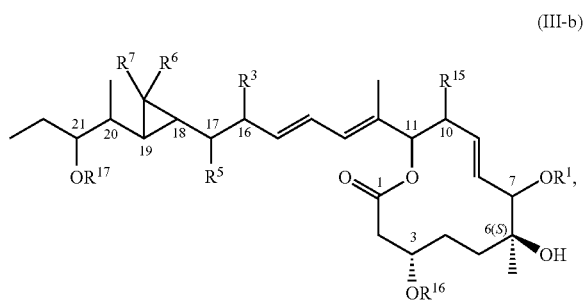

(III-b)

or a pharmaceutically acceptable salt thereof. R¹, R³, R⁵, R¹⁵, R¹⁶, and R¹⁷ are as described above.

In embodiments, the carbon at position 7 has (R) stereochemistry. In embodiments, the compound has the formula (III-c),

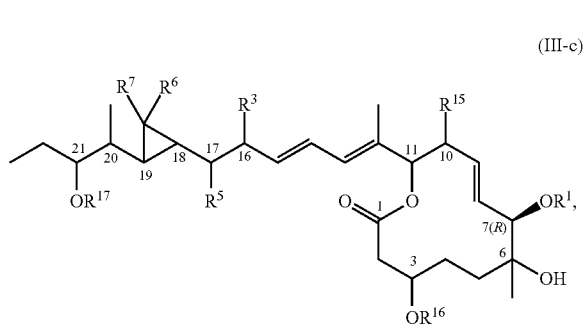

(III-c)

or a pharmaceutically acceptable salt thereof. R¹, R³, R⁵, R¹⁵, R¹⁶, and R¹⁷ are as described above.

In embodiments, the carbon at position 10 has (R) stereochemistry. In embodiments, the compound has the formula (III-d),

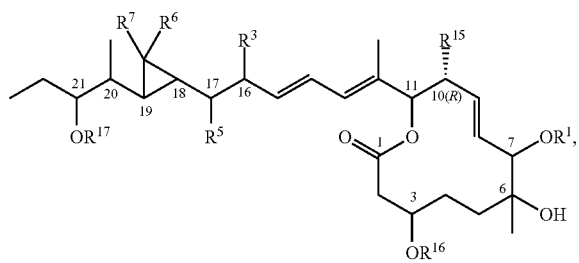

(III-d)

or a pharmaceutically acceptable salt thereof. R¹, R³, R⁵, R¹⁵, R¹⁶, and R¹⁷ are as described above.

In embodiments, the carbon at position 11 has (R) stereochemistry. In embodiments, the compound has the formula (III-e),

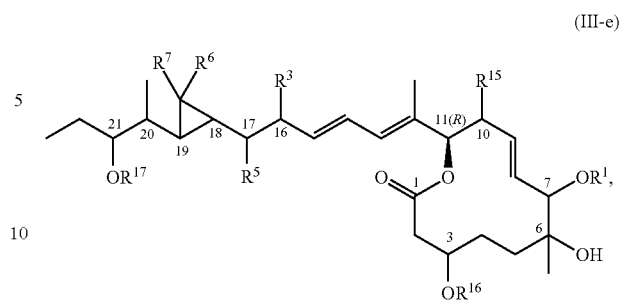

(III-e)

or a pharmaceutically acceptable salt thereof. R¹, R³, R⁵, R¹⁵, R¹⁶, and R¹⁷ are as described above.

In embodiments, the carbon at position 18 has (S) stereochemistry and the carbon at position 19 has (S) stereochemistry. In embodiments, the compound has the formula (III-f),

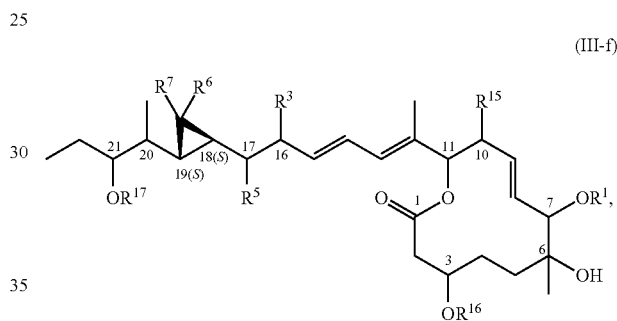

(III-f)

or a pharmaceutically acceptable salt thereof. R¹, R³, R⁵, R¹⁵, R¹⁶, and R¹⁷ are as described above.

In embodiments, the carbon at position 20 has (S) stereochemistry. In embodiments, the compound has the formula (III-g),

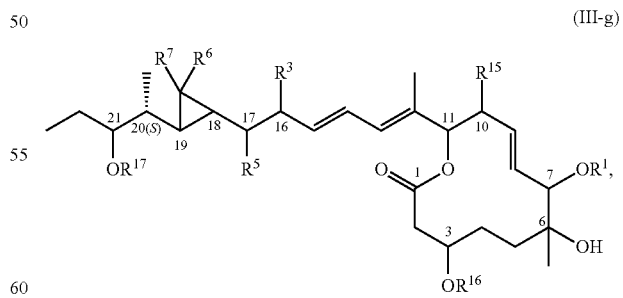

(III-g)

or a pharmaceutically acceptable salt thereof. R¹, R³, R⁵, R¹⁵, R¹⁶, and R¹⁷ are as described above.

In embodiments, the carbon at position 21 has (R) stereochemistry. In embodiments, the compound has the formula (III-h), (III-h)

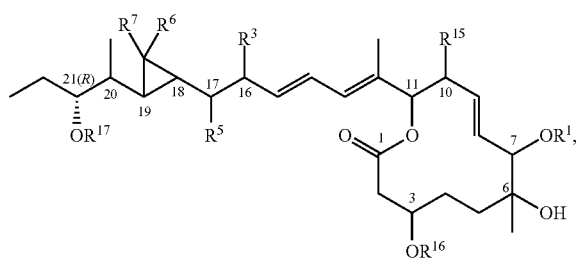

or a pharmaceutically acceptable salt thereof. $R^1$, $R^3$, $R^5$, $R^{15}$, $R^{16}$, and $R^{17}$ are as described above.

In embodiments, each $R^6$ and $R^7$ is independently hydrogen, halogen, or methyl.

In embodiments, $R^6$ is hydrogen. In embodiments, $R^6$ is halogen (e.g., —F, —Cl, —Br, or —I). In embodiments, $R^6$ is —F. In embodiments, $R^6$ is —Cl. In embodiments, $R^6$ is —Br. In embodiments, $R^6$ is —I. In embodiments, $R^6$ is unsubstituted $C_1$-$C_4$ alkyl. In embodiments, $R^6$ is methyl. In embodiments, $R^6$ is ethyl. In embodiments, $R^6$ is propyl. In embodiments, $R^6$ is isopropyl. In embodiments, $R^6$ is butyl. In embodiments, $R^6$ is t-butyl.

In embodiments, $R^7$ is hydrogen. In embodiments, $R^7$ is halogen (e.g., —F, —Cl, —Br, or —I). In embodiments, $R^7$ is —F. In embodiments, $R^7$ is —Cl. In embodiments, $R^7$ is —Br. In embodiments, $R^7$ is —I. In embodiments, $R^7$ is unsubstituted $C_1$-$C_4$ alkyl. In embodiments, $R^7$ is methyl. In embodiments, $R^7$ is ethyl. In embodiments, $R^7$ is propyl. In embodiments, $R^7$ is isopropyl. In embodiments, $R^7$ is butyl. In embodiments, $R^7$ is t-butyl.

In an aspect, provided is a compound having a structure of (X)

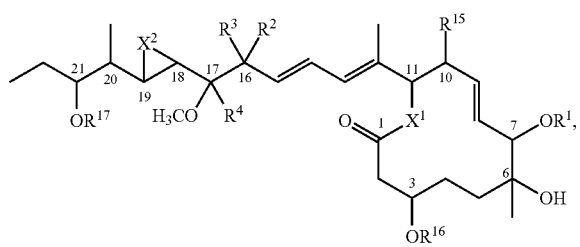

or a pharmaceutically acceptable salt thereof. $X^1$, $X^2$, $R^1$, $R^2$, $R^3$, $R^4$, $R^{15}$, $R^{16}$, and $R^{17}$ are as described above.

In embodiments, the compound has a structure of (XI)

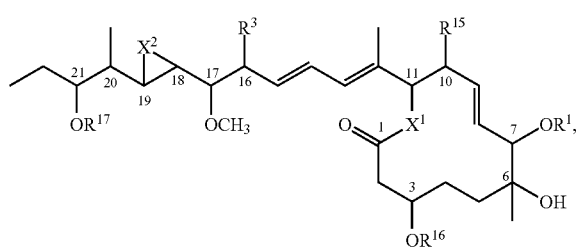

or a pharmaceutically acceptable salt thereof. $X^1$, $X^2$, $R^1R^2$, $R^3$, $R^4$, $R^{15}$, $R^{16}$, and $R^{17}$ are as described above.

In embodiments, the compound has a structure of (XI-S)

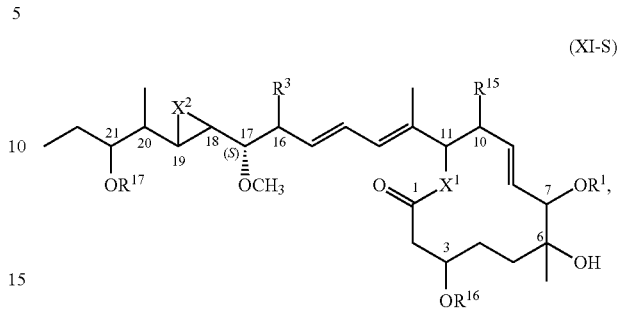

or a pharmaceutically acceptable salt thereof. $X^1$, $X^2$, $R^1$, $R^3$, $R^{15}$, $R^{16}$, and $R^{17}$ are as described above.

In embodiments, the compound has a structure of (XI-R)

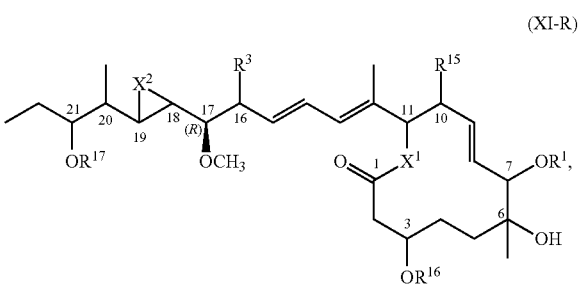

or a pharmaceutically acceptable salt thereof. $X^1$, $X^2$, $R^1$, $R^3$, $R^{15}$, $R^{16}$, and $R^{17}$ are as described above.

In embodiments, the carbon at position 3 has (S) stereochemistry. In embodiments, the compound has the formula (XII-a), (XII-a)

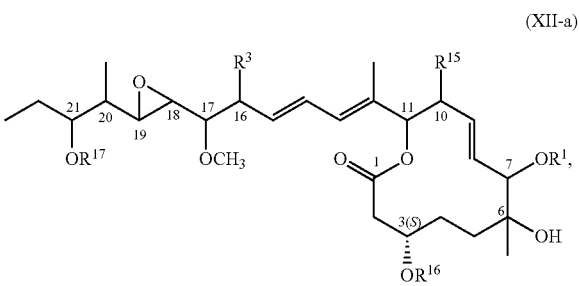

or a pharmaceutically acceptable salt thereof. $R^1$, $R^3$, $R^5$, $R^{15}$, $R^{16}$ and $R^{17}$ are as described above.

In embodiments, the carbon at position 6 has (S) stereochemistry. In embodiments, the compound has the formula (XII-b),

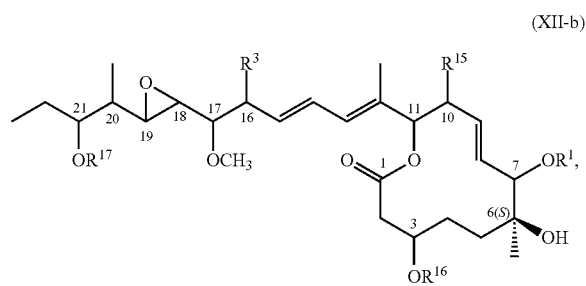

(XII-b)

or a pharmaceutically acceptable salt thereof. $R^1$, $R^3$, $R^5$, $R^{15}$, $R^{16}$ and $R^{17}$ are as described above.

In embodiments, the carbon at position 7 has (R) stereochemistry. In embodiments, the compound has the formula (XII-c),

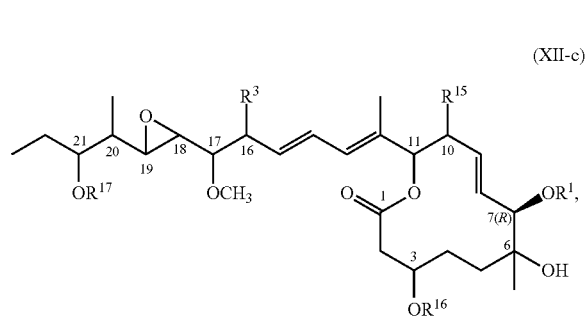

(XII-c)

or a pharmaceutically acceptable salt thereof. $R^1$, $R^3$, $R^5$, $R^{15}$, $R^{16}$ and $R^{17}$ are as described above.

In embodiments, the carbon at position 10 has (R) stereochemistry. In embodiments, the compound has the formula (XII-d),

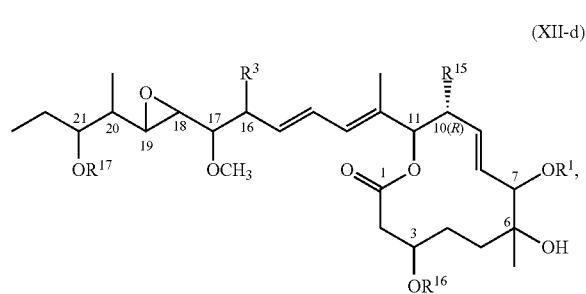

(XII-d)

or a pharmaceutically acceptable salt thereof. $R^1$, $R^3$, $R^5$, $R^{15}$, $R^{16}$, and $R^{17}$ are as described above.

In embodiments, the carbon at position 11 has (R) stereochemistry. In embodiments, the compound has the formula (XII-e),

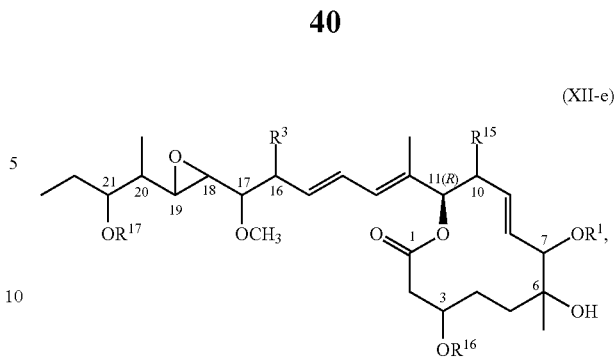

(XII-e)

or a pharmaceutically acceptable salt thereof. $R^1$, $R^3$, $R^5$, $R^{15}$, $R^{16}$, and $R^{17}$ are as described above.

In embodiments, the c carbon at position 18 has (S) stereochemistry and the carbon at position 19 has (S) stereochemistry. In embodiments, the compound has the formula (X-f),

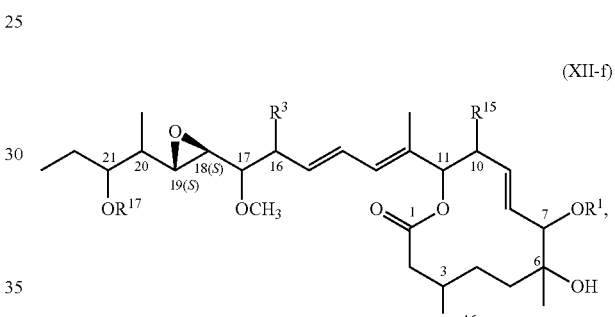

(XII-f)

or a pharmaceutically acceptable salt thereof. $R^1$, $R^3$, $R^5$, $R^{15}$, $R^{16}$, and $R^{17}$ are as described above.

In embodiments, the carbon at position 20 has (S) stereochemistry. In embodiments, the compound has the formula (XII-g),

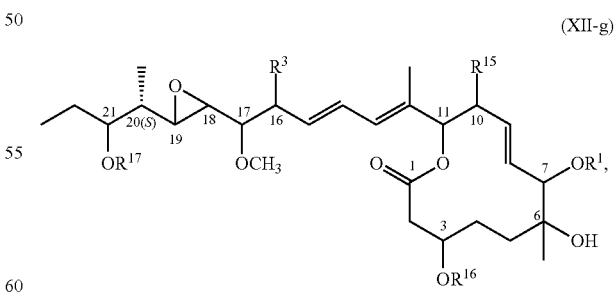

(XII-g)

or a pharmaceutically acceptable salt thereof. $R^1$, $R^3$, $R^5$, $R^{15}$, $R^{16}$, and $R^{17}$ are as described above.

In embodiments, the carbon at position 21 has (R) stereochemistry. In embodiments, the compound has the formula (XII-h), (XII-h)

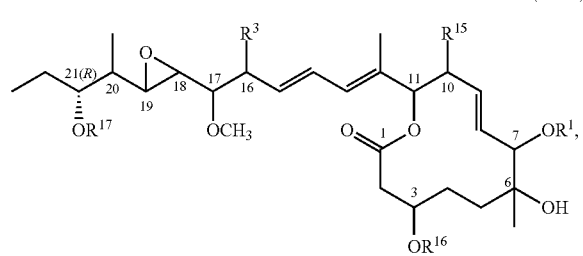

or a pharmaceutically acceptable salt thereof. $R^1$, $R^3$, $R^5$, $R^{15}$, $R^{16}$, and $R^{17}$ are as described above.

In embodiments, the compound is

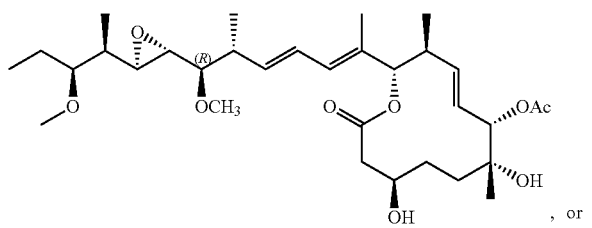

, or

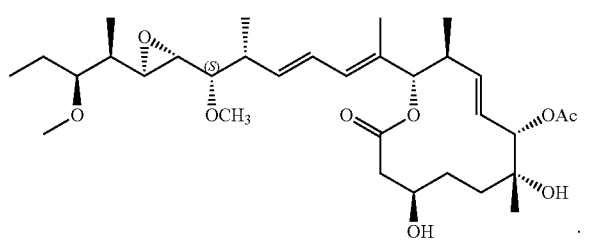

In embodiments, the compound is

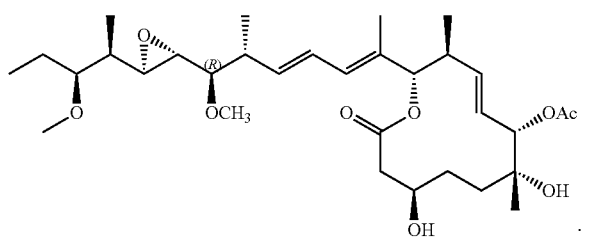

In embodiments, the compound is

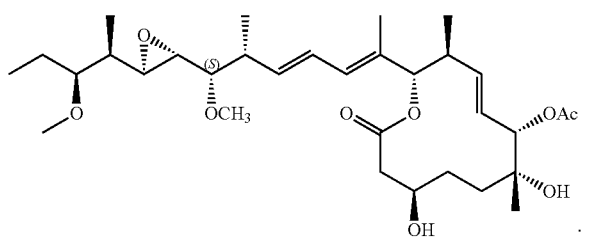

.

In embodiments, the compound is not

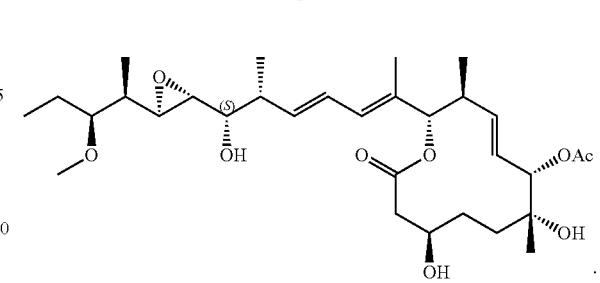

In embodiments, the compound is not

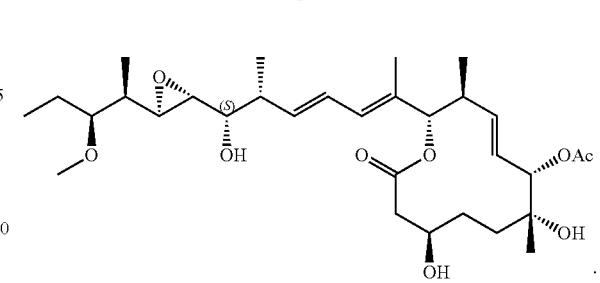

.

In embodiments, $R^1$ is hydrogen. In embodiments, $R^1$ is —C(O)$R^8$. In embodiments, $R^1$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^1$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, when $R^1$ is substituted, $R^1$ is substituted with a substituent group. In embodiments, when $R^1$ is substituted, $R^1$ is substituted with a size-limited substituent group. In embodiments, when $R^1$ is substituted, $R^1$ is substituted with a lower substituent group.

In embodiments, $R^2$ is hydrogen. In embodiments, $R^2$ is —O$R^9$. In embodiments, $R^2$ is —OC(O)$R^9$. In embodiments, $R^2$ is —OC(O)O$R^9$. In embodiments, $R^2$ is —OC(O)N$R^{10}R^{11}$. In embodiments, $R^2$ is substituted or unsubstituted alkyl (e.g., $C_1$-$C_{20}$, $C_1$-$C_8$, $C_1$-$C_6$, $C_1$-$C_4$, or $C_1$-$C_2$). In embodiments, $R^2$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^2$ is unsubstituted alkyl (e.g., $C_1$-$C_{20}$, $C_1$-$C_8$, $C_1$-$C_6$, $C_1$-$C_4$, or $C_1$-$C_2$). In embodiments, when $R^2$ is substituted, $R^2$ is substituted with a substituent group. In embodiments, when $R^2$ is substituted, $R^2$ is substituted with a size-limited substituent group. In embodiments, when $R^2$ is substituted, $R^2$ is substituted with a lower substituent group.

In embodiments, $R^3$ is hydrogen. In embodiments, $R^3$ is —O$R^9$. In embodiments, $R^3$ is —OC(O)$R^9$. In embodiments, $R^3$ is —OC(O)O$R^9$. In embodiments, $R^3$ is —OC(O)N$R^{10}R^{11}$. In embodiments, $R^3$ is substituted or unsubstituted alkyl (e.g., $C_1$-$C_{20}$, $C_1$-$C_8$, $C_1$-$C_6$, $C_1$-$C_4$, or $C_1$-$C_2$). In embodiments, $R^3$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^3$ is unsubstituted alkyl (e.g., $C_1$-$C_{20}$, $C_1$-$C_8$, $C_1$-$C_6$, $C_1$-$C_4$, or $C_1$-$C_2$). In embodiments, when $R^3$ is substituted, $R^3$ is substituted with a substituent group. In embodiments, when $R^3$ is substituted, $R^3$ is substituted with a size-limited substituent group. In embodiments, when $R^3$ is substituted, $R^3$ is substituted with a lower substituent group.

In embodiments, $R^4$ is hydrogen. In embodiments, $R^4$ is —O$R^9$. In embodiments, $R^4$ is —OC(O)$R^9$. In embodiments, $R^4$ is —OC(O)O$R^9$. In embodiments, $R^4$ is —OC(O)N$R^{10}R^{11}$. In embodiments, $R^4$ is substituted or unsubstituted alkyl (e.g., $C_1$-$C_{20}$, $C_1$-$C_8$, $C_1$-$C_6$, $C_1$-$C_4$, or $C_1$-$C_2$). In embodiments, $R^4$ is substituted alkyl (e.g., $C_1$-$C_{20}$, $C_1$-$C_8$, $C_1$-$C_6$, $C_1$-$C_4$, or $C_1$-$C_2$). In embodiments, $R^4$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, when $R^4$ is substituted, $R^4$ is substituted with a substituent group. In embodiments, when $R^4$ is substituted, $R^4$ is substituted with a size-limited substituent group. In embodiments, when $R^4$ is substituted, $R^4$ is substituted with a lower substituent group.

In embodiments, $R^5$ is hydrogen. In embodiments, $R^5$ is $-OR^9$. In embodiments, $R^5$ is $-OC(O)R^9$. In embodiments, $R^5$ is $-OC(O)OR^9$. In embodiments, $R^5$ is $-OC(O)NR^{10}R^{11}$. In embodiments, $R^5$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^5$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^5$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, when $R^5$ is substituted, $R^5$ is substituted with a substituent group. In embodiments, when $R^5$ is substituted, $R^5$ is substituted with a size-limited substituent group. In embodiments, when $R^5$ is substituted, $R^5$ is substituted with a lower substituent group.

In embodiments, $R^6$ is hydrogen. In embodiments, $R^6$ is halogen (e.g., $-F$, $-Cl$, $-Br$, or $-I$). In embodiments, $R^6$ is $-OR^{12}$. In embodiments, $R^6$ is $-OC(O)R^{12}$. In embodiments, $R^6$ is $-OC(O)OR^{12}$. In embodiments, $R^6$ is $-OC(O)NR^{13}R^{14}$. In embodiments, $R^6$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^6$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^6$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^6$ is substituted or unsubstituted aryl (e.g., $C_6$-$C_{12}$, $C_6$-$C_{10}$, or phenyl). In embodiments, $R^6$ is substituted aryl (e.g., $C_6$-$C_{12}$, $C_6$-$C_{10}$, or phenyl). In embodiments, $R^6$ is unsubstituted aryl (e.g., $C_6$-$C_{12}$, or phenyl). In embodiments, when $R^6$ is substituted, $R^6$ is substituted with a substituent group. In embodiments, when $R^6$ is substituted, $R^6$ is substituted with a size-limited substituent group. In embodiments, when $R^6$ is substituted, $R^6$ is substituted with a lower substituent group.

In embodiments, $R^7$ is hydrogen. In embodiments, $R^7$ is halogen (e.g., $-F$, $-Cl$, $-Br$, or $-I$). In embodiments, $R^7$ is $-OR^{12}$. In embodiments, $R^7$ is $-OC(O)R^{12}$. In embodiments, $R^7$ is $-OC(O)OR^{12}$. In embodiments, $R^7$ is $-OC(O)NR^{13}R^{14}$. In embodiments, $R^7$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^7$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^7$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^7$ is substituted or unsubstituted aryl (e.g., $C_6$-$C_{12}$, $C_6$-$C_{10}$, or phenyl). In embodiments, $R^7$ is substituted aryl (e.g., $C_6$-$C_{12}$, $C_6$-$C_{10}$, or phenyl). In embodiments, $R^7$ is unsubstituted aryl (e.g., $C_6$-$C_{12}$, or phenyl). In embodiments, when $R^7$ is substituted, $R^7$ is substituted with a substituent group. In embodiments, when $R^7$ is substituted, $R^7$ is substituted with a size-limited substituent group. In embodiments, when $R^7$ is substituted, $R^7$ is substituted with a lower substituent group.

In embodiments, $R^8$ is independently hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^8$ is independently substituted alkyl (e.g., $C_1$-$C_{20}$, $C_1$-$C_{12}$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_8$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^8$ is independently unsubstituted alkyl (e.g., $C_1$-$C_{20}$, $C_1$-$C_{12}$, $C_1$-$C_6$, $C_1$-$C_4$, or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^8$ is substituted, $R^8$ is substituted with a substituent group. In embodiments, when $R^8$ is substituted, $R^8$ is substituted with a size-limited substituent group. In embodiments, when $R^8$ is substituted, $R^8$ is substituted with a lower substituent group. In embodiments, $R^8$ is independently hydrogen.

In embodiments, $R^9$ is independently hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_3$-$C_6$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^9$ is independently substituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_{10}$, $C_3$-$C_8$, $C_3$-$C_6$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^9$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^9$ is substituted, $R^9$ is substituted with a substituent group. In embodiments, when $R^9$ is substituted, $R^9$ is substituted with a size-limited substituent group. In embodiments, when $R^9$ is substituted, $R^9$ is substituted with a lower substituent group. In embodiments, $R^9$ is independently hydrogen.

In embodiments, $R^{10}$ is independently hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_3$-$C_6$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^{10}$ is independently substituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_{10}$, $C_3$-$C_8$, $C_3$-$C_6$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^{10}$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^{10}$ is substituted, $R^{10}$ is substituted with a substituent group. In embodiments, when $R^{10}$ is substituted, $R^{10}$ is substituted with a size-limited substituent group. In embodiments, when $R^{10}$ is substituted, $R^{10}$ is substituted with a lower substituent group. In embodiments, $R^{10}$ is independently hydrogen.

In embodiments, $R^{11}$ is independently hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_3$-$C_6$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^{11}$ is independently substituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_{10}$, $C_3$-$C_8$, $C_3$-$C_6$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^{11}$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^{11}$ is substituted, $R^{11}$ is substituted with a substituent group. In embodiments, when $R^{11}$ is substituted, $R^{11}$ is substituted with a size-limited substituent group. In embodiments, when $R^{11}$ is substituted, $R^{11}$ is substituted with a lower substituent group. In embodiments, $R^{11}$ is independently hydrogen.

In embodiments, $R^2$ is independently hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_3$-$C_6$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^{12}$ is independently substituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_{10}$, $C_3$-$C_8$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^{12}$ is independently unsubstituted alkyl (e.g., $C_1$-$C_{20}$, $C_1$-$C_6$, $C_1$-$C_4$, or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^{12}$ is substituted, $R^{12}$ is substituted with a substituent group. In embodiments, when $R^{12}$ is substituted, $R^{12}$ is substituted with a size-limited substituent group. In embodiments, when $R^{12}$ is substituted, $R^{12}$ is substituted with a lower substituent group. In embodiments, $R^{12}$ is independently hydrogen.

In embodiments, $R^{13}$ is independently hydrogen, or substituted or unsubstituted alkyl (e.g., $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^{13}$ is independently substituted alkyl (e.g., $C_1$-$C_{20}$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_{10}$, $C_3$-$C_8$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^{13}$ is independently unsubstituted alkyl (e.g., $C_1$-$C_{20}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^3$ is substituted, $R^3$ is substituted with a substituent group. In embodiments, when $R^3$ is substituted with a size-limited substituent group. In embodiments, when $R^3$ is substituted, $R^3$ is substituted with a lower substituent group. In embodiments, $R^{13}$ is independently hydrogen.

In embodiments, $R^4$ is independently hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted or unsubstituted cycloalkyl (e.g., $C_3$-$C_{10}$, $C_3$-$C_8$, $C_3$-$C_6$, $C_4$-$C_6$, or $C_5$-$C_6$), substituted or unsubstituted heterocycloalkyl (e.g., 3 to 10 membered, 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12 membered, 5 to 10 membered, 5 to 8 membered, or 5 to 6 membered). In embodiments, $R^{14}$ is independently substituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted heteroalkyl (e.g., 2 to 20 membered, 2 to 12 membered, 2 to 8 membered, 2 to 6 membered, 4 to 6 membered, 2 to 3 membered, or 4 to 5 membered), substituted cycloalkyl (e.g., $C_3$-$C_{10}$, $C_3$-$C_8$, $C_3$-$C_6$, $C_4$-$C_6$, or $C_5$-$C_6$), substituted heterocycloalkyl (e.g., 3 to 10 membered, 3 to 8 membered, 3 to 6 membered, 4 to 6 membered, 4 to 5 membered, or 5 to 6 membered), substituted aryl (e.g., $C_6$-$C_{12}$, $C_6$-$C_{10}$, or phenyl), or substituted heteroaryl (e.g., 5 to 12 membered, 5 to 10 membered, 5 to 8 membered, or 5 to 6 membered). In embodiments, $R^{14}$ is independently unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 8 membered, or 5 to 6 membered). In embodiments, when $R^{11}$ is substituted, $R^4$ is substituted with a substituent group. In embodiments, when $R^{11}$ is substituted, $R^4$ is substituted with a size-limited substituent group. In embodiments, when $R^{11}$ is substituted, $R^4$ is substituted with a lower substituent group. In embodiments, $R^{11}$ is independently hydrogen.

In embodiments, $R^{15}$ is hydrogen, or substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{15}$ is substituted or unsubstituted alkyl (e.g., $C_1$-$C_{20}$, $C_1$-$C_8$, $C_1$-$C_6$, $C_1$-$C_4$, or $C_1$-$C_2$). In embodiments, $R^{15}$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{15}$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, when $R^{15}$ is substituted, $R^{15}$ is substituted with a substituent group. In embodiments, when $R^{15}$ is substituted, $R^{15}$ is substituted with a size-limited substituent group. In embodiments, when $R^{15}$ is substituted, $R^{15}$ is substituted with a lower substituent group. In embodiments, $R^{15}$ is hydrogen.

In embodiments, $R^{16}$ is hydrogen. In embodiments, $R^{16}$ is —C(O)$R^8$. In embodiments, $R^{16}$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{16}$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{16}$ is unsubstituted alkyl (e.g., $C_1$-$C_{20}$, $C_1$-$C_8$, $C_1$-$C_6$, $C_1$-$C_4$, or $C_1$-$C_2$). In embodiments, when $R^{16}$ is substituted, $R^{16}$ is substituted with a substituent group. In embodiments, when $R^{16}$ is substituted, $R^{16}$ is substituted with a size-limited substituent group. In embodiments, when $R^{16}$ is substituted, $R^{16}$ is substituted with a lower substituent group.

In embodiments, $R^5$ is hydrogen. In embodiments, $R^5$ is —C(O)$R^8$. In embodiments, $R^5$ is substituted or unsubstituted alkyl (e.g., $C_1$-$C_{20}$, $C_1$-$C_8$, $C_1$-$C_6$, $C_1$-$C_4$, or $C_1$-$C_2$). In embodiments, $R^5$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^5$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, when $R^5$ is substituted, $R^5$ is substituted with a substituent group. In embodiments, when $R^5$ is substituted, $R^5$ is substituted with a size-limited substituent group. In embodiments, when $R^5$ is substituted, $R^5$ is substituted with a lower substituent group.

Pharmaceutical Compositions

Also provided herein are pharmaceutical formulations. In embodiments, the pharmaceutical formulation includes a compound (e.g. Formulae (I), (II-a), (II-b), (II-c), (II-d), (II-e), (II-f), (II-g), (II-h), (III-a), (III-b), (III-c), (III-d), (III-e), (III-f), (III-g), (III-h), (X), (XI-S), (XI-R), (XII-a), (XII-b), (XII-c), (XII-d), (XII-e), (XII-f), (XII-g), or (XII-h)) described above (including all embodiments thereof) and a pharmaceutically acceptable excipient.

The pharmaceutical composition may contain a dosage of the compound in a therapeutically effective amount.

1. Formulations

The pharmaceutical composition may be prepared and administered in a wide variety of dosage formulations. Compounds described herein (e.g., having a structure of Formula (I), (II-a), (II-b), (II-c), (II-d), (II-e), (II-f), (II-g), (II-h), (III-a), (III-b), (III-c), (III-d), (III-e), (III-f), (III-g), (III-h), (X), (XI-S), (XI-R), (XII-a), (XII-b), (XII-c), (XII-d), (XII-e), (XII-f), (XII-g), or (XII-h)) may be administered orally, rectally, or by injection (e.g. intravenously, intramuscularly, intracutaneously, subcutaneously, intraduodenally, or intraperitoneally).

For preparing pharmaceutical compositions from compounds described herein (e.g., having a structure of Formula (I), (II-a), (II-b), (II-c), (II-d), (II-e), (II-f), (II-g), (II-h), (III-a), (III-b), (III-c), (III-d), (III-e), (III-f), (III-g), (III-h), (X), (XI-S), (XI-R), (XII-a), (XII-b), (XII-c), (XII-d), (XII-e), (XII-f), (XII-g), or (XII-h)), pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutic composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat leukemia (e.g., chronic lymphocytic leukemia), such compositions will contain amounts of active ingredients effective to achieve the desired result (e.g. increasing the extent of cancer cell death in the patient).

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (19th Ed., Mack Pub. Co., Easton, PA) and WO 96/05309, the teachings of both of which are hereby incorporated by reference.

Methods of Making

Provided herein are methods for process scaled synthesis of complex polyketide compounds. The methods provided herein may provide control of regioselective bond assembly. The methods may provide installation of stereocenters with enantioselectivity. The methods may provide synthetic access to single stereoisomeric and single atom isotopically-labeled analogs.

Thus, in an aspect is provided method of making a compound having the formula

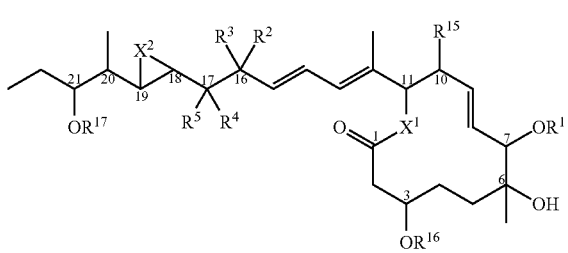

or an analog thereof, the method including contacting a side chain compound with a core compound. $X^1$, $X^2$, $R^2$, $R^3$, $R^4$, $R^5$, $R^{15}$, $R^{16}$, and $R^{17}$ are as described above.

In embodiments, the analog is a stereoisomer of the compound. In embodiments, the analog includes a site-specific isotopic tag.

In an aspect is provided a method of making a compound having the formula (I)

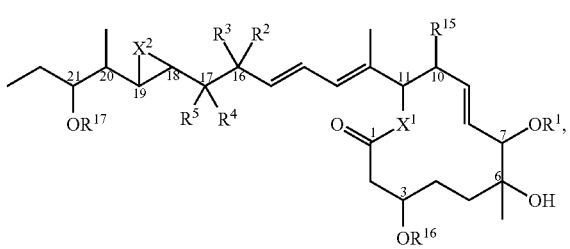

the method including contacting a side chain compound with a core compound, wherein the side chain compound has the formula

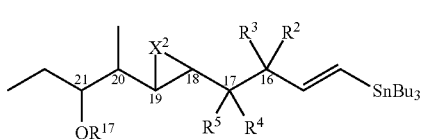

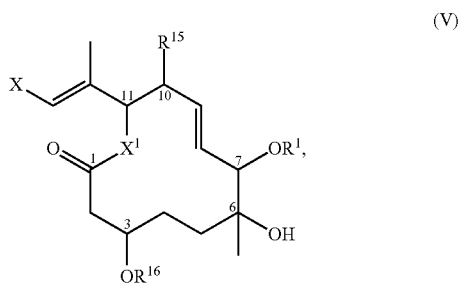

(V)

wherein X is halogen. $X^1$, $X^2$, $R^1$, $R^2$, $R^3$, $R^4$, $R^5$, $R^{15}$, $R^{16}$, and $R^{17}$ are as described above.

Thus, in an aspect is provided method of making a compound having the formula

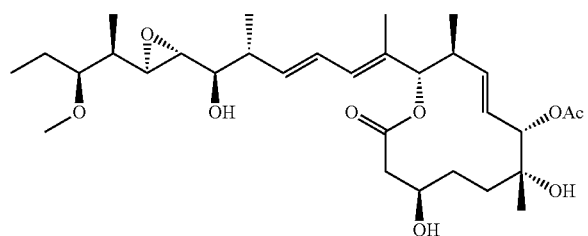 [SMILES: CC[C@H](OC)[C@@H](C)[C@H]1O[C@@H]1[C@H](O)[C@H](C)/C=C/C=C(\C)[C@H]1OC(=O)C[C@H](O)CC[C@@](C)(O)[C@@H](OC(C)=O)/C=C/[C@@H]1C]

or an analog thereof, the method including contacting a side chain compound with a core compound.

In an aspect is provided method of making a compound having the formula

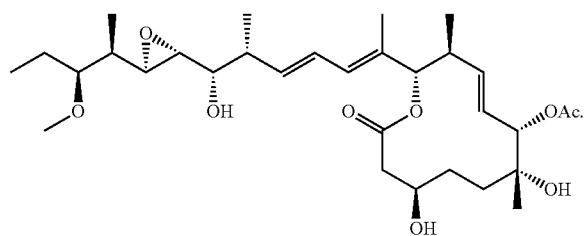 [SMILES: CC[C@H](OC)[C@@H](C)[C@H]1O[C@@H]1[C@@H](O)[C@H](C)/C=C/C=C(\C)[C@H]1OC(=O)C[C@H](O)CC[C@@](C)(O)[C@@H](OC(C)=O)/C=C/[C@@H]1C]

The method including contacting a side chain compound with a core compound, wherein the side chain compound has the formula

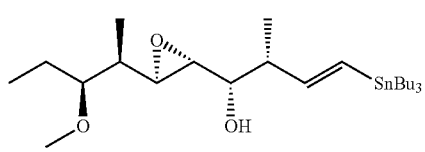

and the core compound has the formula

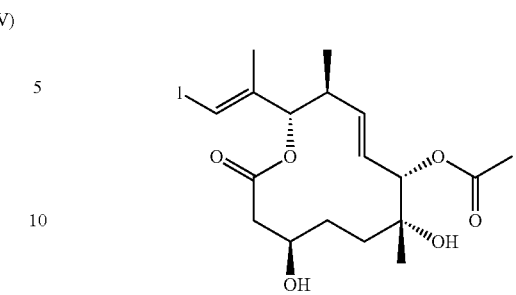

In embodiments, the method further includes preparing optically pure compounds as described above. The method may include, during the synthesis (e.g., FIGS. 3 to 13), a step of isolating enantiomers having each chiral carbon (e.g., carbon at position 3 having (S) stereochemistry; carbon at position 6 having (S) stereochemistry; carbon at position 7 having (R) stereochemistry; carbon at position 10 having (R) stereochemistry; carbon at position 11 having (R) stereochemistry; carbon at position 17 having (S) stereochemistry; carbon at position 18 having (S) stereochemistry and carbon at position 19 having (S) stereochemistry; carbon at position 20 has (S) stereochemistry; or carbon at position 21 having (R) stereochemistry). For separation of enantiomers, any techniques and methods generally used in the chemical arts can be used without limitation.

Methods of Use

In an aspect is provided a method of modulating spliceosome activity, the method including contacting a spliceosome complex with a compound provided herein including embodiments thereof.

In another aspect a method of treating cancer is provided. The method includes administering to a subject in need thereof, a therapeutically effective amount of a compound of formula (I), (II-a), (II-b), (II-c), (II-d), (II-e), (II-f), (II-g), (II-h), (III-a), (III-b), (III-c), (III-d), (III-e), (III-f), (III-g), (III-h), (X), (XI-S), (XI-R), (XII-a), (XII-b), (XII-c), (XII-d), (XII-e), (XII-f), (XII-g), or (XII-h), or analogues thereof. The compound may be co-administered with a pharmaceutically acceptable excipient, as addressed in previous sections. In embodiments, the cancer may be leukemia, lymphoma, metastatic cancer or bone cancer. The cancer may be leukemia or lymphoma. In embodiments, the cancer may be chronic lyphocytic cancer (CLL).

In another aspect a method of treating fungal infection is provided. The method includes administering to a subject in need thereof, a therapeutically effective amount of a compound of formula (I), (II-a), (II-b), (II-c), (II-d), (II-e), (II-f), (II-g), (II-h), (III-a), (III-b), (III-c), (III-d), (M-e), (III-f), (III-g), (III-h), (X), (XI-S), (XI-R), (XII-a), (XII-b), (XII-c), (XII-d), (XII-e), (XII-f), (XII-g), or (XII-h), or analogues thereof. The compound may be co-administered with a pharmaceutically acceptable excipient, as addressed in previous sections.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Natural products continue to deliver potent compounds for clinical entry with targets and activity unachievable by other synthetic or biological endeavors. While potent and active in vitro, the translation of these materials for human use often require the development of total synthetic approach that enables one to address stereochemistry and functionality at each carbon center. While challenging, access to the synthetically-derived material is only the first hurdle in translating materials that can reach the clinic. Here, we describe the chemical synthesis of 5S-FD-895, a polyketide, whose unique biological activity arises from its ability to modulate the spliceosome. Challenged with enabling access, our team established methods to ensure three critical criteria to enable clinical translation, namely: gram scale access, access to an exhaustive understanding of the lead molecules structure activity relationships (SARs) and a high-degree of stereochemical control. The latter challenge proved critical to this study as isomeric by-products have been shown to participate in the SAR by altering not only level of activity, but also, the overall genetic response.

Example 1: Scalable Synthesis of 17S-FD-895

Since their first discovery in the mid-1990s, families of polyketide natural products, including FD-895, the pladienolides, the spliceostatins, herboxidiene, and the thailanstatins, have garnered interest due to selective antitumor activities. In recent years, two lead candidates, E7107 and H3B-8800, have advanced to Phase I clinical trials for solid tumors and leukemia. Mode of action studies indicate that they share similar abilities to modulate splicing through interactions within the SF3B component of the spliceosome. First suggested as a consensus motif and later validated by structural analyses, these small molecules uniquely position themselves at an interface between SF3B1, PHF5A, and SF3B3, a hinge region involved in regulating the branch site adenosine-binding pocket. These splice modulators all possess a similar structural backbone containing a macrolactone ring linked by a diene to a side chain. Here, the importance and positioning of the stereochemical centers within these molecules clearly indicates a unique geometrical requirement for activity.

While many of these splice modulators display the necessary functional spatiality to enable facile binding to the SF3B pocket in vitro, the high density of their functional groups results in a low stability in biological media resulting in short half-lives ($t_{1/2} \leq 30$ min). Recent studies now indicate that synthetic modifications along the side chain are not only tolerated, but allow for access to a three-dimensional arrangement that reduces the rate of degradation. These studies also indicate that synthetic analogs meet the requirements for active binding to the spliceosome pocket in vivo. This ultimately led to our identification of 17S-FD-895 (1d, FIG. 2) as a therapeutic lead.

While efforts have been developed to access gram scale quantities of pladienolides via fermentation, these approaches have been limited to the production of natural materials. To access the non-natural $C_{17}$ stereocenter in 17S-FD-895, we focused on a synthetic approach. To date, reported gram scale synthesis has enabled access only to the less-complex herboxidiene. The synthetic challenges in facing gram scale preparation of 17S-FD-895 (1d, FIG. 1A), include: 11 total stereocenters (6 contiguous), a substituted diene, remote functionality, a quaternary carbon and a 12-membered lactone. Our approach (FIG. 1A) expanded on prior milligram-scaled campaigns (FIG. 1B) that identified the importance of component assembly. As 1 possesses potent biological activity, with a human maximum tolerated dose (MTD) estimated at 4 mg/m$^2$ based on E7107, we opted for a route that avoided production of active materials until the final step. In general, we targeted a process that would be amenable for large-scale synthesis by reducing operations and chromatographic requirements.

Results

We began by developing methods to prepare 20 g (0.039 mol) of side chain 2 (FIG. 7A) to secure over 15 g (0.027 mol) of 1d. This started with optimization and preparation of Crimmins' auxiliary 7 on a kilogram scale. Diastereoselective aldol addition, followed by aminolysis and subsequent methylation, enabled the successful transition to 155 g (0.82 mol) of Weinreb amide 10 per batch from 235 g (0.94 mol) of 7. Fortunately, we were able to recover 65±5% of 6. At this point, we encountered our first challenge: the high volatility of aldehyde 11. This was circumvented by a solvent change to 2-methyltetrahydrofuran, enabling reduction of 10 and homologation to 12 without isolation of 11. Next, DIBAL-H reduction afforded alcohol 13, which could be stored at 4° C. for over 2 years. Sharpless epoxidation of 13 provided 14 with a 6:1 dr (diastereomeric ratio), which was oxidized to 15 by use of TEMPO. As shown in Scheme 1, condensation of aldehyde 15 with Marshall allenylstannane 16 provided alkyne 17d.

The next issue arose in the hydrostannylation of 17d, where the use of a palladium catalyst generated only a 1:5 α:β regioselectivity. This led to contamination by traces of the undesired α-vinylstannane, which was reduced by use of Figueroa's molybdenum catalyst to a 1:10 dr favoring the desired β-stannane. Ultimately, effective chromatographic conditions assisted access to 2d with 95+% purity that was established by LC/MS analysis. To date, we have stocked over 200 g (1.3 mol) of 13. Over multiple repetitions, we were able to synthesize 6.5±0.5 g (0.013 mol) of 2d from 25 g (0.16 mol) of 13 in a week.

Parallel efforts were also launched to produce 20 g (0.043 mol) of 3. We developed scalable methods to prepare intermediate 22 in 300 g batches from mono-protected 18. To achieve this, TEMPO oxidations enabled scalable conversion of 18 to 19 and 20 to 21 without chromatography. Reducing the reaction temperature (−78° C. to −94° C.) improved the dr (85% to 95%) of the allylboration of aldehyde 19 to 20. Solvent change (THF to Et$_2$O) and reaction temperature optimization (−78° C. to −94° C.) improved the selectivity of the Grignard addition (85% to 90% dr) to 21 affording 22. This process currently requires a single chromatographic step (20). With a stability of over 4 years at −20° C., compound 22 provides an ideal storage point for batch preparation of core 3.

The conversion of 22 to 3 provided the most significant challenge. Previously established methods to convert 22 to 23 relied on extremely pure ZnBr$_2$, which caused issues due to its hygroscopicity. After reaction screening, we observed that the in situ decomposition of CBr$_4$ in i-PrOH reproducibly returned 65±5% of 23, enabling three transformations in one step. The next challenge arose in the installation of the $C_1$-$C_3$ fragment. Upon oxidation to 24, we installed the remote $C_3$ stereocenter in 9:1 dr using a chiral tert-leucine derived thiazolidinethione auxiliary. Subsequent protection and saponification afforded acid 27, which was esterified with alcohol 33 in neat pivalic anhydride to afford 34. These conditions operated without solvent and were high yielding and reproducible. This 6-step sequence could be conducted in 3 days, accessing 10 g (0.015 mol) batches of 34 from 25 g (0.069 mol) of 22. At this point, we had installed the remaining 5 stereocenters required for 1 with 95+% purity in 34.

Next, we turned our attention to the challenging ring closing metathesis. Previously, the reaction had been performed at a maximum of 1 g and suffered from allylic isomerization despite the use of additives. After screening catalysts and reaction conditions, we discovered that inverting the order of addition (a solution of 2' Hoveyda-Grubbs catalyst in toluene to 34 in refluxing toluene) provided acceptable yields of 35 on the 5-10 g scale.

Subsequent global deprotection of 35 with mild acid, followed by selective acetylation of C7 in 36 via orthoester formation, yielded core 3. After optimization, we are now able to convert 30 g (0.083 mol) of 22 to 1.8±0.2 g (0.0039 mol) of 3 (95+% purity via LC/MS) in less than 2 weeks.

At this stage, we were set for the final step. We opted for a Stille cross-coupling at C13-C14, as alternate installation of the C14-C15 olefin by cross-metathesis or Julia-Kocienski olefination (FIG. 1B) can be complicated by the formation of undesired cis-olefins. After parallelized-reaction screening, we settled on an olefin coupling using Buchwald's XPhos Pd G2 catalyst with CuCl and KF in anhydrous t-BuOH.[37] Under Class III safety conditions, we prepared 1d in 80±2% yield, with a worker exposure of less than 3 h per 5 g batch (a key step in deducing risk from this potent agent, MTD at 4 mg/kg). Fortunately, we were able to recover 16±3% of 3, which could be recycled, providing an effective mass balance in the conversion of 3 to 1d. Side chain 2 was not recoverable.

To provide materials to assist purity analyses, we introduced $^{13}C$ labels in 1d independently at C1 and C30. The $^{13}C$ isotopic tag at C1 was installed by preparing the Sammakia auxiliary with 1-$^{13}C$ acetyl chloride, relaying it to the corresponding $^{13}C$1-labeled core 3, and coupling it with side chain 2d to afford 1 g of $^{13}C$1-17S-FD-895. The 13C tag at C30 was introduced by selective acetylation of 36 with 1-$^{13}C$ acetic anhydride. The resulting $^{13}C$30-labeled 3 was coupled to 2d to prepare 100 mg of $^{13}C$30-17S-FD-895. $^{13}C$-NMR spectroscopy confirmed that batches of $^{13}C$1-17S-FD-895 and $^{13}C$30-17S-FD-895 were a single compound with 99% purity. Overall, this improved route has produced over 17 g of 17S-FD-895, with all 11 stereocenters installed in high selectivity and reproducibility. Furthermore, the ability to produce gram scale lots of stable, isotopically labeled material is especially advantageous for in vivo pharmacological assessments.

Next, we wanted to expand the stereochemical structure activity relationship (s-SAR) profile of FD-895 by utilizing our route to access non-natural analogs from late stage intermediates. The C3-isomer and the C7-isomer were synthesized by changes in chiral reagents and along with 1d were confirmed by NMR peak shift comparisons. Comparing the activity of analogs 1d, C3-isomer and the C7-isomer to the natural product, FD-895, in human colorectal tumor HCT-116 cells indicated that inverting the C3 and C7 stereocenters in C3-isomer and the C7-isomer, respectively, compromised activity, while the C17 isomer in 1d retained potency.

Discussion

These results were consistent with established X-ray crystal structure of the SF3B core complexed with pladienolide B. In this and related structures, inverting the C3 hydroxyl-group in 1a (FIG. 2) ablates its interaction with K1071 of the SF3B1 subunit. The lack in activity of the C7 isomer followed a similar reasoning, as inversion of the C7 acetate in 1k (FIG. 2) disrupts its interaction with R38 in PHF5A. These findings support a strict SAR within the 12-membered core, as it bridges the interface between SF3B1 and PHF5A. Tolerance for inversion of C17 in 1d, was also supported structurally. Rotational freedom within the side chain permitted pladienolide B and associated analogs to adopt distinct conformations to access the same binding pocket. Overall, this synthesis has facilitated material access to complete preclinical evaluation (setting the stage for development of improved GMP manufacturing protocols), delivered isotopic materials, filled gaps in the SAR data, and contributed to an understanding of structural features required to engage small molecule splice modulation.

Example 2: Stereochemical Attenuation of Splice Modulation

Due to their ability to form highly-functionalized macrocyclic skeletons, polyketide natural products gain access to rare spatial arrangements of atoms, and in turn, enables them to access protein pockets within protein complexes. First reported in the mid-1990s and advance ever since, splicing modulators present a unique consensus motif that was only recently identified through protein X-ray crystallography. Here, we report on the application of solution state NMR along with activity analyses to explore the structural dynamics of FD-895 by examining the effects of stereochemical modifications at specific centers within the molecule.

In 1994, a team at Taisho Pharmaceutical Co. Ltd reported the discovery of a new 12-membered macrolide, FD-895 (1) from strain A-9561 isolated from a soil sample collected at Iromote Island, Japan. Nearly a decade later, efforts at the Tsikuba Research Laboratories of Eisai Co. Ltd reported the discovery of a set of C17-deoxy, C31-demethyl analogues of FD-895 from a strain of *Streptomyces platensis* Mer-11107, and renamed the materials as pladienolides. While not recognized at the time, parallel efforts by Fujisawa Pharmaceutical Co. Ltd. in 1996 and Monsanto Co. in 1992 lead to the discoveries of FR901463-5 from *Pseudomonas* sp. and herboxidiene from strain A7847, respectively.

While not realized at the time, all three of these classes of natural products would be united through a series of parallel mode of action (MOA) studies beginning in 2007 that illustrated their common targeting of the SF3B complex of the human spliceosome. In 2006, a team led by Lührmann, Pena and Cretu completed the X-ray crystal structure of the core SF3B complex. This structure was followed by that SF3B complex bound to pladienolide B (11, FIG. 2) and has since been furthered to provide detailed structures additional analogs including FD-895 (1). As shown in FIG. 1, these SPLMs occupy two-sphere shaped pocket where the diene C12-C14 occupies as tunnel between pockets that bind to either the core (C1-C11) and side chain (C12-C23). Here, FD-895 (1) adopts a conformation that enables the hydrophylic side chain to uniquely position itself between V1100 and F1153 in SF3B and Y35 in PHF5A. The 12-membered ring core of 1 adopts a conformation that is held into its pocket by hydrogen bonding interactions between R1047 (with the C1 carbony) and K1071 (to the C3 OH) of SF3B and R38 of PHF4A (to C29 acetate carbonyl).

The importance of this class of splice modulators is now well recognized through enormous synthetic effort towards the pladienolides/FD-895, FR901463-5 analogs, spliceostatins including FR901464, meayamycin, thailanstatin A, and herboxidiene that united through a remarkable breath of chemical biological efforts has resulted in a consensus motif whose activity is defined by its targeting a unique pocket in the core SF3B complex of the spliceosome.

While recognized since their first discovery, the high potency and tumor cell selectivity of these analogs has ultimately lead to the entry of two Phase I clinical trials on semi-synthetic analogs E7107 and H3B-8800. While both trials have failed, these studies have continue to motivate medicinal chemical efforts to tune the metabolic stability and splice modulatory activity with the ultimate goal of realizing active analogs that can serve either as primary therapeutics or be used as the active agents in antibody drug conjugates. To this end, our laboratory has established a modular platform that enables programmable access to the 12-membered macrolide FD-895/pladienolide class ultimately resulting in 17S-FD-895 as a metabolically-improved analog which circumvents spontaneous cyclization that plagues the activity of the pladienolides that lack the C21 methoxy-group.

While recognized since their first discovery, the high potency and tumor cell selectivity of these analogs has ultimately lead to the entry of two Phase I clinical trials on semi-synthetic analogs E7107 in 2007 and H3B-8800 in 2016. While both trials have failed, these studies have continue to motivate medicinal chemical efforts to tune the metabolic stability and splice modulatory activity with the ultimate goal of realizing active analogs that can serve either as primary therapeutics or be used as the active agents in antibody drug conjugates or synergistic agents.

In 2012, we reported the total synthesis of FD-895 (1) along with its three C16-C17 isomers including 17S-FD-895 (1d, FIG. 2). In this study, we were able to systematically identify differential activity within each of the four C16-C17 analogues, and discovered an increased stability and activity of 1d. Ultimately, this led to the completion of an IND-enabling gram scale production of 1d and associated in vitro and in vivo pharmacological evaluation. During this study, we were able to begin exploring the SAR within these materials by extending methods to prepare isomeric materials at C3 (1a) and C7 (1d). Using this route, we began by adapting routes to prepare analogs of FD-895 (1) with inversion of the stereochemistry at 10 of the 11 stereocenters (C3, C7, C10, C11, C16, C17, C18, C19, C20 and C21).

Our synthetic approach (FIGS. 3-13) developed through the Stille coupling of macrolide core (C1-C11) and side chain (from C12-C28) components. Isomers with inversion at C3 (FIGS. 4 and 10), C7 (FIGS. 5 and 11), or C10, C11 (FIG. 6) were prepared by synthesis of the corresponding isomeric macrolide core and coupling it to a desired side chain in a final step. Side chain analogs at C17, C18, C19, C20, C21 were prepared in an analogous manner (FIGS. 7 to 13). This along with methylation at C17 enabled the preparation the set of 11 analogues 1a-1i (FIG. 2).

With milligram quantities of 1a-1i at hand, we began our studies to evaluate the relative efficacy of each analogue using cell growth inhibition studies in HCT116 colorectal carcinoma cells. As reported in FIG. 3, $GI_{50}$ values were collected for each analog after a 72 h treatment using the MTS cell viability assay (Table 12). Under these conditions, the natural FD-895 (1), 3S-FD-895 (1a) 17S-FD-895 (1d), 17-methoxy-FD-895 (1e) provided activities of <10 nM. Indicating that functionalization or stereochemical inversion at C17 and stereochemical inversion at C3 were not critical to their cell growth inhibitory activity. While tolerated, double modifications such as methylation and inversion in 17-methoxy-17S-FD-895 (1f) were accompanied by a 10 fold loss in activity, suggesting that only modest modifications are tolerated at these positions.

Figure 14:
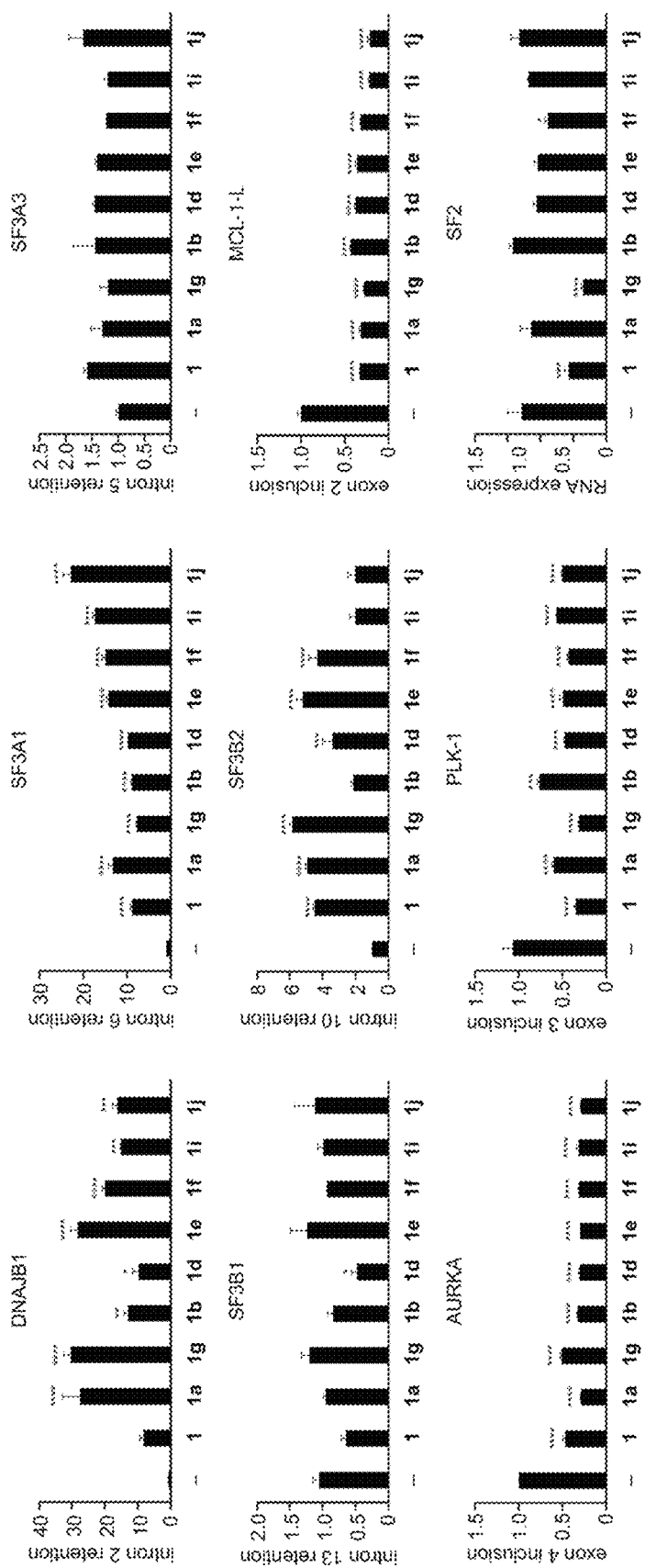
FIG. 14 shows structure-splicing profiles for RNA splice modulators after 4 treatment.

FIG. 14 shows structure-splicing profiles for RNA splice modulators after 4 treatment. HCT116 tumor cells were treated with each analogue at 20 times the G150 value (Table 12) for 4 hours and then cellular RNA was isolated and purified for qPCR. Primers were designed to evaluate intron retention or exon skipping, direct responses to splice modulator treatment. Genes evaluated included those involved in splicing regulation (SF3A1, SF3A3, SF3B1, SF3B2), apoptosis (MCL-1L), protein folding (DNAJB1), and cell cycle regulation (AURKA, PLK-1) relative to the unspliced control GAPDH. For alternative splicing regulator (SF2), primers were designed to evaluate gene expression, which changes in response splice modulator treatment for SF2 relative to the unspliced control GAPDH. (–) denotes untreated cells.

Figure 15:
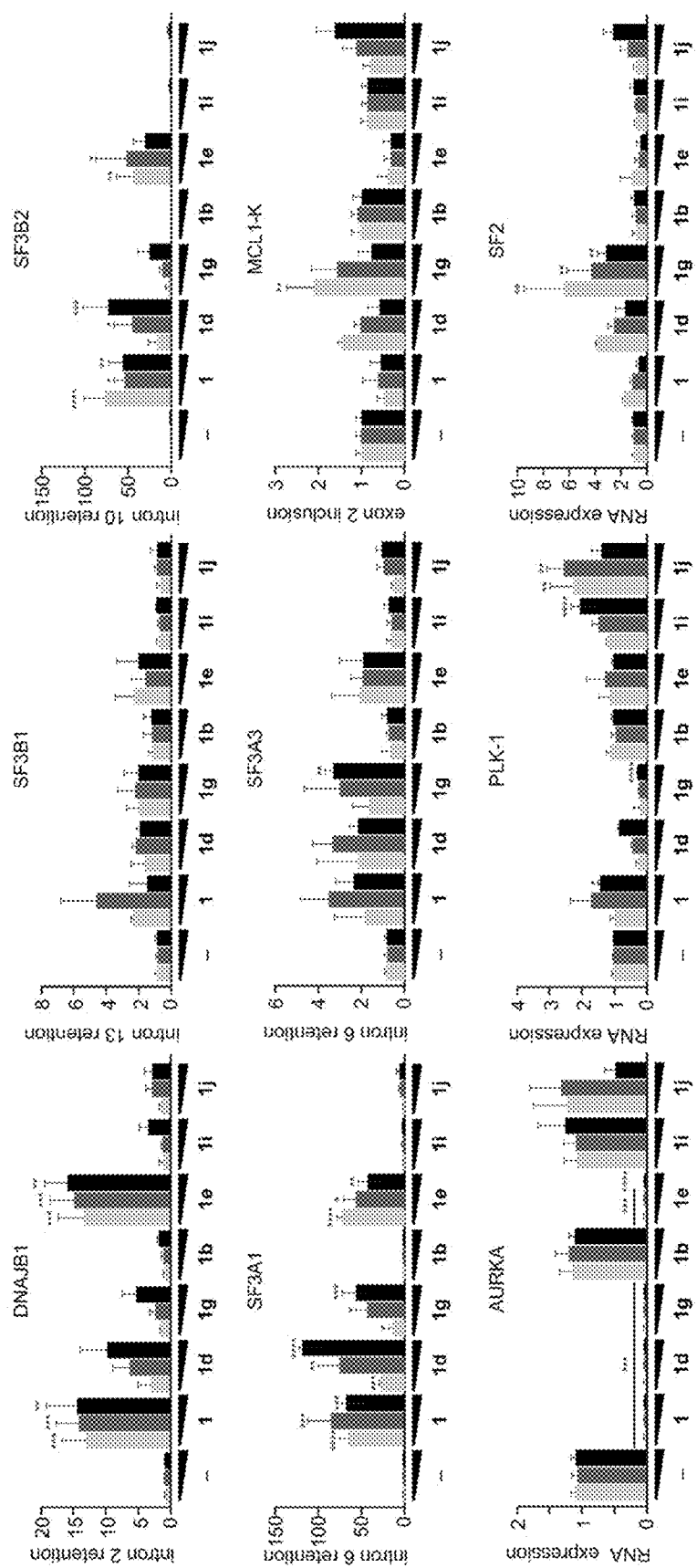
FIG. 15 shows structure-splicing profiles for RNA splice modulators after 24 h treatment.

FIG. 15 shows structure-splicing profiles for RNA splice modulators after 24 h treatment. HCT116 tumor cells were treated with analogues at 100 nM (light grey), 250 nM (grey), or 500 nM (black) for 24 h and then cellular RNA was isolated and purified for qPCR. Primers were designed to evaluate intron retention or exon skipping, direct responses to splice modulator treatment. Genes evaluated included those involved in splicing regulation (SF3A1, SF3A3, SF3B1, SF3B2), apoptosis (MCL-1L), and protein folding (DNAJB1), relative to the unspliced control GAPDH. For alternative splicing regulator (SF2), primers were designed to evaluate gene expression, which changes in response splice modulator treatment for SF2 relative to the unspliced control GAPDH. (—) denotes untreated cells.

This data also highlighted the importance of the C7 position as 7R-FD-895 (1b) was 250 fold less active than 1. Even more pronounced was loss from inversion at C10, C11 as 10R,11R-FD-895 (1c) had a $GI_{50}$ value of 37 μM. Methylation at C17 was tolerated illustrated by 17-methoxy-FD-895 (1e) and 17-methoxy-17S-FD-895 (1f) whose $GI_{50}$ values were 2.2 nM and 38 nM, respectively. Interestingly the combination of inversion and methylation at C17 in 1f was apparently less tolerated than direct methylation in 1e. Double modifications in general were less tolerated further illustrated by 3S,17S-FD-895 (1g) and 7R,17S-FD-895 (1h) whose $GI_{50}$ values of 130 nM and 806 nM, respectively, were 60 fold less effective for 1g when compared to 1a or 1d or 1.8 or 380 fold less effective for 1h when compared to 1b or 1d, respectively. Comparable losses of activity were also observed in modifications within the side chain as 17S,18S, 19S-FD-895 (1i) and 17S,20S,21R-FD-895 (1j) displayed G150 values of 450 and 260 nM, respectively. Here, we learned that inversion of the epoxide in 1i or inversion of the two stereocenters at C20 and C21 in 1j also contributed to a loss of activity when compared to 1d. The fact that multiple modifications were present in 1i and 1j likely contributed to the level of activity loss.

Next, we turned our efforts to explore the ability of these analogues to modulate splicing. For these studies, we selected the analogs that displayed $GI_{50}$ values ≤500 nM. Here, we treated HCT116 cells with 1, 1a, 1b, 1d-g, 1i, and 1j at 20 times the $GI_{50}$ value for each analog (namely, 34 nM 1, 44 nM 1a, 8.6 μM 1b, 42 nM 1d, 44 nM 1e, 750 nM 1f, 2.6 μM 1g, 9 μM 1i and 5.6 μM 1j) allowing us to normalize each analog relative to each other and thereby evaluate changes in gene response due to splicing selectivity rather than compounding effects due to differences in potency. We treated cells for 4 h so that we could evaluate early changes in splicing activity, and then cellular RNA was isolated and purified for analyses by qPCR (FIG. 14). Most importantly, none of the concentrations tested led to significant changes in cell viability, ensuring that changes in gene expression were not due to cell death.

For these studies, we evaluated the expression of genes involved in splicing regulation (SF3A1, SF3A3, SF3B1, SF3B2), apoptosis (MCL-1L), protein folding (DNAJB1), and cell cycle regulation (AURKA, PLK-1) relative to the unspliced control GAPDH. Primers were designed to evaluate intron retention or exon skipping, direct responses to splice modulator treatment. The master splicing regulator alternative splicing factor (SF2) was also evaluated, with the primers for this gene designed to evaluate overall gene expression, which changes in response to splice modulator treatment.

As shown in FIG. 14, few if any clear trends can be obtained as each analog displayed an individualize efficacy against each pre-mRNA. While some genes such as SF3A3 or SF3B1 showed modest intron retention (levels of intron retention <3), as well as differentiation over the analogue panel, other such as DNAJB1, SF3A1 and SF3B2 displayed significant efficacy (level of intron retention >3). For DNAJB1, compounds 1a (at 44 nM), 1g (at 2.6 µM) and 1e (at 44 nM) provided the highest level of intron retention, indicating that inversion at C3 in 1a and 1g and methylation at C17 in 1e played a beneficial role in enhancing DNAJB1 intron 2 retention as compared to 1 (at 34 nM). For the splicing factor SF3A1, 1a (at 44 nM), 1e (at 44 nM), 1f (at 750 nM), 1i (at 9 µM), and 1j (at 5.6 µM) were more effective than 1 (at 34 nM), further confirming the ability of C3 and C17 methylation as a tool to increase efficacy against this gene. While higher concentrations were required, this study also showed that side chain modifications can also lead to comparable intron retention, as illustrated here the effects of 1i and 1j on intron 6 retention in SF3A1.

Analogue selectivity was also observed in the other splicing factors explored including SF3B1, and SF3B2. While only modest selectivity was observed for SF3A3 (as illustrated by the comparison of 1a, 1b or 1d to 1) or SF3B1 as illustrated by the comparison of 1b or 1d to 1), statistically-relevant selectivity was observed for SF3B2 indicating improved efficacy for 1b (at 8.6 µM), 1d (at 42 nM), 1i (at 9 µM), and 1j (at 5.6 µM) as compared to 1 (at 34 nM). While all of the data obtained in FIG. 4 was collected from the same cells (each compound was applied to the same cell culture individually and intron retention, exon skipping and relative RNA expression data was collected from the same sample) the efficacy of each analog was different for each gene differed as best illustrated by comparing the effects on DNAJB1, SF3A1 and SF3B2.

In addition to exon skipping, we also confirmed the ability of these analogues to induce exon skipping as illustrated by exon 2 in MCL-1L, exon for in AURKA and exon 3 in PLK-1. While the levels of exon skipping was comparable for reach analog in MCL-1-L, analogue 1g (at 2.6 µM) and 1 (at 34 nM) displayed the most potent effect on exon 3 inclusion in PLK-1, while 1a (at 44 nM) displayed the most potent effect on exon 4 skipping in AURKA, again furthering the fact that inversion at C3 or C17 suggests utility at tuning selectivity towards specific genes. This was further supported by the fact that 1g (at 2.6 µM) and 1 (at 34 nM) also displayed the highest efficacy in down regulating the expression of SF2 RNA.

From this 4 h study (FIG. 14), a small set of analogs (1, 1b, 1g, 1d, 1e, 1i and 1j) were selected to evaluate if effects on splicing when presented for a longer 24 h period. While our prior data suggested that 4 h treatment was sufficient for responses in many tumor cell lines, we wanted to fully evaluate if time would play a role within our analogue set. Using identical procedures as that used for 4 h, HCT116 cells were treated with three concentrations (100 nM, 250 nM and 500 nM) of each analog for 24 h. Multiple concentrations were used as a means to check further validate the use of the $GI_{50}$ concentration in our prior study (FIG. 14). As before, none of the concentrations tested led to significant changes in cell viability over the 24-hour time window, ensuring that changes in gene expression were not due to cell death.

Figure 5A:
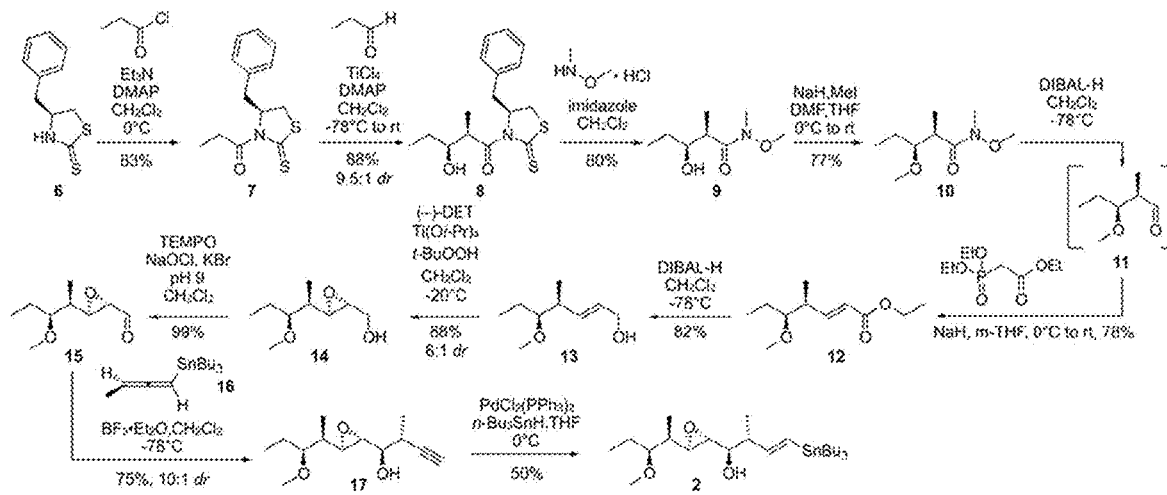
FIGS. 5A to 5C show synthetic scheme of compound 1b (7R-FD-895) in FIG. 2.
Figure 5B:
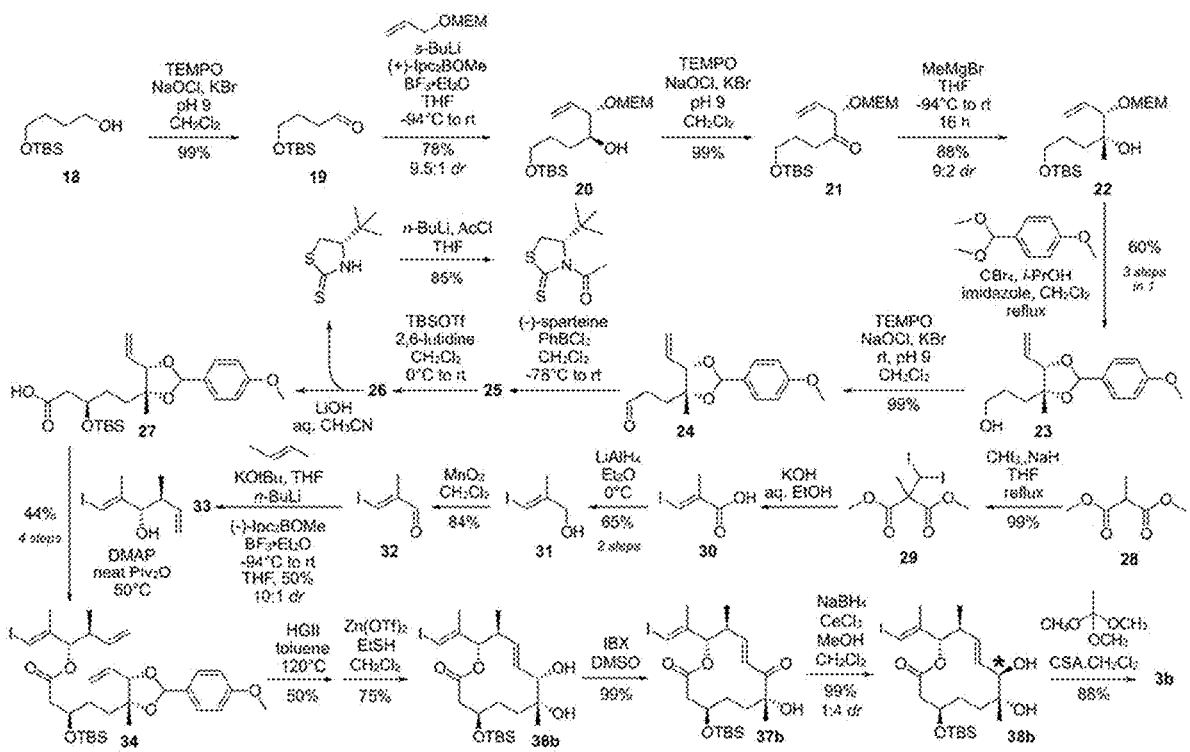
Figure 5C:
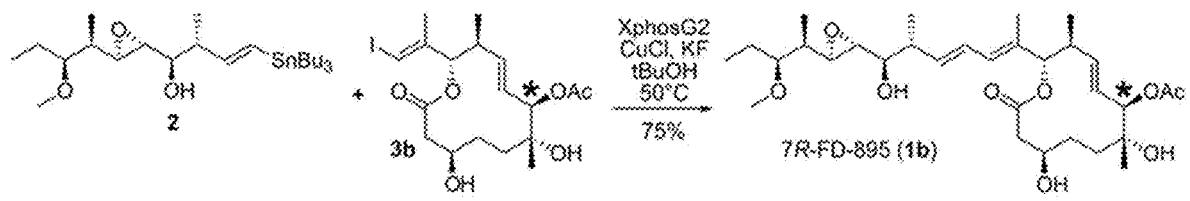

We found that splicing activity typically corresponded to growth inhibitor activity for each analog (FIG. 2), with the caveat that each analog displayed a unique gene-selective signature (FIG. 5). The natural product FD-895 (1), a potent cell growth inhibitor, altered the splicing of many of the genes tested, including DNAJB1, SF3B2, SF3A1, AURKA and PLK-1. Epimerization of the C17 center given by 1d (a comparable inhibitor of cell growth as 1) led to a modest switch in gene selectivity with decreased level of intron retention in DNAJB1, a concentration dependent increased intron retention of SF3B2 and SF3A1, and decreased effect at reducing PLK-1 and SF2 RNA expression when compared to 1.

Further epimerization of C3 in 17S-FD-895 (1d) led to 1g with 75 fold loss in cell growth inhibitor when compared to 1 (FIG. 15). While 1g displayed the expected loss in intron retention of DNAB1, SF3B2, SF3A1 and reduced ability to inhibit SF2 RNA expression, it was the only analog that displayed a concentration dependent increase intron retention of SF3A3 and reduced PLK-1 RNA expression. In addition, 1g induced intron retention of SF3A1 and altered the expression of AURKA comparable to 1.

Not all analogues provided productive splice modulatory activity. As illustrated in FIG. 5, epimerization at C7 in 1b ($GI_{50}$ value was 250 fold less than 1) displayed a loss of splicing activity when compared to 1. In contrast, side chain modified 17S,18S,19i-FD895 (11) showed a drastic reduction in splicing activity, correlating with its decrease in cell growth inhibitory activity, for all genes tested except for PLK-1, for which 11 increased the RNA expression relative to negative controls. Comparably, 17S,20S,21R-FD-895 (1j) provided a splicing profile comparable to 1i with the exception of its activity at reducing the expression of AURKA at 500 nM. Finally, methylation as noted in 1e, which had comparable cell growth inhibitor activity as 1, was found have comparable or slightly reduced splice modulatory activity as 1, as best illustrated by its effects on DNAJB1, AURKA, and SF3A1.

RNA splice modulation through inhibition of the SF3B complex provides a complex response whose structure activity relationships are accompanied not only by inhibition of activity in their ability to terminate cell growth, but rather, includes a discrete change in activity towards specific genes. While far from comprehensive, this study illustrated the unique ability of stereochemical changes within FD-895 to modulate intron retention, exon skipping and overall RNA expression within specific genes. These studies not only provide an important next step in understanding the unique medicinal chemical aspects of splice modulation, but also and perhaps most importantly, illustrate how inversion of single or sets of stereocenters do not only lead to a binary change in activity for a material, but more importantly, suggest the further potential to mechanistically tune a material by guiding its ability to enhance splice modulation of specific genes. Outside modifications at C7 in 1b and C10, C11 in 1c, stereochemical inversion within the core in 1a, side chain in 1d, 1i or 1j or both in 1e, were not only tolerated but also served to modulate their splice activity in a gene selective manner. Studies are now underway to understand the role of these stereochemical inversions on the three dimensional structure of 1.

Example 3: Synthesis of Optically-Pure FD-895 Diastereomers

A. General Experimental Methods

Chemical reagents were obtained from Acros Organics, Alfa Aesar, Chem-Impex Int., CreoSalus, Fischer Scientific, Fluka, Oakwood Chemical, Sigma-Aldrich, Spectrum Chemical Mfg. Corp., or TCI Chemicals. Deuterated NMR solvents were obtained from Cambridge Isotope Laboratories. All oligonucleotides were purchased by custom synthesis (Integrated DNA Technologies). All reactions were conducted with rigorously dried anhydrous solvents that were obtained by passing through a column composed of activated A1 alumina or purchased as anhydrous. Anhydrous N,N-dimethylformamide was obtained by passage over activated 3 Å molecular sieves and a subsequent NaOCN column to remove traces of dimethylamine. Triethylamine (Et$_3$N) was dried over Na and freshly distilled. Ethyl-N,N-diisopropylamine (EtNi-Pr$_2$) was distilled from ninhydrin, then from KOH. Anhydrous CH$_3$CN was obtained by distillation from CaH$_2$. All reactions were performed under positive pressure of Ar in oven-dried glassware sealed with septa, with stirring from a Teflon coated stir bars using an IKAMAG RCT-basic stirrer (IKA GmbH). Solutions were heated on adapters for IKAMAG RCT-basic stirrers. Analytical Thin Layer Chromatography (TLC) was performed on Silica Gel 60 F254 precoated glass plates (EM Sciences). Preparative TLC (pTLC) was conducted on Silica Gel 60 plates (EM Sciences). Visualization was achieved with UV light and/or an appropriate stain (12 on SiO$_2$, KMnO$_4$, bromocresol green, dinitrophenylhydrazine, ninhydrin, and ceric ammonium molybdate). Flash chromatography was carried out on Fischer Scientific Silica Gel, 230-400 mesh, grade 60 or SiliaFlash Irregular Silica Gel P60, 40-63 µm mesh, grade 60. Yields correspond to isolated, chromatographically and spectroscopically homogeneous materials. $^1$H NMR and $^{13}$C NMR spectra were recorded on a Varian VX500 spectrometer equipped with an Xsens Cold probe. Chemical shift δ values for $^1$H and $^{13}$C spectra are reported in parts per million (ppm) and multiplicities are abbreviated as s=singlet, d=doublet, t=triplet, q=quartet, m=multiplet, br=broad. All $^{13}$C NMR spectra were recorded with complete proton decoupling. FID files were processed using Mestrallova 12.0.3. (MestreLab Research). Electrospray (ESI) mass spectrometric analyses were performed using a ThermoFinnigan LCQ Deca spectrometer, and high-resolution analyses were conducted using a ThermoFinnigan MAT900XL mass spectrometer with electron impact (EI) ionization. A Thermo Scientific LTQ Orbitrap XL mass spectrometer was used for high-resolution electrospray ionization mass spectrometry analysis (HR–ESI-MS). FTIR spectra were obtained on a Nicolet magna 550 series II spectrometer as thin films on either KBr or NaCl discs, and peaks are reported in wavenumbers (cm$^{-1}$). Optical rotations [α]$_D$ were measured using a Perkin-Elmer Model 241 polarimeter with the specified solvent and concentration and are quoted in units of deg cm$^2$ g$^{-1}$. Spectral data and procedures are provided for all new compounds and copies of select spectra have been provided.

B. Synthesis of FD-895 (1)

Figure 3A:
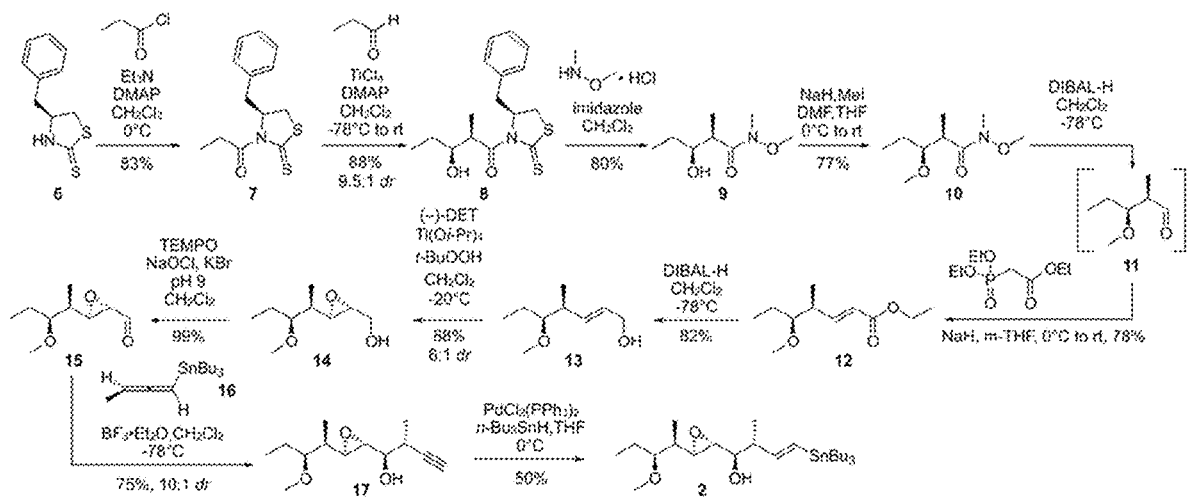
FIGS. 3A to 3C show synthetic scheme of compound 1 (FD-895) in FIG. 2.
Figure 3B:
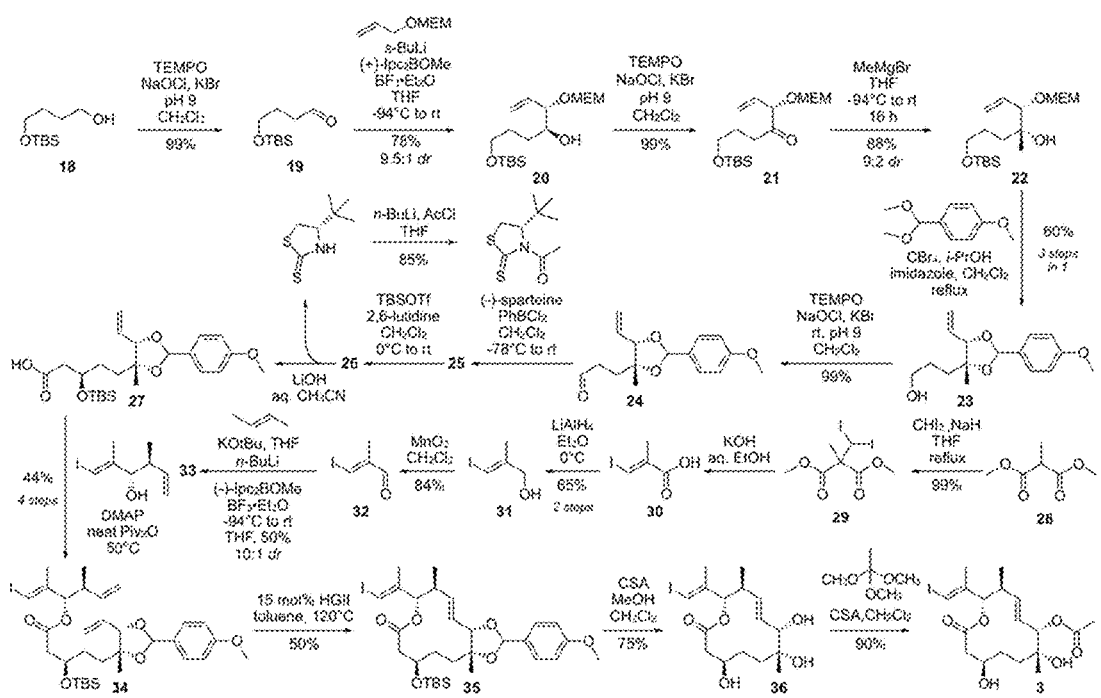
Figure 3C:
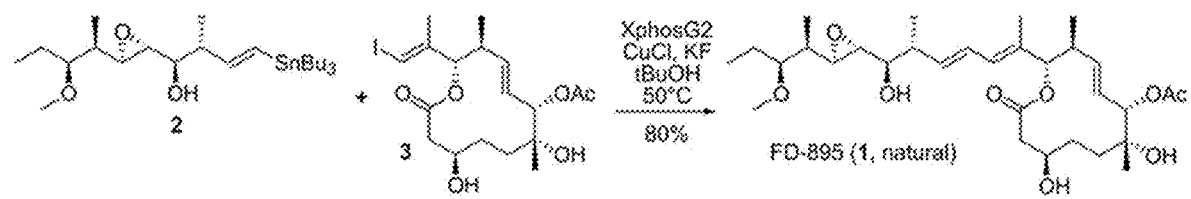

Synthesis of FD-895 (1) is shown in FIGS. 3A through 3C. The synthesis of FD-895 (1) was reported (Villa et al., Org. Lett. 14, 5396-5399). For this study, it was prepared from compounds 15, 16, and 3 (Chan et al., Cell Reports Physical Science 1, 100277). Updated procedures are provided for these steps.

Marshall Addition of Allenylstannane 16 to Aldehyde 15 to Afford Alkyne 17

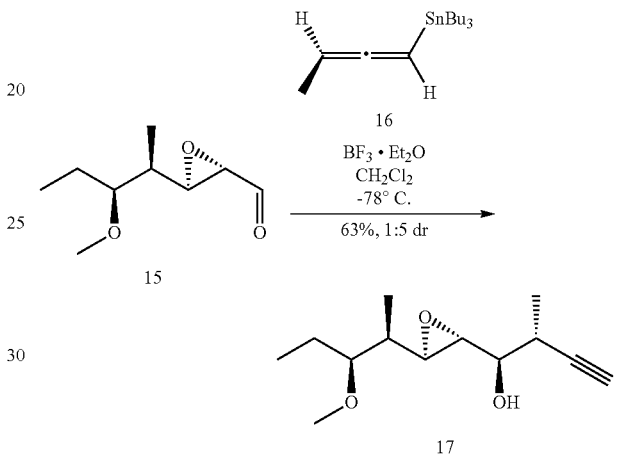

Reagents:
BF$_3$·Et$_2$O, 46.5% BF$_3$ (Alfa Aesar): used without further purification (1R,2R)-1-((2R,3R)-3-((2R,3S)-3-Methoxypentan-2-yl) oxiran-2-yl)-2-methylbut-3-yn-1-ol (5). Aldehyde 15 (0.701 g, 4.08 mmol) and allenylstannane 16 (2.10 g, 6.10 mmol) in a 100 mL flask were dissolved in anhydrous CH$_2$Cl$_2$ (40.0 mL) and purged with an Ar atmosphere. The mixture was cooled to −78° C. and BF$_3$·Et$_2$O (0.753 mL, 6.10 mmol) was added dropwise over 5 min. The reaction was stirred for 1 h at −78° C. A mixture of MeOH (5 mL) and satd. NaHCO$_3$ (1 mL) was added, and the solution was warmed to rt. The phases were separated, and the aqueous phases were extracted with Et$_2$O (3×100 mL). The organic phases were combined, dried with Na$_2$SO$_4$ and concentrated on a rotary evaporator. Alkyne 17 (0.692 g, 63%) was obtained in a 1:5 mixture of diastereomers (by NMR) as a colorless oil by flash chromatography, eluting with a gradient of hexanes to 1:3 Et$_2$O/hexanes.

Note 1: Desired Diastereomer was Isolated in the Next Step.

Note 2: The remaining C18-C19 epoxide diastereomer from the Sharpless epoxidation was resolved after purification of the next step.

Alkyne 17: TLC (2:1 hexanes/EtOAc): R$_f$=0.50; $^1$H NMR (CDCl$_3$, 400 MHz) δ 3.55 (s, 3H), 3.41 (m, 1H), 3.21 (ddd, J=10.4, 6.4, 3.9 Hz, 1H), 3.07 (dd, J=4.6, 2.3 Hz, 1H), 3.0 (dd, J=8.1, 2.2 Hz, 1H), 2.67 (m, 1H), 2.16 (d, J=2.5 Hz, 1H), 2.07 (b s, 1H), 1.57 (m, 3H), 1.31 (d, J=6.9 Hz, 3H), 0.97 (d, J=7.0 Hz, 3H), 0.90 (t, J=7.4 Hz, 3H); $^{13}$C NMR (CDCl$_3$, 100 MHz) δ 83.8, 77.4, 73.7, 71.2, 59.5, 59.4, 58.3, 39.0, 31.1, 23.9, 17.2, 10.4, 10.2; ESI-MS m/z 249.14

[M+Na]+; FTIR (film) vmax 3430, 3310, 2967, 2935, 2878, 1457, 1379, 1260, 1093 cm⁻¹; HR–ESI–MS m/z calcd. for $C_{13}H_{22}O_3Na$ [M+Na]+: 249.1461, found 249.1462. $[\alpha]^{25}_D$=+10.2° (c=1.0, $CH_2Cl_2$).

Hydrostannylation of Alkyne 17

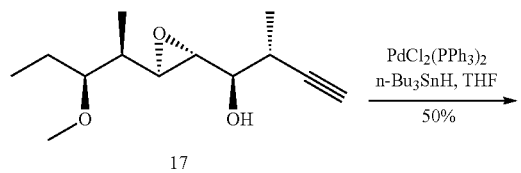

Reagents:
- n-Bu₃SnH, 97% contains 0.05% BHT as stabilizer (Acros Organics): used without further purification
- PdCl₂(PPh₃)₂ (Oakwood Chemical): dried via azeotropic distillation of benzene (1R,2R,E)-1-((2R,3R)-3-((2R,3S)-3-Methoxypentan-2-yl)oxiran-2-yl)-2-methyl-4-(tributylstannyl)but-3-en-1-ol (2). PdCl₂(PPh₃)₂ (0.155 g, 0.221 mmol) was added to a solution of alkyne 17 (0.501 g, 2.21 mmol) in a 50 mL flask in anhydrous THF (20 mL). The mixture was cooled to 0° C. and n-Bu₃SnH (1.79 mL, 6.63 mmol) was added dropwise. The mixture was stirred for 45 min at 0° C., at which point the resulting mixture was concentrated to yield a black crude oil. The material was extracted into hexanes, filtered through a pad of Celite and was eluted with hexanes. The eluant was concentrated on a rotary evaporator, and this process was repeated twice until a clear black solution was achieved. Pure vinylstannane 2 (0.110 g, 50%) was obtained as a mixture of 1:5 α:β regioisomers by flash chromatography, eluting with a gradient of hexanes to $CH_2Cl_2$ to 1:20 $Et_2O/CH_2Cl_2$. The desired regioisomer and diastereomer can be obtained in 95+% purity by additional flash chromatography, eluting with a gradient of hexanes to $CH_2Cl_2$ to 1:20 $Et_2O/CH_2Cl_2$.

Note 1: Unwanted Diastereomer Obtained from Previous Reaction was Removed after Flash Chromatography Vinylstannane 2: TLC (10:1 hexanes/Et₂O): $R_f$=0.28 (CAM stain); ¹H NMR (C₆D₆, 500 MHz) δ 6.20 (m, 2H), 6.19 (d, J=6.8 Hz, 1H), 3.34 (td, J=4.9, 1.8 Hz, 1H), 3.23 (s, 3H), 3.16 (td, J=6.3, 4.2 Hz, 1H), 2.98 (dd, J=8.0, 2.3 Hz, 1H), 2.84 (dd, J=4.3, 2.3 Hz, 1H), 2.51 (td, J=6.9, 5.2 Hz, 1H), 1.61 (m, 6H), 1.48-1.32 (m, 7H), 1.19 (d, J=6.9 Hz, 3H), 1.02-0.92 (m, 19H), 0.86 (t, J=7.4 Hz, 3H); ¹³C NMR (C₆D₆, 500 MHz) δ 154.5, 150.5, 150.4, 150.4, 150.3, 83.8, 83.3, 72.8, 59.0, 57.5, 57.3, 57.2, 39.0, 39.0, 29.3, 27.4, 23.5, 15.9, 15.8, 13.4, 10.5, 9.6, 9.4; HR–ESI–MS m/z calcd. for $C_9H_{17}O_3$[M+H]+519.2843, found 519.2839; $[\alpha]^{25}_D$=−2.3° (c=1.0, $CH_2Cl_2$).

Stille Coupling of Stannane 2 and Core 3

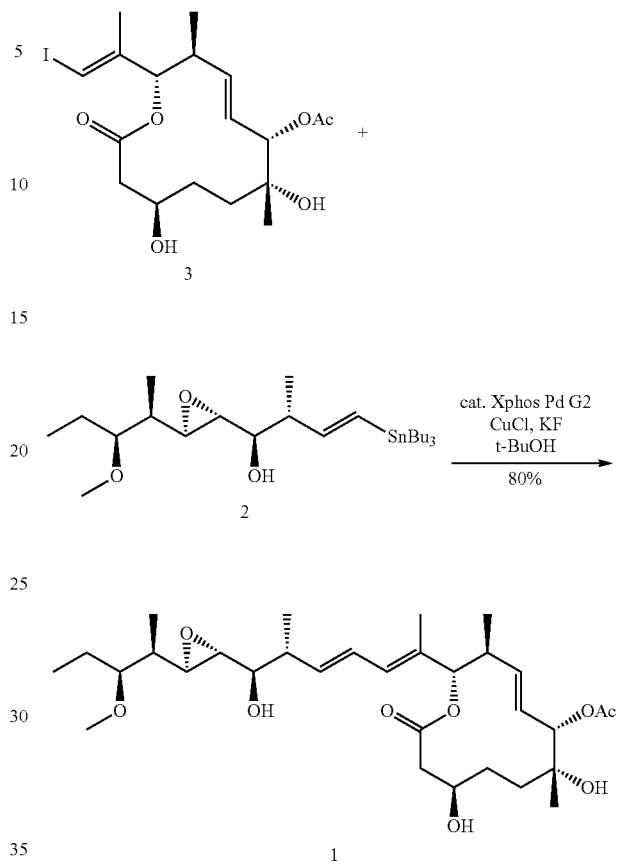

Reagents:
- CuCl, anhydrous, beads, 99.99% (Sigma-Aldrich): beads were powdered prior to addition
- KF, anhydrous, powder, 99.9% (Sigma-Aldrich): used without further purification
- XPhos Pd G2 (Sigma-Aldrich): used without further purification
- t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The eluants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

FD-895 (1): Yield: 80%, 121 mg; TLC (1:3 acetone/$CH_2Cl_2$): $R_f$=0.28 (CAM stain); NMR data provided in Table S1; FTIR (film) $v_{max}$ 3447, 2963, 2930, 2875, 1739, 1457, 1374, 1239, 1176, 1089, 1021 cm⁻¹; HR–ESI–MS m/z calcd. for $C_{31}H_{50}IO_9Na$ [M+Na]+: 589.3370, found 589.3376; $[\alpha]^{25}_D$=+6.8° (c=1.0, $CH_2Cl_2$).

TABLE 1

| | | | NMR data for FD-895 (1) in $C_6D_6$ | | |
|---|---|---|---|---|---|
| Position | $\delta_H$, mult (J in Hz) | $\delta_C$ | $^1$H, $^1$H-COSY | $^1$H, $^1$H-NOESY | $^1$H, $^{13}$C-HMBC |
| 1 | | 172.1 | | | |
| 2' | 2.30, dd (14.8, 3.9) | 38.6 | 2"w, 3 | 2", 3 | 1, 3, 4 |
| 2" | 2.20, dd (14.8, 3.0) | | 2', 3 | 2', 3, 4', 5' | 1, 3w |
| 3 | 3.51, m | 69.4 | 3OHw | 2', 2", 4', 5', 5", 6OH, | |
| 3-OH | 3.66, d (11.0) | | 3 | 3, 6OH, 17OH | |
| 4' | 1.60, m | 30.4 | 3w, 4", 5' | 2', 3, 8, 24 | 3, 5 |
| 4" | 1.25, m | | 3, 5' | 3w, 5', 7 | 3, 5 |
| 5' | 1.54, m | 35.9 | 5" | 2", 3, 5', 8 | 4, 6, 24w |
| 5" | 1.23, m | | 4' | 3, 4', 7 | 4, 6, 7, 24w |
| 6 | | 73.3 | | | |
| 6-OH | 1.85, s | | | 3, 3OH, 17OH | |
| 7 | 5.26, s | 79.2 | 8 | 4", 5", 8, 24 | 8, 9, 24, 26, 29 |
| 8 | 5.83, dd (15.2, 9.8) | 126.5 | 7, 9 | 4'w, 5', 7, 9, 10 | 6w, 9, 10 |
| 9 | 5.63, dd (15.2, 10.0) | 140.7 | 8, 10 | 4", 5", 7, 8, 10, 11, 25 | 7, 8, 10, 11w, |
| 10 | 2.38, m | 41.1 | 11, 25 | 7, 8, 9, 11w, 25, 26 | 8, 9, 11, 25 |
| 11 | 5.24, d (1.8) | 82.6 | 10 | 9, 10w, 13, 25, 26w | 1, 9, 10, 12, |
| 12 | | 131.6 | | | |
| 13 | 6.10, dd (10.9, 1.5) | 131.7 | 14, 26 | 11, 14, 15, 25, 26w, 28w | 11, 14, 15, 26 |
| 14 | 6.23, dd (15.0, 10.8) | 126.2 | 13, 15 | 13, 15, 16, 26, 27 | 12, 13, 16 |
| 15 | 5.53, dd (15.0, 8.7) | 138.3 | 14, 16 | 13, 14, 16, 17, 18, 27 | 13, 14, 16, 17, |
| 16 | 2.39, m | 42.6 | 17, 27 | 14, 15, 17, 18, 27 | 13w, 14, 15, |
| 17 | 3.10, m | 75.3 | 16, 18 | 15, 16, 18, 19, 27 | 16w, 27w |
| 17-OH | 2.14, bs | | 17 | 3w, 3OH, 6OH, 17w | |
| 18 | 2.66, dd (5.8, 2.2) | 60.6 | 17, 19 | 15w, 16, 17, 20, 27, 28 | 17, 20 |
| 19 | 2.87, dd (8.3, 2.3) | 59.7 | 18w, 20 | 17, 20, 21, 28, 31 | 17, 20, 21, 28 |
| 20 | 1.26, m | 39.4 | 19, 28 | 18, 19, 21, 23, 28 | 18, 19, 21, 23, |
| 21 | 3.15, td (6.4, 4.1) | 83.6 | 20, 22', 22" | 19, 20, 22', 22", 23, 28 | 19, 20, 22w, |
| 22' | 1.63, m | 23.9 | 22", 23 | 21, 22", 23 | 20, 21, 23 |
| 22" | 1.37, ddd (14.0, 7.6, | | 22', 23 | 21, 22', 23 | 20, 21, 23 |
| 23 | 0.84, t (7.5) | 10.0 | 22', 22" | 21, 22', 22" | 21, 22 |
| 24 | 1.02, s | 24.8 | | 4', 5', 6OH, 7 | 5, 6, 7 |
| 25 | 0.70, d (6.8) | 16.4 | 10 | 9, 10, 11, 13w, 26 | 9, 10, 11 |
| 26 | 1.57, d (1.3) | 11.9 | | 10, 11, 14, 25 | 11, 12, 13, 14, |
| 27 | 1.14, d (6.8) | 17.0 | 16 | 14, 15, 16, 17, 18w | 15, 16, 17 |
| 28 | 0.83, d (7.1) | 10.6 | 20 | 17, 18, 19, 21, 31w | 19, 20, 21 |
| 29 | | 169.0 | | | |
| 30 | 1.62, s | 20.7 | | | 29 |
| 31 | 3.25, s | 57.8 | | 19, 23 | 21 |

C. Synthesis of 3S-FD-895 (1a)

Figure 4A:
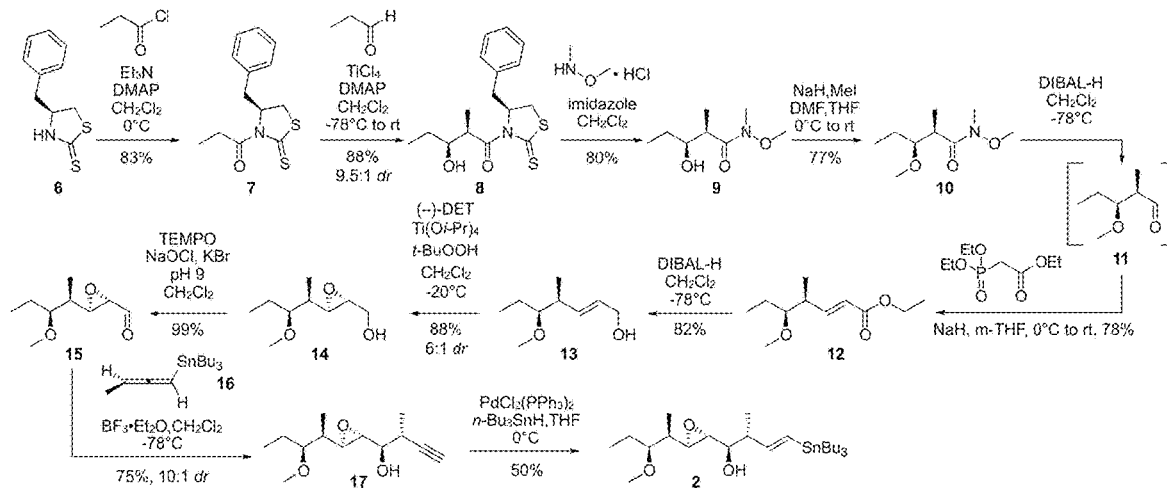
FIGS. 4A to 4C show synthetic scheme of compound 1a (3 S-FD-895) in FIG. 2.
Figure 4B:
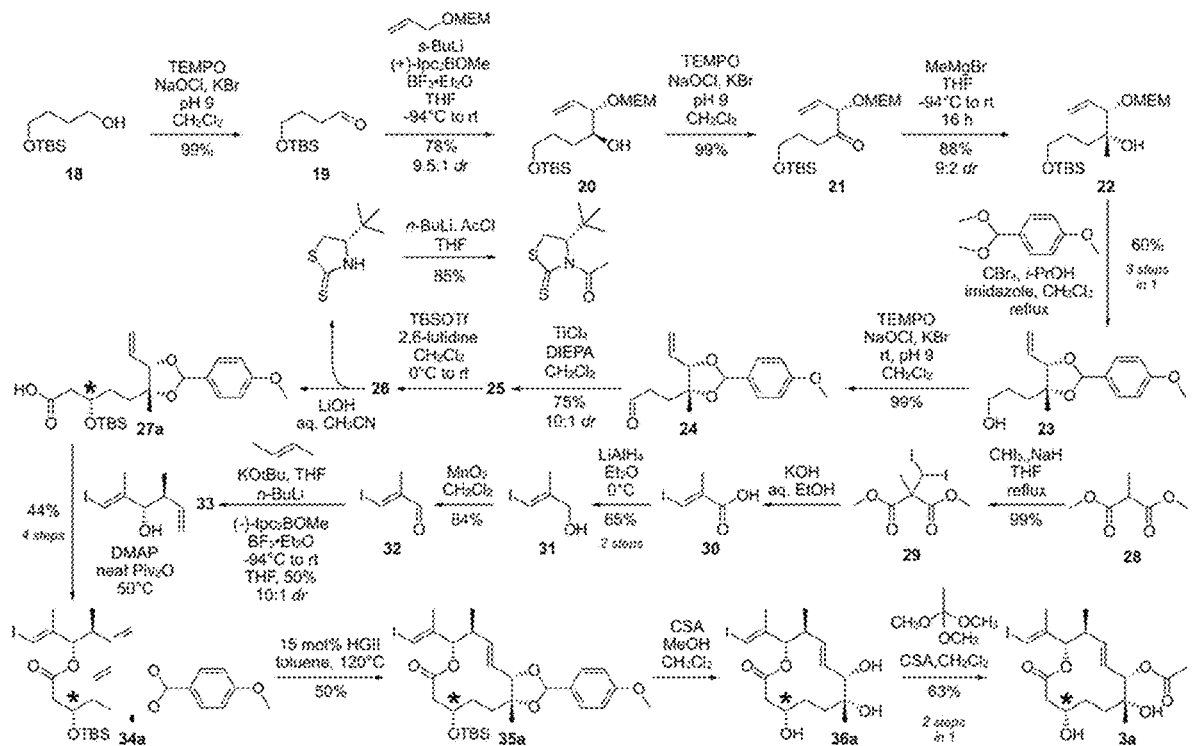
Figure 4C:
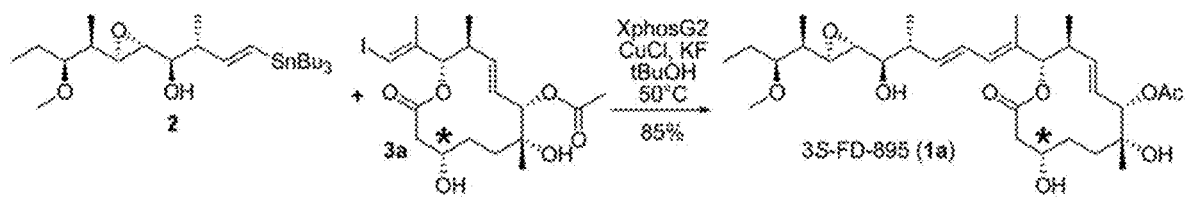

Synthesis of 3S-FD-895 (1a) is shown in FIGS. 4A through 4C. For this study, it was prepared from compounds 2 and 3a reported in Chan 2020. Updated procedures are provided for this step. Asterisks (*) denote the compounds that differ from that used to prepare FD-895 (1).

Stille Coupling of Stannane 2 and Core 3a

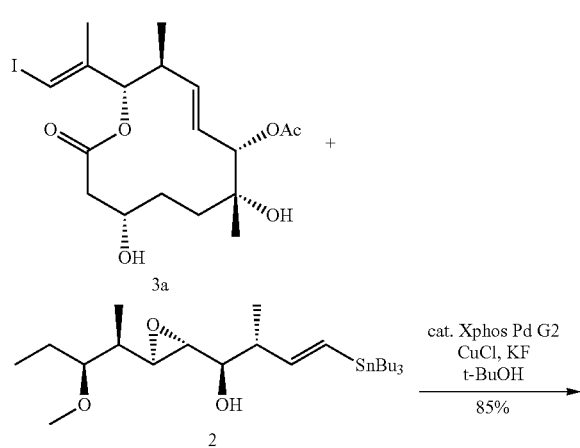

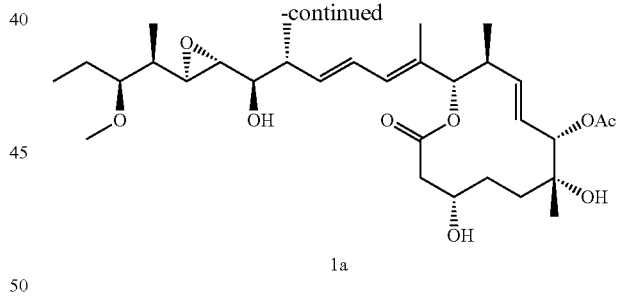

1a

Reagents:
- CuCl, anhydrous, beads, 99.99% (Sigma-Aldrich): beads were powdered prior to addition
- KF, anhydrous, powder, 99.9% (Sigma-Aldrich): used without further purification
- XPhos Pd G2 (Sigma-Aldrich): used without further purification
- t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The eluants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

3S-FD-895 (1a): Yield: 85%, 65.1 mg; TLC (1:3 acetone/$CH_2Cl_2$): $R_f$=0.18 (CAM stain); NMR data provided in Table S2; FTIR (film) $v_{max}$ 3447, 2963, 2930, 2875, 1739, 1457, 1374, 1239, 1176, 1089, 1021 $cm^{-1}$; HR–ESI–MS m/z calcd. for $C_{31}H_{50}IO_9Na$ $[M+Na]^+$: 589.3310, found 589.3311; $[\alpha]^{25}_D$=+9.4° (c=1.0, $CH_2Cl_2$).

TABLE 2

| | NMR data for 3S-FD-895 (1a) in $C_6D_6$ | | | | |
|---|---|---|---|---|---|
| Position | $\delta_H$, mult (J in Hz) | $\delta_C$ | $^1H$, $^1H$-COSY | $^1H$, $^1H$-NOSEY | $^1H$, $^{13}C$-HMBC |
| 1 | | 169.6 | | | |
| 2' | 2.47, m | 40.0 | 2", 3 | 3, 5' | 1, 3, 4w |
| 2" | 2.38, m | | 2', 3 | 3 | 1, 3, 4 |
| 3 | 4.25, bs | 67.3 | 2', 2"w | 2'w, 2", 4', 4" | |
| 3-OH | | | | | |
| 4' | 1.35, m | 27.5 | 3w, 4", 5" | 3, 5', 5", 7 | 2w, 3w, 5w |
| 4" | 1.33, m | | 3w, 4', 5' | 3, 5', 5" | 3w, 5w |
| 5' | 1.88, dt (13.5, 6.5) | 30.7 | 4", 5" | 4" | 4, 6, 24 |
| 5" | 1.82, m | | 4', 5' | 4', 24 | 4, 6, 7, 24 |
| 6 | | 73.4 | | | |
| 6-OH | | | | | |
| 7 | 5.26, d (9.8) | 79.3 | 8 | 4', 8, 9, 24 | 8, 9, 24w, |
| 8 | 5.93, dd (15.2, 9.8) | 126.6 | 7, 9, 10w | 5'w, 7, 9, 10 | 6w, 10 |
| 9 | 5.62, dd (15.3, 10.0) | 140.4 | 8, 10 | 7, 8, 10, 11, 25 | 7, 10, 11w, |
| 10 | 2.47, m | 41.2 | 9w, 11, 25 | 8w, 25 | 8, 9, 11, |
| 11 | 5.20, d (10.7) | 82.2 | 10 | 10w, 13, 25 | 1, 9, 10, 12, |
| 12 | | 132.1 | | | |
| 13 | 6.17, d (11.0) | 131.4 | 14, 26w | 8, 15, 27w | 11, 15, 26 |
| 14 | 6.26, dd (15.0, 10.9) | 126.3 | 13, 15 | 15, 27 | 12, 13, 16 |
| 15 | 5.54, dd (15.0, 8.7) | 137.9 | 14, 16 | 7, 13, 14, 16w, 27 | 12, 13, 16, |
| 16 | 2.38, m | 42.6 | 15, 17w, 27 | 14, 15, 27 | 14, 15, 17, |
| 17 | 3.10, t (6.6) | 75.2 | 16, 18 | 16w, 18w 27 | 15, 16, 18, |
| 17-OH | | | | | |
| 18 | 2.68, dd (5.8, 1.9) | 60.6 | 17, 19w | 17, 19, 20, 28 | 17, 19w, |
| 19 | 2.86, dd (8.2, 2.3) | 59.6 | 18w, 20 | 20w, 28 | 17w, 18w, |
| 20 | 1.27, ddd (8.2, 6.9, | 39.3 | 19, 28 | 18, 21, 22', 22", 28 | 19, 28w |
| 21 | 3.14, td (6.3, 4.1) | 83.5 | 20, 22', 22" | 20, 22', 22", 23, 28 | 19, 20w, |
| 22' | 1.63, m | 23.8 | 21, 22", 23 | 22", 23w | 20, 21, 23 |
| 22" | 1.39, m | | 21, 22', 23 | 22', 23 | 20, 21, 23 |
| 23 | 0.84, t (7.5) | 10.0 | 22', 22" | 21, 22', 22" | 21, 22 |
| 24 | 1.11, s | 24.8 | | 2" | 5, 6, 7 |
| 25 | 0.73, d (6.8) | 16.5 | 10 | 10 | 9, 10, 11 |
| 26 | 1.60, s | 11.9 | 13 | 10, 14 | 11, 12, 13 |
| 27 | 1.15, d (6.7) | 17.1 | 16 | 15, 16, 17 | 15, 16, 17 |
| 28 | 0.85, d (7.8) | 10.6 | 20 | 20, 21 | 19, 20 |
| 29 | | 169.1 | | | |
| 30 | 1.66, s | 20.8 | | | 29 |
| 31 | 3.25, s | 57.7 | | 21, 22', 23, 24 | 21 |

D. Synthesis of 7R-FD-895 (1b)

Total synthesis of 7R-FD-895 (1b) is shown in FIGS. 5A through 5B. For this study, it was prepared from compounds 2 and 3b reported in Chan 2020. Updated procedures are provided for this step. Asterisks (*) denote the compounds that differ from that used to prepare FD-895 (1).

Stille Coupling of Stannane 2 and Core 3b

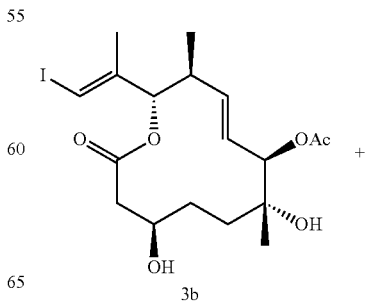

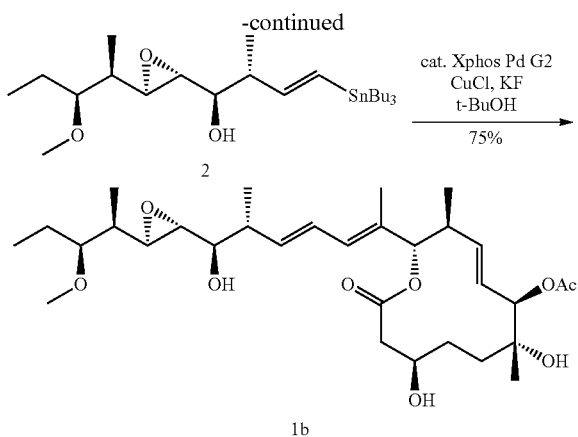

Reagents:
CuCl, anhydrous, beads, 99.99% (Sigma-Aldrich): beads were powdered prior to addition
KF, anhydrous, powder, 99.9% (Sigma-Aldrich): used without further purification
XPhos Pd G2 (Sigma-Aldrich): used without further purification
t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

7R-FD-895 (1b): Yield: 75%, 99.1 mg; TLC (1:3 acetone/ $CH_2Cl_2$): $R_f$=0.28 (CAM stain); NMR data provided in Table S3; FTIR (film) $v_{max}$ 3447, 2963, 2930, 2875, 1739, 1457, 1374, 1239, 1176, 1089, 1021 $cm^{-1}$; HR–ESI–MS m/z calcd. for $C_{31}H_{50}IO_9Na$ $[M+Na]^+$: 589.3348 found 589.3351; $[\alpha]^{25}_D$=+10.9° (c=1.0, $CH_2Cl_2$).

TABLE 3

NMR data for 7R-FD-895 (1b) in $C_6D_6$

| Position | $\delta_H$, mult (J in Hz) | $\delta_C$ | $^1$H, $^1$H-COSY | $^1$H, $^1$H-NOSEY | $^1$H, $^{13}$C-HMBC |
|---|---|---|---|---|---|
| 1 | | 172.3 | | | |
| 2' | 2.35, m | 39.0 | 2', 3 | 3, 4"w, 5' | 1, 3, 4 |
| 2" | 2.29, dd (14.6, 3.1) | | 2", 3 | 3, 4", 5' | 1, 3, 4 |
| 3 | 3.57, bs | 69.6 | 3OH, 4' | 2', 2", 4', 4"w, 5", 24 | N/A |
| 3-OH | 3.67, d (10.6) | | 3 | 4', 5" | conformers |
| 4' | 1.66, m | 30.6 | 3, 4", 5', 5" | 3, 3OH, 5', 5", 7w | conformers |
| 4" | 1.82, m | | 3, 4', 5', 5" | 3w, 5', 5", 7w | 2 |
| 5' | 1.58, m | 36.5 | 4', 4", 5" | 4' | conformers |
| 5" | 0.95, m | | 4', 4", 5' | 4" | conformers |
| 6 | | 73.8 | | | |
| 6-OH | | | | | |
| 7 | 5.40, m | 77.9 | 8 | 4', 10, 15, 24, 27w | 5, 6, 8, 9, 29 |
| 8 | 5.92, dd (15.4, 2.3) | 128.0 | 7, 9 | 7, 9, 10, 11, 13w, 14w, 15w, 22 | 7, 10 |
| 9 | 5.38, m | 130.7 | 8, 10 | 4', 8, 10, 11, 15, 18, 25 | 7, 10 |
| 10 | 2.47, tq (10.1, 6.7) | 41.0 | 11, 25 | 8, 9 25, 26 | 8, 9, 11, 25 |
| 11 | 5.36, d (10.7) | 82.9 | 10 | 4', 8, 10, 13, 25 | 1, 9, 10, 12w, |
| 12 | | 131.9 | | | |
| 13 | 6.15, d (10.9) | 131.5 | 14, 26w | 8, 9, 11, 15, 28 | 11, 15, 26 |
| 14 | 6.26, dd (15.0, | 126.2 | 13, 15 | 15, 16, 22', 26, 27 | 12, 13, 16 |
| 15 | 5.50, dd (15.0, 8.7) | 138.2 | 14, 16 | 8w, 13, 14, 16, 17, 18w, 27 | 13, 16, 17, 27 |
| 16 | 2.37, m | 42.7 | 15, 17, 26 | 14, 15, 27 | 14, 15, 17, 18, |
| 17 | 3.06, t (6.6) | 75.3 | 16, 18 | 16w, 19, 27 | 15, 16, 18, 19, |
| 17-OH | | | | | |
| 18 | 2.65, dd (5.7, 2.2) | 60.7 | 17 | 10, 15, 16, 19, 20, 27w, 28w | 17, 19, 20w |
| 19 | 2.85, dd (8.2, 2.3) | 59.7 | 20 | 10w, 16w, 17w, 18, 20w, 21w, 22'w, 18, 20, 28 | |
| 20 | 1.30, m | 39.4 | 19, 28 | 18, 23, 28 | 18, 19, 27, 28 |
| 21 | 3.14, td (6.3, 4.0) | 83.6 | 20, 22', 22" | 19, 20, 22', 22"w, 23, 28 | 19w, 20, 23, |
| 22' | 1.57, m | 23.8 | 23 | 21, 22β, 23 | 20, 21, 23 |
| 22" | 1.36, m | | 23 | 21, 22α, 23 | 20, 21, 23 |
| 23 | 0.84, t (7.5) | 10.0 | 22', 22" | 21, 22', 22" | 21, 22 |
| 24 | 1.00, s | 24.7 | | 3OH, 5', 5", 7 | 5, 6, 7 |
| 25 | 0.76, d (6.8) | 17.1 | 10 | 9, 10, 11, 20, 26 | 9, 10, 11 |
| 26 | 1.62, bs | 11.5 | | 10, 11, 14 | 11, 12, 13, 14, |
| 27 | 1.12, d (6.8) | 16.9 | 16 | 14, 15, 16, 17w | 15, 16, 17 |
| 28 | 0.84, d (7.0) | 10.6 | 20 | 19, 21 | 19, 20, 21 |
| 29 | | 169.2 | | | |
| 30 | 1.67, s | 20.4 | | | 29 |
| 31 | 3.24, s | 57.8 | | 19, 21, 22', 23, 28 | 21 |

E. Synthesis of 10R, 11R-FD-895 (1c)

Figure 6A:
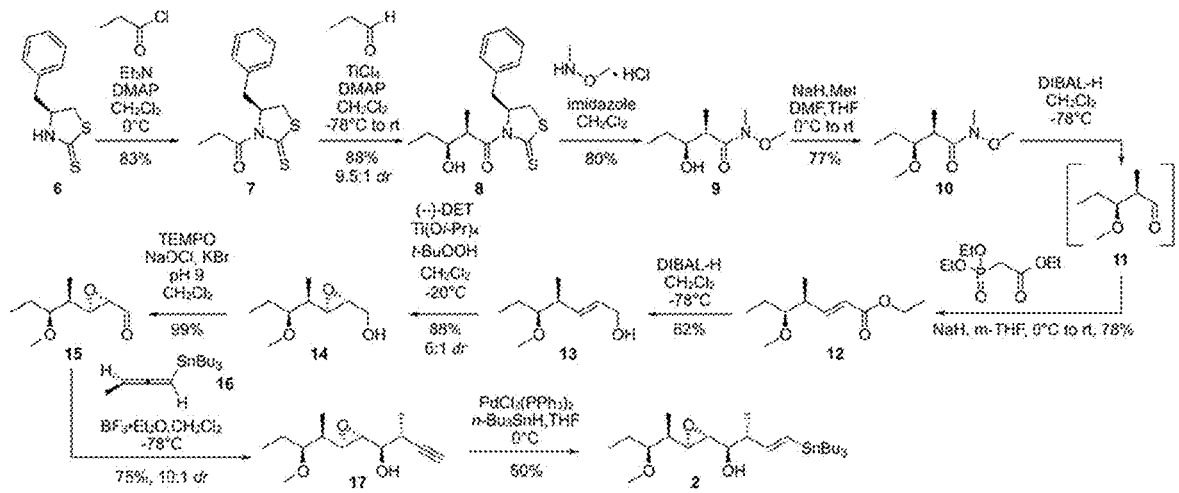
FIGS. 6A to 6C show synthetic scheme of compound 1c (10R, 11R-FD-895) in FIG. 2.
Figure 6B:
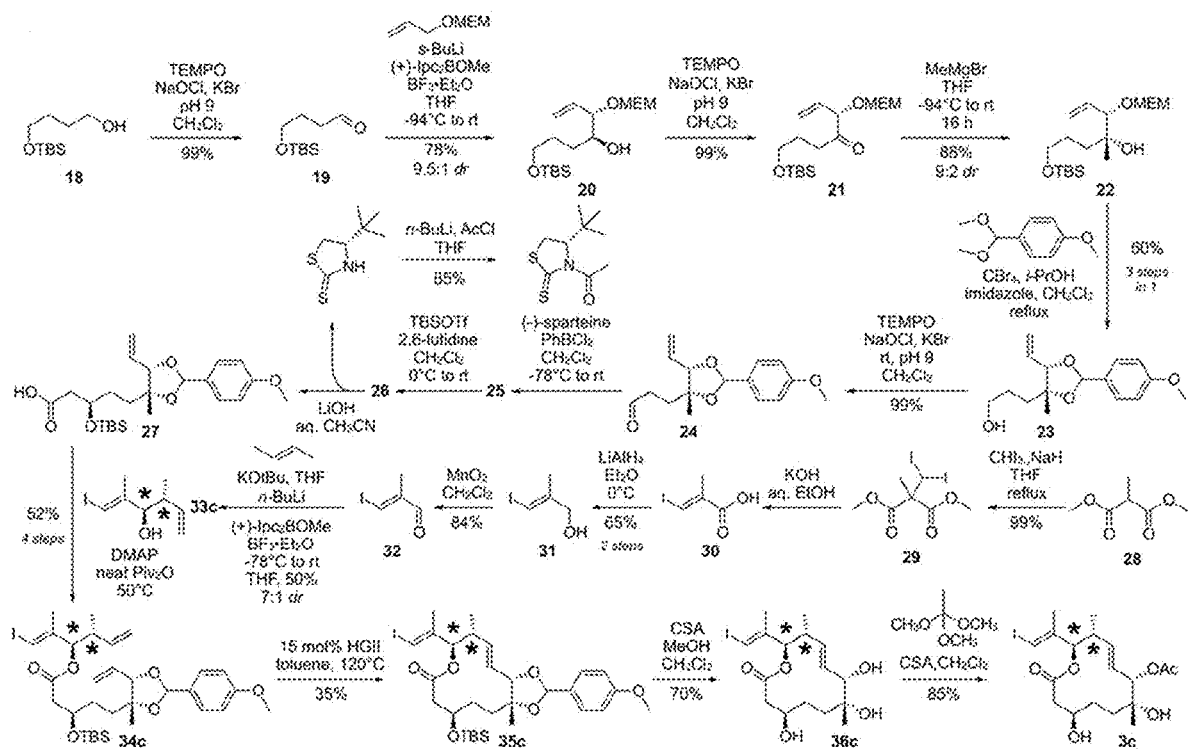
Figure 6C:
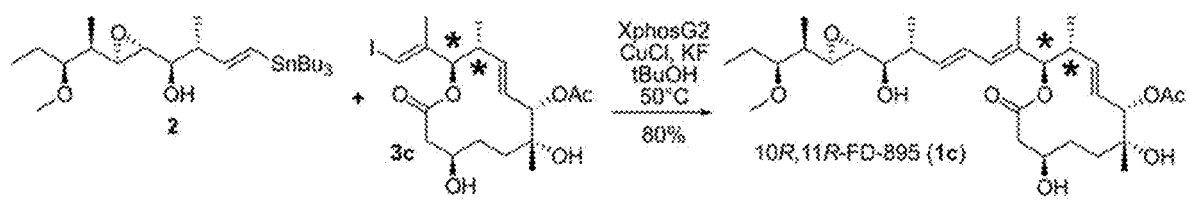
Figure 7A:
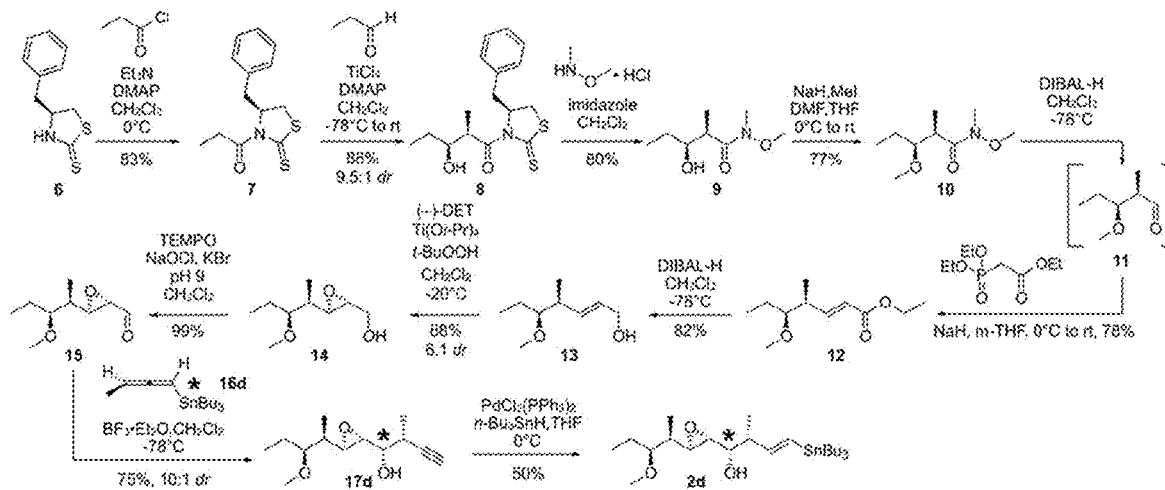
FIGS. 7A to 7C show synthetic scheme of compound 1d (17S-FD-895) in FIG. 2.
Figure 7B:
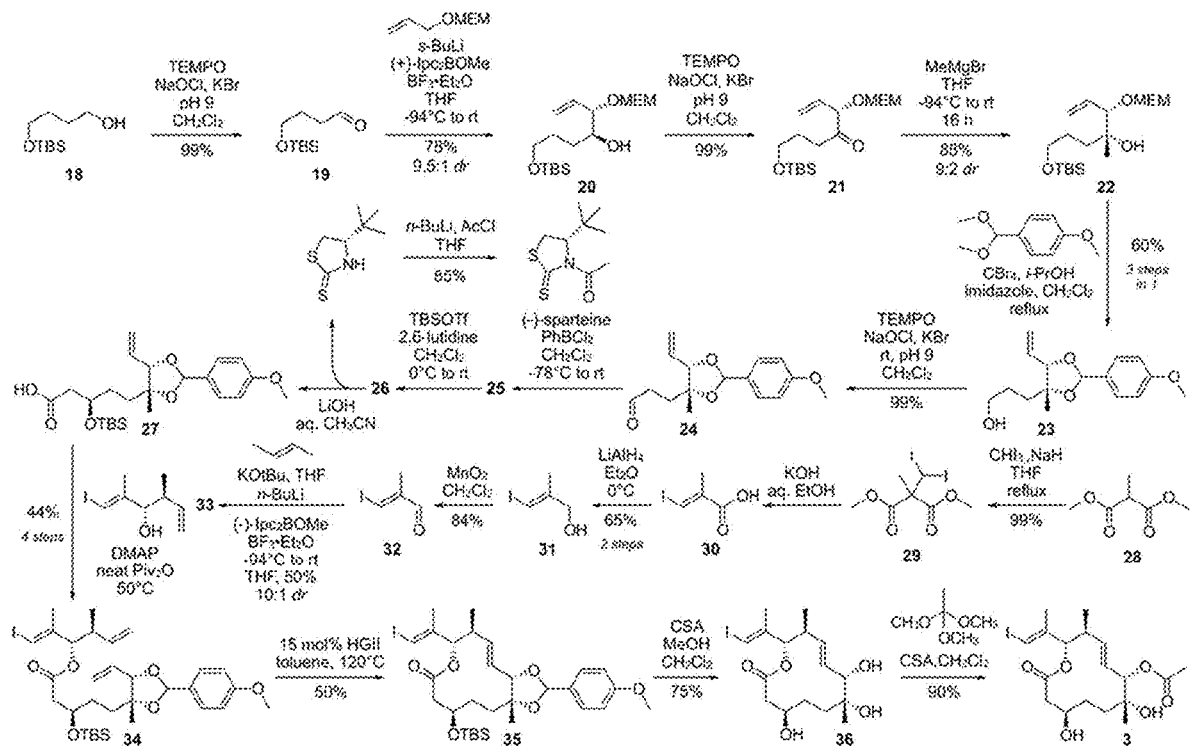
Figure 7C:
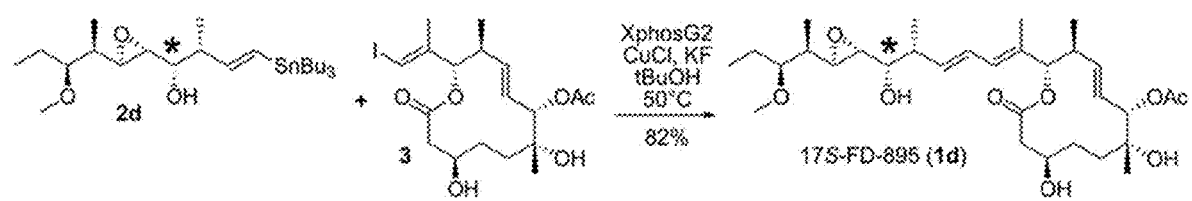

Synthesis of 10R,11R-FD-895 (1c) is shown in FIGS. 6A through 6C. For this study, it was prepared from compounds 32 and 2 reported in Chan 2020. Updated procedures are provided for these steps. Asterisks (*) denote the compounds that differ from that used to prepare FD-895

Crotylation of Aldehyde 32 to Vinyl Iodide 33c

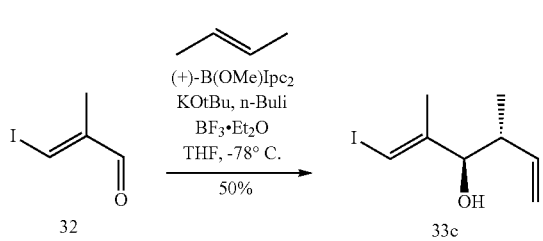

Reagents:
- Trans-2-butene (Acros Organics): used without further purification
- (+)-B-methoxydiisopinocampheylborane (Sigma): used without further purification
- KOt-Bu (Chem-Impex): used without further purification
- n-BuLi (2.5 M in hexane) (Acros Organics): used without further purification
- $BF_3 \cdot Et_2O$ (Alfa Aesar): used without further purification (E)-But-2-ene (20.0 mL, 0.200 mol) was condensed and added to a 1 L reaction flask containing anhydrous THF (300 mL) at −78° C. KOt-Bu (11.4 g, 0.101 mol) was added, and the mixture was stirred at −78° C. for 30 min. n-BuLi (2.5 M in hexane, 40.0 mL, 0.100 mol) was added dropwise over 15 min, and the resulting yellow mixture was stirred at −78° C. for an additional 30 min. A solution of (+)-B-methoxydiisopinocampheylborane (25.3 g, 0.800 mmol) in anhydrous THF (100 mL) was added dropwise over 15 min, and the mixture turned clear. After stirring the mixture for 30 min, $BF_3 \cdot Et_2O$ (17.0 mL, 0.134 mol) was added dropwise over 10 min, and the mixture was stirred for an additional 10 min. After cooling the mixture to −94° C., a solution of 32 (12.1 g, 61.7 mmol) in anhydrous THF (75 mL) was added dropwise over 45 min. The mixture was allowed to warm to rt and stirred for 16 h. $H_2O$ (200 mL) was added, and the mixture was concentrated on a rotary evaporator. Vinyl iodide 33c (7.80 g, 50%) was obtained at a 10:1 dr by flash chromatography, eluting with $CH_2Cl_2$.

Vinyl iodide 33: TLC ($CH_2Cl_2$): $R_f$=0.40 ($KMnO_4$); $^1$H NMR (500 MHz, $CDCl_3$) δ 6.26 (s, 1H), 5.72 (m, 1H), 5.18 (d, J=16.0 Hz, 1H), 5.18 (d, J=11.3 Hz, 1H), 3.87 (dd, J=8.1, 2.9 Hz, 1H), 2.36 (h, J=7.4 Hz, 1H), 1.88 (d, J=2.9 Hz, 1H), 1.82 (b s, 3H), 0.92 (d, J=6.8 Hz, 3H); $^{13}$C NMR (125 MHz, $CDCl_3$) δ 148.1, 140.0, 117.4, 80.2, 80.0, 42.4, 19.4, 16.6; HR-ES-MS m/z calcd. for $C_8H_{13}INa$ [M+Na]$^+$: 274.9998, found 274.9997; $[α]^{25}_D$=+21.4° (c=1.0, $CH_2Cl_2$).

Esterification of Acids 27 with Alcohol 33c to Afford 34c

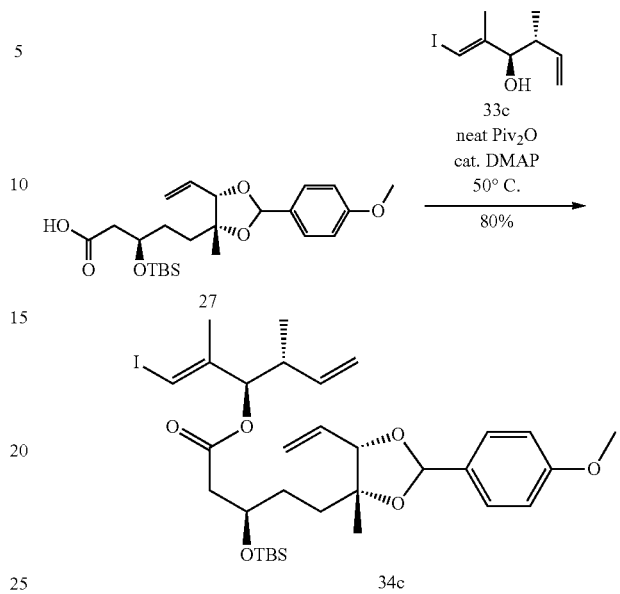

Reagents:
- DMAP, 98% (Sigma-Aldrich): used without further purification
- Pivalic anhydride, 99% (Alfa Aesar): used without further purification 3S,4S,E)-1-Iodo-2,4-dimethylhexa-1,5-dien-3-yl)-(3R)-3-((tert-butyldimethylsilyl)oxy)-5-((4R,5S)-2-(4-methoxyphenyl)-4-methyl-5-vinyl-1,3-dioxolan-4-yl)pentanoate (34). DMAP (150 mg, 1.22 mmol) and pivalic anhydride (3.71 mL, 18.3 mmol) were added sequentially to a 250 mL flask containing 27 (5.51 g, 12.2 mmol) and alcohol 33 (3.23 g, 12.8 mmol). The mixture was purged with Ar and stirred neat at 50° C. for 8 h. Pivalic anhydride was removed from the mixture under airflow. Crude material was then loaded directly onto silica gel in hexanes and eluted with a gradient of hexanes to 1:10 $Et_2O$/hexanes. Pure esters 34 (6.72 g, 80%) were obtained as a clear oil.

Esters 34: TLC (1:4 $Et_2O$/hexanes): $R_f$=0.40 and 0.38 (CAM stain); $^1$H NMR (500 MHz, $C_6D_6$) δ 7.57 (d, J=8.7 Hz, 2H), 7.55 (d, J=8.7 Hz, 2H), 6.86 (d, J=8.6 Hz, 2H), 6.82 (d, J=8.6 Hz, 2H), 6.22 (s, 1H), 6.20 (s, 1H), 5.93 (s, 1H), 5.83 (m, 1H), 5.79 (m, 2H), 5.63 (m, 1H), 5.60 (m, 1H), 5.33 (dt, J=17.2, 1.6 Hz, 1H), 5.22 (d, J=8.1 Hz, 1H), 5.19 (d, J=8.1 Hz, 1H), 5.09 (dq, J=10.4, 1.4 Hz, 1H), 4.96 (m, 2H), 4.27 (m, 1H), 4.22 (m, 1H), 4.12 (dt, J=6.6, 1.3 Hz, 1H), 3.29 (s, 3H), 3.26 (s, 3H), 2.46 (dd, J=15.0, 6.3 Hz, 1H), 2.42 (dd, J=15.0, 6.6 Hz, 1H), 2.30 (dd, J=15.0, 5.6 Hz, 1H), 2.25 (m, 1H), 2.22 (dd, J=15.0, 5.7 Hz, 1H), 1.98 (dt, J=13.0, 4.0 Hz, 1H), 1.87 (m, 1H), 1.79 (m, 1H), 1.71 (d, J=1.1 Hz, 3H), 1.69 (d, J=1.1 Hz, 3H), 1.67 (m, 1H), 1.25 (s, 3H), 1.24 (m, 2H), 1.21 (s, 3H), 1.01 (s, 9H), 0.98 (s, 9H), 0.67 (d, J=5.3 Hz, 3H), 0.65 (d, J=5.3 Hz, 3H), 0.14 (s, 3H), 0.14 (s, 3H), 0.12 (s, 3H), 0.09 (s, 3H); $^{13}$C NMR (125 MHz, $C_6D_6$) δ 170.3, 170.3, 160.8, 160.6, 144.8, 144.7, 139.8, 133.6, 132.9, 131.2, 128.6, 128.4, 128.2, 128.1, 127.6, 118.0, 117.9, 115.8, 115.8, 114.0, 113.9, 102.7, 102.3, 87.9, 86.0, 83.3, 82.4, 82.1, 80.4, 80.3, 69.9, 69.8, 54.8, 42.9, 42.6, 40.5, 40.5, 32.9, 31.9, 31.4, 28.9, 26.2, 26.2, 22.7, 22.1, 20.0, 18.3, 18.3, 16.5, 16.4, −4.4, −4.4, −4.5; FTIR (film) $ν_{max}$ 2956, 2929, 2856, 1739, 1616, 1517, 1378, 1249, 1170, 1070 cm$^{-1}$; HR-ES-MS m/z calcd. for $C_{32}H_{49}NO_5S_2SiNa$ [M+Na]$^+$: 707.2203, found 707.2199; $[α]^{25}_D$=−13.1° (c=1.0, $CH_2Cl_2$).

Ring-Closing Metathesis of Ester 34c

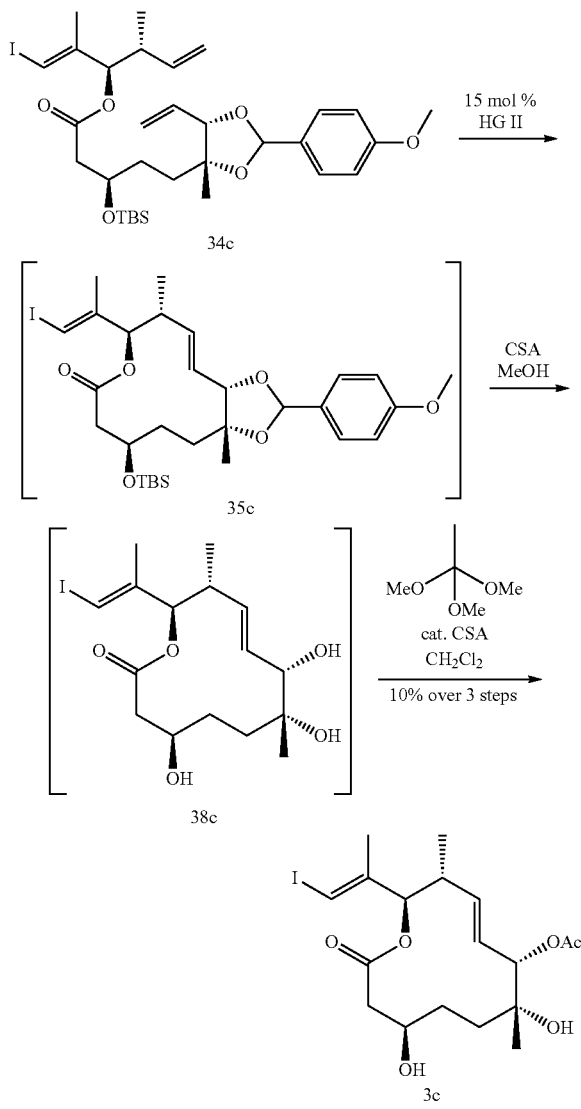

Reagents:
2$^{nd}$ Generation Hoyveda Grubbs catalyst, 97% (Sigma-Aldrich): used without further purification
(1S)-(+)-10-Camphorsulfonic acid, 98% (TCI Chemicals): used without further purification Trimethyl orthoformate, 99% (Sigma-Aldrich): used without further purification (2R,3R,6S,7R,10R,E)-7,10-dihydroxy-2-(E)-1-iodoprop-1-en-2-yl)-3,7-dimethyl-12-oxooxacyclododec-4-en-6-yl acetate (3c) Esters 34c (5.15 g, 7.52 mmol) in a two-necked 3 L flask equipped with a 1 L addition funnel were dissolved into anhydrous, degassed toluene (700 mL). The mixture was purged with Ar and heated to reflux. 2$^{nd}$ Generation Hoyveda-Grubbs catalyst (706 mg, 1.13 mmol) in anhydrous, degassed toluene (700 mL) purged under Ar was dropwise added to the solution of 34 in boiling toluene. After stirring for 20 min the mixture turned from a clear green color into a black solution and was further stirred at reflux for 5 h. The mixture was then cooled to rt and concentrated by a rotary evaporator. The crude black semi-solid was then suspended in hexanes and filtered through a pad of Celite and eluted with hexanes. The elutants were concentrated on a rotary evaporator to yield a crude green oil. Crude lactones 35c were then dissolved in 1:3 MeOH/CH$_2$Cl$_2$ (300 mL) in a 1 L flask. (1S)-(+)-10-Camphorsulfonic acid (3.45 g, 14.9 mmol) was added as a solid in one portion. The mixture was stirred for 5 h, at which point TLC analyses indicated complete conversion of starting material. Satd. NaHCO$_3$ (50 mL) was added, and the mixture was extracted into CH$_2$Cl$_2$ (3×200 mL). The organics were collected and concentrated on a rotary evaporator to a crude oil. Crude triol 36c was subjected to dry column vacuum chromatography over silica and the column was washed with CH$_2$Cl$_2$ (500 mL). Crude triol 36c was eluted with acetone, concentrated, and carried forward without further purification. Trimethyl orthoformate (400 µL, 3.13 mmol) was added dropwise as a solution of CH$_2$Cl$_2$ (20 mL) to a mixture of crude triol 36c and (1S)-(+)-10-camphorsulfonic acid (120 mg, 0.259 mmol). The mixture was stirred at 0° C. for 1 h, at which point satd. NH$_4$Cl (5 mL) was added. The mixture was stirred for 20 min and extracted into CH$_2$Cl$_2$ (150 mL). The organics were concentrated on a rotary evaporator. Pure core 3c (25.1 mg, 10% over three steps) was obtained as a mixture of two isomers by flash chromatography, eluting with a gradient of CH$_2$Cl$_2$ to 1:3 acetone/CH$_2$Cl$_2$.

Core 3: TLC (1:8 acetone/CH$_2$Cl$_2$): R$_f$=0.328 (CAM stain); $^1$H NMR (500 MHz, C$_6$D$_6$) δ 6.19 (s, 1H), 5.82 (dd, J=15.3, 9.8 Hz, 1H), 5.45 (dd, J=15.3, 10.1 Hz, 1H), 5.18 (d, J=9.8 Hz, 1H), 5.09 (d, J=10.6 Hz, 1H), 4.11 (bs, 1H), 2.30 (m, 2H), 2.21 (m, 1H), 2.08 (d, J=14.9 Hz, 1H), 1.76 (bs, 1H), 1.64 (m, 1H), 1.62 (s, 3H), 1.61 (d, J=1.1 Hz, 3H), 1.55 (m, 1H), 1.44 (m, 1H), 1.22 (m, 2H), 1.04 (s, 3H), 0.51 (d, J=6.7 Hz, 3H); $^{13}$C NMR (125 MHz, C$_6$D$_6$) δ171.7, 169.0, 143.8, 139.8, 126.9, 84.4, 80.0, 79.0, 73.2, 69.3, 41.1, 38.4, 35.8, 30.2, 24.7, 20.8, 19.1, 16.1; FTIR (film) v$_{max}$ 3502, 3058, 2959, 2873, 1733, 1616, 1368, 1243, 1168, 1021 cm$^{-1}$; HR–ESI–MS m/z calcd. for C$_{18}$H$_{27}$IO$_6$Na [M+Na]$^+$: 489.0745, found 489.0742; [α]$^{25}$$_D$=−38.5° (c=1.0, CH$_2$Cl$_2$).

Stille Coupling of Stannane 2 and Core 3c to Afford 10R, 11R-FD-895 (1c).

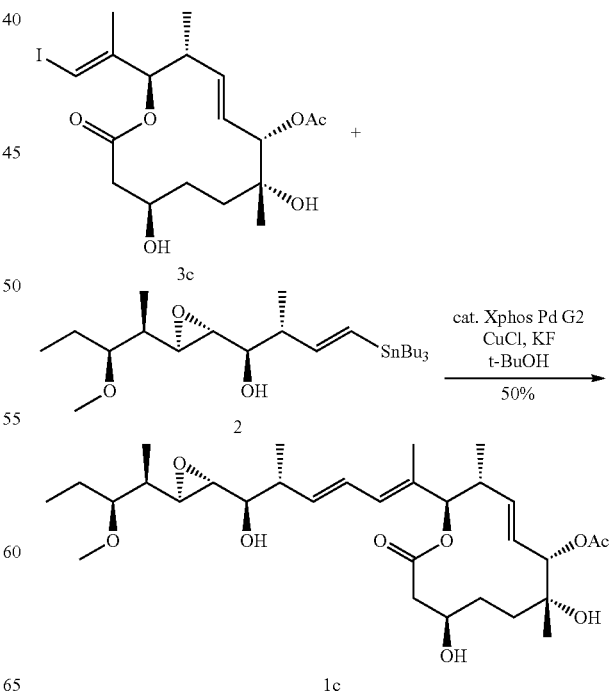

Reagents:
- CuCl, anhydrous, beads, 99.99% (Sigma-Aldrich): beads were powdered prior to addition
- KF, anhydrous, powder, 99.9% (Sigma-Aldrich): used without further purification
- XPhos Pd G2 (Sigma-Aldrich): used without further purification
- t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

10R,11R-FD-895 (1c): Yield: 50%, 6.60 mg; TLC (1:3 acetone/$CH_2Cl_2$): $R_f$=0.28 (CAM stain); NMR data provided in Table S4; FTIR (film) $v_{max}$ 3447, 2963, 2930, 2875, 1739, 1457, 1374, 1239, 1176, 1089, 1021 $cm^{-1}$; HR–ESI–MS m/z calcd. for $C_{31}H_{50}IO_9Na$ $[M+Na]^+$: 589.3348 found 589.3351; $[\alpha]^{25}_D$=+10.9° (c=1.0, $CH_2Cl_2$).

F. Synthesis of 17S-FD-895 (1d)

Total synthesis of 17S-FD-895 (1d) is shown in FIGS. 7A through 7E. For this study, 1d was prepared from compounds 2d and 3 reported in Chan 2020. Updated procedures are provided for this step. Asterisks (*) denote the compounds that differ from that used to prepare FD-895 (1). Stille Coupling of Stannane 2d and Core 3 to Afford 17S-FD-895 (1d).

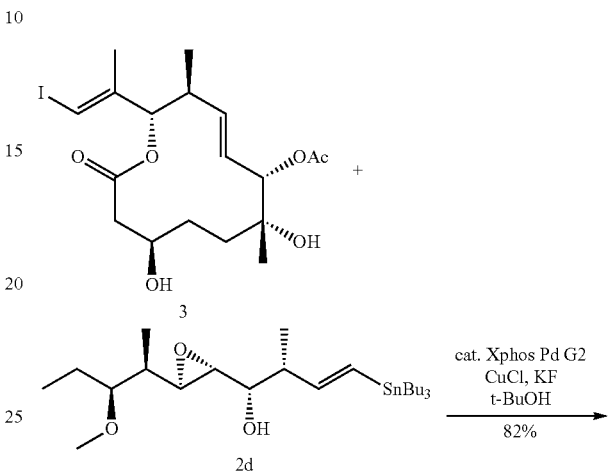

TABLE 4

| | NMR data for 10R, 11R -FD-895 (1c) in $C_6D_6$ | | | |
|---|---|---|---|---|
| Position | $\delta_H$, mult (J in Hz) | $\delta_C$ | $^1H$, $^1H$-COSY | $^1H$, $^1H$-NOSEY | $^1H$, $^{13}C$-HMBC |
| 1 | | 169.6 | | | |
| 2' | 2.38, m | 40.1 | 2', 3 | 3w, 5' | 1, 3, 4 |
| 2" | 2.25, dd (13.3, 5 .3) | | 2', 3 | 3 | 1, 3, 4 |
| 3 | 4.14, m | 67.8 | 2', 2"w | 2'w, 2", 4', 4", 5'w, 24 | |
| 3-OH | | | | | |
| 4' | 1.29, m | 27.5 | 3, 4", 5', 5" | 3, 4", 5', 5" | 5, 3 |
| 4" | 1.20, m | | 3w, 4', 5', 5" | 3, 4', 5', 5", 24 | 5 |
| 5' | 1.83, m | 30.7 | 4', 4", 5" | 2', 4', 4", 8, 25 | 3w, 4, 6, 7w, |
| 5" | 1.75, dt (13.4, 6.7) | | 4', 4", 5' | 4', 4", 24 | 3w, 4, 6, 7, 24, |
| 6 | | 73.5 | | | |
| 6-OH | 1.75, s | | | | |
| 7 | 5.23, d (9.8) | 79.3 | 8 | 4', 8w, 9, 24 | 8, 9, 24w, 29 |
| 8 | 5.90, dd (15.2, 9.8) | 126.6 | 7, 9, 10w | 5', 7, 9, 10 | 6, 10 |
| 9 | 5.58, dd (15.3, 10.0) | 140.3 | 8, 10 | 4', 7, 8, 10, 11, 25 | 7, 10 |
| 10 | 2.43, m | 41.2 | 11, 25 | 8, 9, 11, 25, 26 | 8, 9, 11, 25 |
| 11 | 5.18, d (10.8) | 82.1 | 10 | 9, 10w, 13, 25, 26w | 1, 9, 10, 12, 13, |
| 12 | | 132.2 | | | |
| 13 | 6.17, d (10.8) | 131.3 | 14, 26w | 9, 11, 15, 25, 26 | 11, 15, 26 |
| 14 | 6.27, dd (15.1, 10.8) | 126.5 | 13, 15 | 15, 16, 26, 27 | 12, 13, 16 |
| 15 | 5.53, dd (15.1, 8.8) | 137.8 | 14, 16 | 13, 14, 16, 17, 18w, 27 | 13, 16, 17 |
| 16 | 2.36, m | 42.8 | 15, 17, 27 | 14, 15, 17, 18, 27 | 14, 15, 17, 18, |
| 17 | 3.12, m | 74.8 | 16, 18 | 15, 16, 18, 19, 27 | 15w, 16, 19, 25 |
| 17-OH | 1.55, bs | | | | |
| 18 | 2.69, dd (5.1, 2.2) | 60.3 | 17, 19w | 14w, 15, 16, 17, 19, 20, 27, | 17, 19, 20 |
| 19 | 2.90, dd (8.1, 2.3) | 59.4 | 18w, 20 | 17, 18w, 20, 22'w, 28 | 17w, 18, 20, |
| 20 | 1.31, m | 39.2 | 19, 28 | 19, 21, 28 | 19, 23 |
| 21 | 3.14, m | 83.6 | 20, 22', 22" | 20, 22', 22", 23 | 19, 20, 22w, |
| 22' | 1.60, m | 23.9 | 21, 22", 23 | 21, 22", 23 | 20, 21, 23 |
| 22" | 1.39, m | | 21, 22', 23 | 19w, 21, 22', 23, 31 | 20, 21, 23 |
| 23 | 0.84, t (7.5) | 10.1 | 22', 22" | 20, 21, 22', 22", 31w | 21, 22 |
| 24 | 1.06, s | 24.8 | | 4'w, 4", 5'w, 5", 7 | 5, 6, 7 |
| 25 | 0.72, d (6.7) | 16.5 | 10 | 5', 9, 10, 11, 13, 26 | 9, 10, 11 |
| 26 | 1.58, s | 12.0 | 13 | 10, 14, 25w | 11, 12, 13, 14 |
| 27 | 1.11, d (6.8) | 16.9 | 16 | 14, 15, 16, 17, 18w | 15, 16, 17 |
| 28 | 0.87, d (7.0) | 10.5 | 20 | 18, 19, 20, 21, 22' | 19, 20, 21 |
| 29 | | 169.2 | | | |
| 30 | 1.63, s | 20.8 | | | 29 |
| 31 | 3.24, s | 57.7 | | 19w, 21, 22", 23 | 21 |

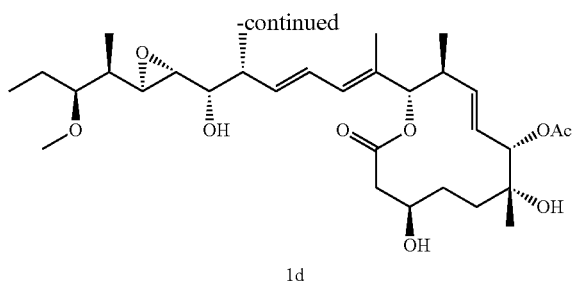

1d

Reagents:

CuCl, anhydrous, beads, 99.99% (Sigma-Aldrich): beads were powdered prior to addition KF, anhydrous, powder, 99.9% (Sigma-Aldrich): used without further purification XPhos Pd G2 (Sigma-Aldrich): used without further purification t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

17S-FD-895 (1d): Yield: 80%, 66.4 mg; TLC (1:3 acetone/CH$_2$Cl$_2$): R$_f$=0.28 (CAM stain); NMR data provided in Table S5; FTIR (film) $\nu_{max}$ 3447, 2963, 2930, 2875, 1739, 1457, 1374, 1239, 1176, 1089, 1021 cm$^{-1}$; HR–ESI–MS m/z calcd. for C$_{31}$H$_{50}$IO$_9$Na [M+Na]$^+$: 589.3345, found 589.3347; $[\alpha]^{25}_D$=+8.8° (c=1.0, CH$_2$Cl$_2$).

TABLE 5

NMR data for 17S-FD-895 (1d) in C$_6$D$_6$

| Position | $\delta_H$, mult (J in Hz) | $\delta_C$ | $^1$H, $^1$H-COSY | $^1$H, $^1$H-NOSEY | $^1$H, $^{13}$C-HMBC |
|---|---|---|---|---|---|
| 1 | | 171.8 | | | |
| 2' | 2.29, dd (14.8, 3.9) | 38.2 | 2', 3 | 3, 3OHw, 4'/5'w | 3 |
| 2" | 2.19, dd (14.8, 3.0) | | 2", 3 | 3, 4'/5' | 1 |
| 3 | 3.49, td (11.1, 3.5) | 69.0 | 3OH, 4'w, | 2', 2", 3OH, 4'/5', 5" | |
| 3-OH | 3.63, d (11.2) | | 3 | 2', 3, 4", 6OH | 3 |
| 4' | 1.57, m | 30.0 | 3w, 4", 5', | 2", 3, 5", 24 | |
| 4" | 1.25, m | | 3, 4', 5', 5" | 3OHw, 5', 7, 9, 24w | 3w |
| 5' | 1.55, m | 35.5 | 3, 4" | 2", 3OH, 4", 6OH, 8 | |
| 5" | 1.20, m | | 5' | 3, 4', 7w, 24 | 4w, 6w, 7w |
| 6 | | 72.5 | | | |
| 6-OH | 1.75, s | | | 3OH, 5"w, 7w, 8, 24 | 5, 6, 17 |
| 7 | 5.26, d (1.5) | 78.8 | 8 | 4", 8, 9w, 24 | 8, 29 |
| 8 | 5.83, dd (15.2, 9.8) | 140.3 | 7, 9 | 4'/5', 7, 9, 10w, 25 | 7, 10w |
| 9 | 5.62, dd (15.2, 10.0) | 126.0 | 8, 10 | 4'/5', 7, 8, 10, 25 | 10, 25w |
| 10 | 2.39, m | 40.8 | 9, 11, 25 | 7w, 8, 9w, 11w, 25, 26 | 11 |
| 11 | 5.24, d (2.4) | 82.2 | 10 | 9, 10, 13, 25, 26 | 1, 12, 13, 26 |
| 12 | | 131.0 | | | |
| 13 | 6.11, d (10.7) | 131.4 | 14, 26w | 11, 14, 15, 25, 26w | 11, 14w, 15, |
| 14 | 6.26, dd (15.2, 10.8) | 126.1 | 13, 15 | 13, 15, 16, 26, 27w | 12w, 13w |
| 15 | 5.80, dd (15.2, 8.3) | 137.6 | 14, 16 | 13, 14, 27 | 12, 13, 14, 16, |
| 16 | 2.36, m | 41.2 | 15, 17, 27 | 14, 17, 27 | 15 |
| 17 | 3.42, q (3.7) | 73.0 | 16, 17OH, | 15, 16, 17OH, 18, 19, 27 | |
| 17-OH | 1.55, bs | | | 17, 19 | 16, 17 |
| 18 | 2.56, dd (3.8, 2.2) | 57.3 | 17, 19w | 15w, 16, 17, 19w, 20, 27, | |
| 19 | 3.01, dd (8.3, 2.3) | 59.3 | 18, 20 | 15w, 17, 17OH, 18w, 20, | 20 |
| 20 | 1.33, m | 38.9 | 19, 21, 28 | 18, 19w, 21, 23, 28 | |
| 21 | 3.15, m | 83.4 | 22', 22" | 19, 20, 22', 22", 23 | 19, 28 |
| 22' | 1.63, m | 23.5 | 21, 23 | 21w, 22", 23 | 20w, 21, 23 |
| 22" | 1.40, dt (14.0, 6.9) | | 21, 23 | 21w, 22', 23 | 20w, 21, 23 |
| 23 | 0.85, t (7.5) | 9.7 | 22', 22" | 20, 21, 22', 22" | 21, 22 |
| 24 | 1.00, s | 24.4 | | 4'/5', 4"w, 5", 6OH, 7 | 5, 6, 7 |
| 25 | 0.70, d (6.7) | 16.1 | 10 | 7, 9, 10, 13, 26 | 8, 10, 11 |
| 26 | 1.59, d (1.3) | 11.5 | 13 | 10, 11w, 14, 25 | 11, 12, 13, |
| 27 | 1.12, d (7.0) | 16.9 | 16 | 9, 14, 15, 16, 17, 18 | 15, 16, 17 |
| 28 | 0.88, d (6.9) | 10.5 | 20 | 18, 19, 20, 21 | 19, 20, 21 |
| 29 | | 168.7 | | | |
| 30 | 1.61, s | 20.4 | | | 29 |
| 31 | 3.23, s | 57.4 | | 21, 22', 22", 23 | 21 |

G. Synthesis of 17-methoxy-FD-895 (1e)

Figure 8A:
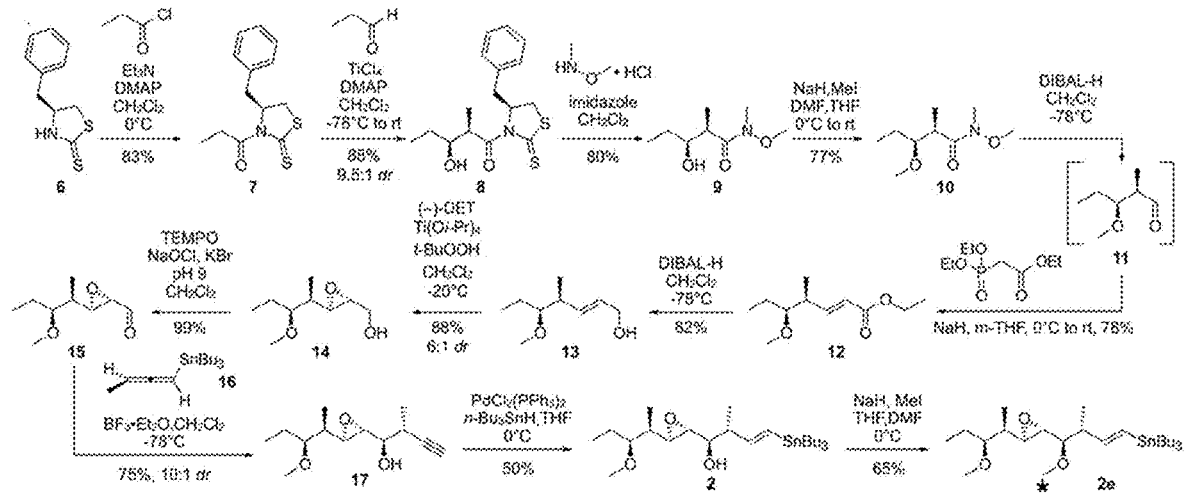
FIGS. 8A to 8C show synthetic scheme of compound 1e (17-methoxy-FD-895) in FIG. 2.
Figure 8B:
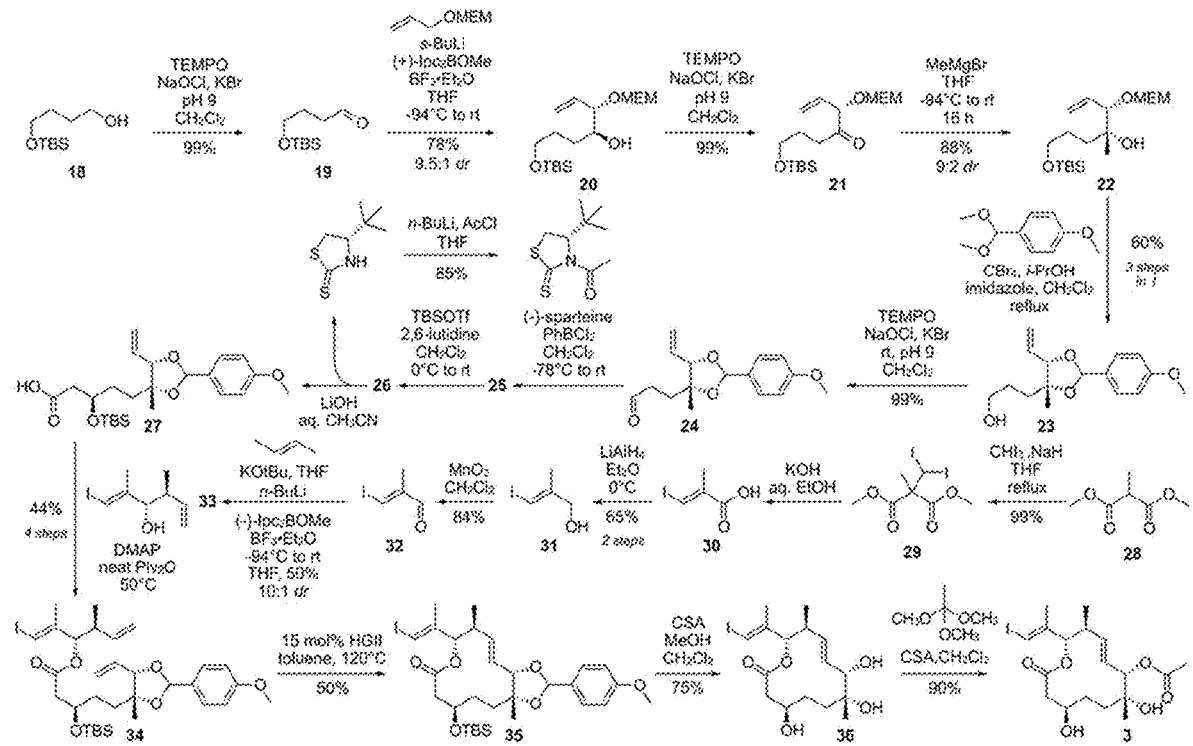
Figure 8C:
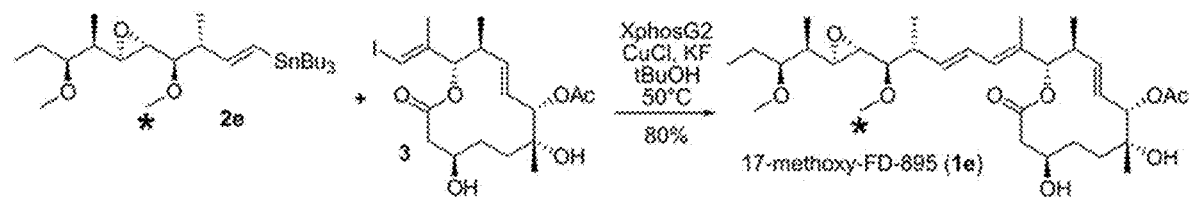

Total synthesis of 17-methoxy-FD-895 (1e) is shown in FIGS. 8A through 8C. For this study, 1e was prepared from compounds 2a and 3 reported in Chan 2020. Updated procedures are provided for this step. Asterisks (*) denote the compounds that differ from that used to prepare FD-895 (1).

Methylation of Stannane 2 to Afford Stannane 2e

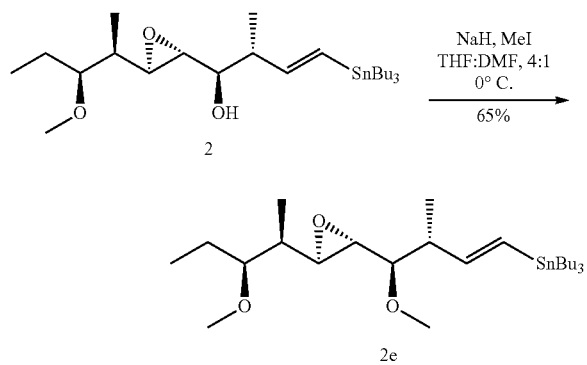

Reagents:
  NaH, 60% in mineral oil (Alfa Aesar): used without further purification
  MeI, 98% (Sigma-Aldrich): used without further purification Tributyl(3R,4R,E)-4-methoxy-44(2S,3R)-3-((2R,3S)-3-methoxypentan-2-yl)oxiran-2-yl)-3-methylbut-1-en-1-yl) stannane (2e). MeI (0.0586 mL, 0.941 mmol) was added at rt to a solution of stannane 2 (50.0 mg, 0.0941 mmol) in a mixture of anhydrous THF (10 mL) and anhydrous DMF (3 mL) in a 50 mL flask. The mixture was cooled to 0° C. and NaH (60% in mineral oil, 8.85 mg, 0.221 mmol) was added in portions ensuring the mixture remained at 0° C. The mixture was slowly warmed to rt and stirred for 16 h. After cooling the mixture to 0° C., a solution of phosphate buffered saline pH 7 (5 mL) was added dropwise. The volatiles were concentrated on a rotary evaporator. The mixture was extracted with hexane (3×50 mL). The combined organic phases were washed with brine, dried over $Na_2SO_4$, filtered and concentrated on a rotary evaporator. Pure stannane 2e (34.9 mg, 70%) was obtained as a colorless oil by flash chromatography, eluting with a gradient of hexanes to 10% $Et_2O$/hexanes.

Vinylstannane 2e: TLC (1:10 $Et_2O$/hexanes): $R_f$=0.50 (CAM stain); $^1$H NMR (500 MHz, $C_6D_6$) δ6.35 (dd, J=19.1, 6.8 Hz, 1H), 6.16 (d, J=19.1 Hz, 1H), 3.50 (s, 3H), 3.45 (m, 1H), 3.23 (s, 3H), 3.19 (m, 1H), 2.83 (dd, J=4.4, 2.3 Hz, 1H), 2.75 (dd, J=4.4, 2.3 Hz, 1H), 2.60 (td, J=6.9, 5.2 Hz, 1H), 1.61 (m, 8H), 1.39 (m, 8H), 1.19 (d, J=6.9 Hz, 3H), 1.01 (d, J=7.1 Hz, 3H), 1.00 (d, J=8.1 Hz, 3H), 0.95 (t, J=7.4 Hz, 12H), 0.84 (t, J=7.4 Hz, 3H); $^{13}$C NMR (125 MHz, $C_6D_6$) δ 151.7, 127.3, 86.2, 83.5, 60.2, 58.4, 58.4, 57.6, 56.9, 44.9, 39.7, 32.0, 29.6, 27.8, 23.1, 23.1, 15.6, 14.4, 14.0, 10.9, 10.0, 9.8; FTIR (film) $v_{max}$ 3454, 3310, 2973, 2937, 2890, 1459, 1101, 840 $cm^{-1}$; HR–ESI–MS m/z calcd. for $C_{25}H_{50}O_3Sn$ [M+H]$^+$533.2998, found 533.2994; $[α]^{25}{}_D$=+10.4° (c=1.0, $CH_2Cl_2$).

Stille Coupling of Stannane 2e and Core 3 to Afford 17-O-Methyl-FD-895 (1e)

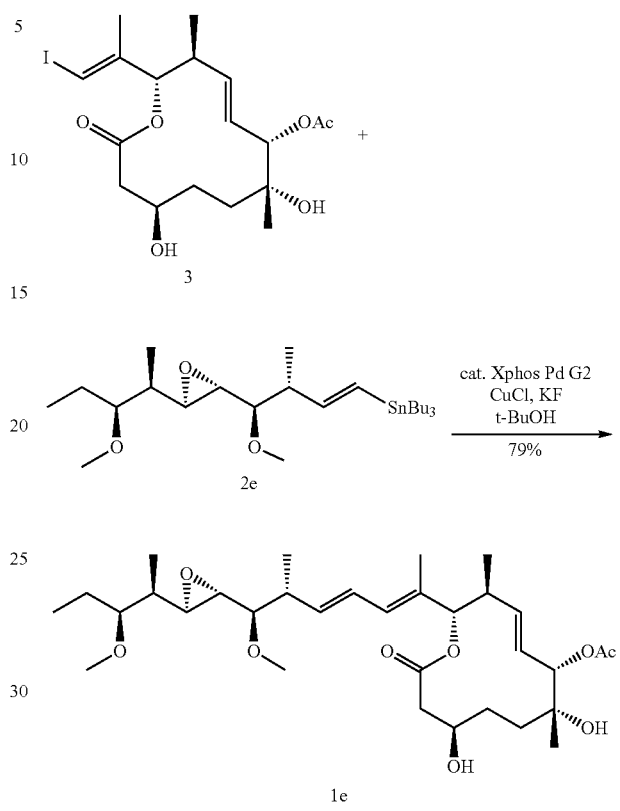

Reagents:
  CuCl, anhydrous, beads, 99.99% (Sigma-Aldrich): beads were powdered prior to addition
  KF, anhydrous, powder, 99.9% (Sigma-Aldrich): used without further purification
  XPhos Pd G2 (Sigma-Aldrich): used without further purification
  t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

17-O-Methyl-FD-895 (1e): Yield: 79%, 8.81 mg; TLC (1:3 acetone/hexanes): $R_f$=0.40 (CAM stain); NMR data provided in Table S6; FTIR (film) $v_{max}$ 3447, 2963, 2930, 2875, 1739, 1457, 1374, 1239, 1176, 1089, 1021 $cm^{-1}$; HR–ESI–MS m/z calcd. for $C_{31}H_{50}IO_9Na$ [M+Na]$^+$: 603.7642, found 603.7641; $[α]^{25}{}_D$=+36.9° (c=1.0, $CH_2Cl_2$).

TABLE 6

NMR data for 17-O-Me-FD-895 (1e) in $C_6D_6$

| Position | $\delta_H$, mult (J in Hz) | $\delta_C$ | $^1H$, $^1H$-COSY | $^1H$, $^1H$-NOSEY | $^1H$, $^{13}C$-HMBC |
|---|---|---|---|---|---|
| 1 | | 172.1 | | | |
| 2' | 2.29, dd (14.8, 3.8) | 38.6 | 2", 3 | 3, 4'w | 1, 3, 4w |
| 2" | 2.20, dd (14.8, 3.0) | | 2', 3 | 3, 5' | 1 |
| 3 | 3.48, m | 69.3 | 2'w, 2"w, 3OH | 2', 2", 4', 5" | |
| 3-OH | 3.62, d (11.1) | | 3 | 3, 6OH | |
| 4' | 1.57, m | 30.4 | 3, 4", 5', 5" | 3, 5", 7, 8 | 5, 6, 3, 24 |
| 4" | 1.26, m | | 4', 5', 5" | 2", 3, 5", 9 | 3 |
| 5' | 1.54, m | 35.9 | 4', 4", 5" | 2", 4', 8 | 4, 6, 24 |
| 5" | 1.18, m | | 4', 4", 5' | 4' | 6, 7 |
| 6 | | 73.6 | | | |
| 6-OH | 1.77, s | | | | |
| 7 | 5.24, d (5.5) | 79.2 | 8 | 4"/5", 8, 9, 24w, 26 | 8w, 9, 24w, 29 |
| 8 | 5.82, dd (15.2, 9.8) | 126.4 | 7, 9 | 4'/5', 7w, 9, 10, 13w | 6w, 9w, 10 |
| 9 | 5.62, dd (15.1, 10.9) | 140.7 | 8, 10 | 4"/5", 7, 8, 10, 11, 25 | 7, 8w, 10, 25 |
| 10 | 2.39, tq (10.4, 6.8) | 41.1 | 9, 11, 25 | 8, 9w, 25, 26 | 8, 9w, 11, 12, 25 |
| 11 | 5.26, d (6.3) | 82.6 | 10 | 10, 13, 25, 26 | 1, 9, 10, 13, |
| 12 | | 131.7 | | | |
| 13 | 6.12, dd (10.9, 1.5) | 131.4 | 14, 26 | 8w, 11, 14, 15, 25, 26w | 11, 15, 26 |
| 14 | 6.23, ddd (15.1, 10.9, | 125.7 | 13, 15 | 8w, 13, 15, 16, 26 | 13w, 16 |
| 15 | 5.64, dd (15.2, 10.2) | 138.7 | 14, 16 | 13, 14, 16, 17 | 12, 13, 14w, 16, |
| 16 | 2.48, dq (14.4, 7.0) | 42.6 | 15, 17, 27 | 14, 15, 17w, 27w, 32w | 14, 15, 17, 18, |
| 17 | 2.62, t (7.1) | 86.2 | 16, 18 | 15w, 16, 20, 32 | 15, 16, 18, 27, |
| 17-OH | | | | | |
| 18 | 2.68, m | 60.6 | 17 | 15, 16, 20, 32 | 17, 19w, 20 |
| 19 | 2.68, m | 59.1 | 20 | 17, 20, 28w, | 20, 21w |
| 20 | 1.22, m | 39.6 | 19, 28 | 17w, 21w, 22', 22" | 19 |
| 21 | 3.20, m | 83.5 | 20, 22', 22" | 20, 22', 22", 23 | 19w, 20w, 23w |
| 22' | 1.64, m | 23.7 | 21w, 22", 23 | 21, 22" | 20, 21, 23 |
| 22" | 1.37, dp (17.0, 6.7, 6.1) | | 22', 23 | 21, 22' | 20, 21, 23 |
| 23 | 0.82, t (7.4) | 10.0 | 22', 22" | 20, 21, 22'w, 22"w | 21, 22 |
| 24 | 1.01, s | 24.8 | | 4'/5', 7 | 5, 6, 7 |
| 25 | 0.71, d (6.8) | 16.4 | 10 | 9w, 10, 11w, 13, 26 | 9, 10, 11 |
| 26 | 1.59, d (1.3) | 11.8 | 13 | 8, 10, 11, 14, 25 | 11, 12, 13, 14w, |
| 27 | 1.14, d (6.8) | 17.0 | 16 | 14, 15, 16, 17 | 15, 16, 17 |
| 28 | 0.87, d (7.1) | 10.8 | 20 | 22', 22" | 19, 20, 21 |
| 29 | | 169.0 | | | |
| 30 | 1.61, s | 20.7 | | | 29 |
| 31 | 3.25, s | 57.7 | | 20w, 22', 22"w, 23w, | 21 |
| 32 | 3.50, s | 58.5 | | 6OH, 17, 31w | 17 |

H. Synthesis of 17-methoxy-17S-FD-895 (1f)

Figure 9A:
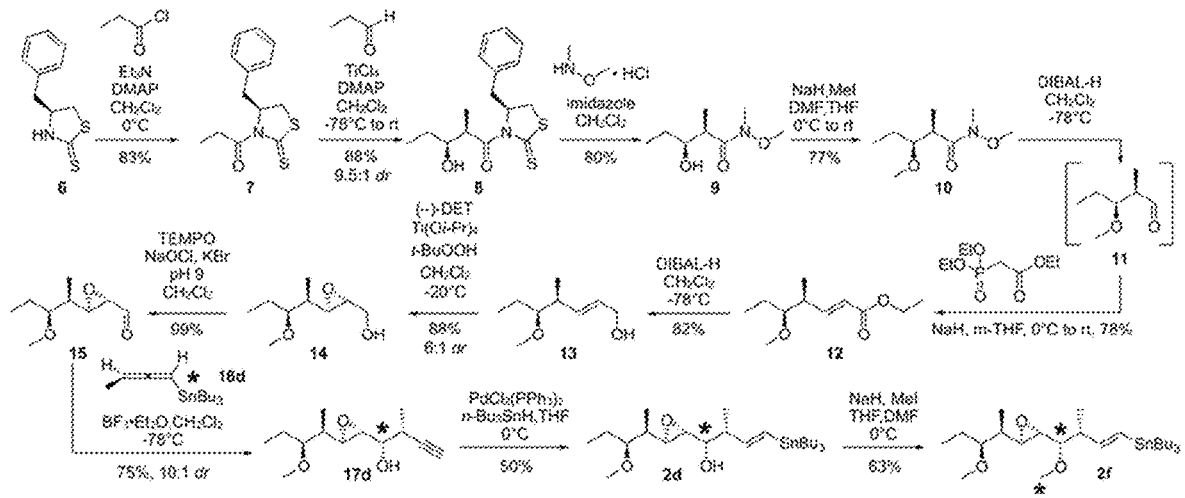
FIGS. 9A to 9C show synthetic scheme of compound 1f (17-methoxy-17S-FD-895) in FIG. 2.
Figure 9B:
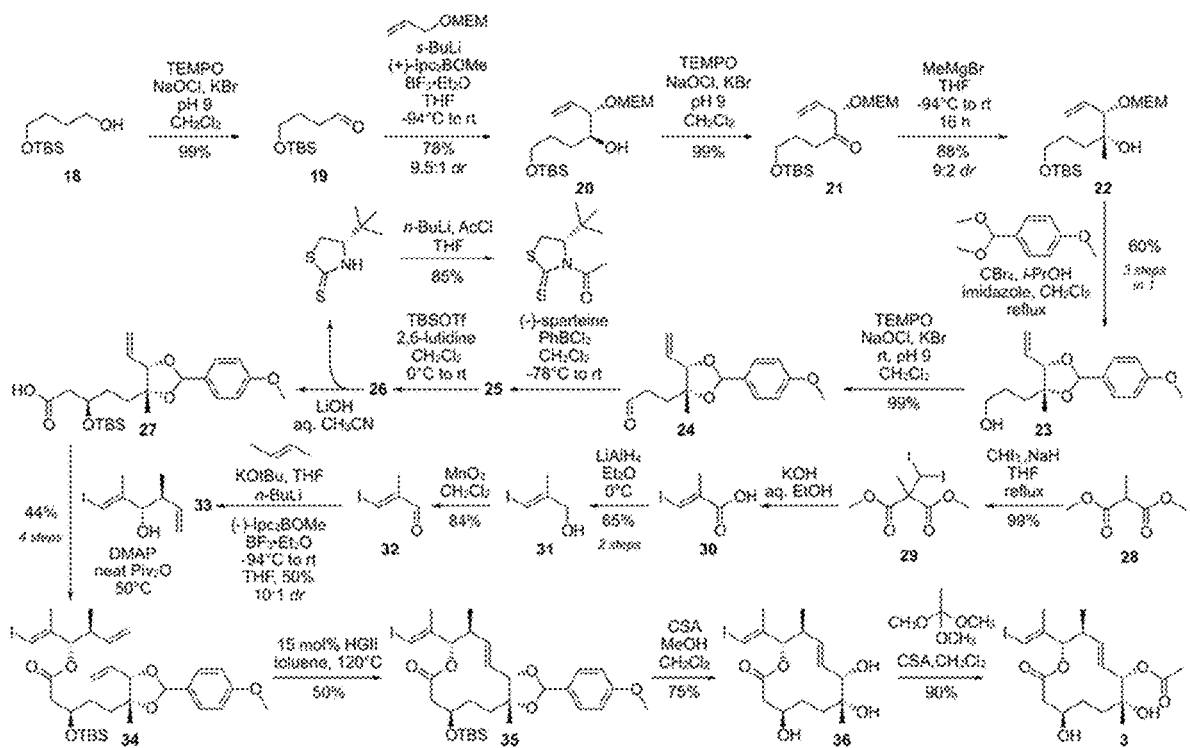
Figure 9C:
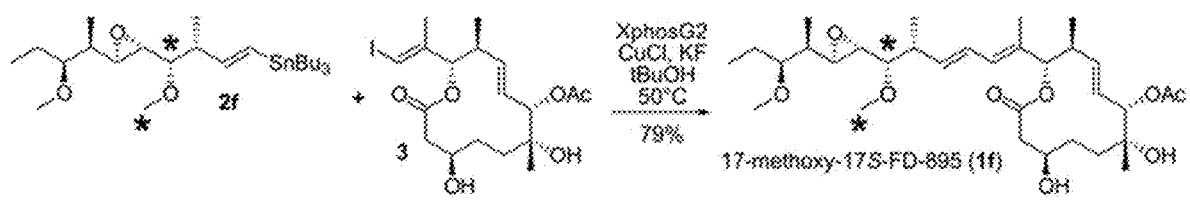

Total synthesis of 17-methoxy-17S-FD-895 (10 is shown in FIG. 9A through 9C. For this study, 1e was prepared from compounds 2f and 3 reported in Chan 2020. Updated procedures are provided for this step. Asterisks (*) denote the compounds that differ from that used to prepare FD-895 (1).

Methylation of Stannane 2d to Afford Stannane 2f

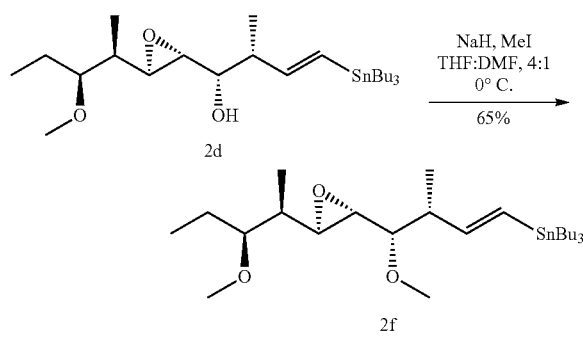

Reagents:
NaH, 60% in mineral oil (Alfa Aesar): used without further purification MeI, 98% (Sigma-Aldrich): used without further purification Tributyl(3R,4R,E)-4-methoxy-44(2S,3R)-3-((2R,3S)-3-methoxypentan-2-yl)oxiran-2-yl)-3-methylbut-1-en-1-yl)stannane (2f). MeI (0.0586 mL, 0.941 mmol) was added at rt to a solution of stannane 2d (50.0 mg, 0.0941 mmol) in a mixture of anhydrous THF (10 mL) and anhydrous DMF (3 mL) in a 50 mL flask. The mixture was cooled to 0° C. and NaH (60% in mineral oil, 8.85 mg, 0.221 mmol) was added in portions ensuring the mixture remained at 0° C. The mixture was slowly warmed to rt and stirred for 16 h. After cooling the mixture to 0° C., a solution of phosphate buffered saline pH 7 (5 mL) was added dropwise. The volatiles were concentrated on a rotary evaporator. The mixture was extracted with hexane (3×50 mL). The combined organic phases were washed with brine, dried over $Na_2SO_4$, filtered and concentrated on a rotary evaporator. Pure stannane 2f (31.5 mg, 65%) was obtained as a colorless oil by flash chromatography, eluting with a gradient of hexanes to 10% $Et_2O$/hexanes.

Vinylstannane 2f: TLC (1:10 $Et_2O$/hexanes): $R_f$=0.50 (CAM stain); $^1H$ NMR (500 MHz, $C_6D_6$) δ6.39 (dd, J=19.1, 6.8 Hz, 1H), 6.26 (d, J=19.1 Hz, 1H), 3.25 (s, 3H), 3.23 (s, 3H), 3.21 (m, 1H), 3.04 (dd, J=4.4, 2.3 Hz, 1H), 2.83 (m, 2H), 2.75 (dd, J=4.4, 2.3 Hz, 1H), 1.61 (m, 8H), 1.39 (m, 8H), 1.19 (d, J=6.9 Hz, 3H), 1.01 (d, J=7.1 Hz, 3H), 1.00 (d, J=8.1 Hz, 3H), 0.95 (t, J=7.4 Hz, 12H), 0.84 (t, J=7.4 Hz, 3H); $^{13}$C NMR (125 MHz, $C_6D_6$) δ150.7, 127.5, 84.7, 83.3, 59.7, 58.3, 57.6, 57.4, 45.3, 39.4, 29.4, 27.5, 23.5, 16.7, 13.8, 10.3, 9.8, 9.5; FTIR (film) $v_{max}$ 3454, 3310, 2973, 2937, 2890, 1459, 1101, 840 cm$^{-1}$; HR-ESI-MS m/z calcd. for C25H$_{50}$O$_3$Sn [M+H]$^+$533.2998, found 533.2994; [α]$^{25}$$_D$=−8.6° (c=1.0, CH$_2$Cl$_2$).

Stille Coupling of Stannane 2f and Core 3 to Afford 17S—O-Methyl-FD-895 (10.

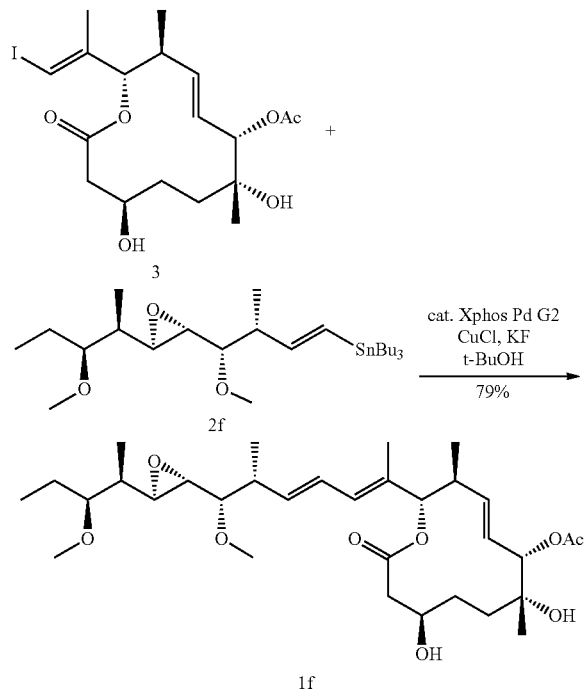

Reagents:

CuCl, anhydrous, beads, 99.99% (Sigma-Aldrich): beads were powdered prior to addition KF, anhydrous, powder, 99.9% (Sigma-Aldrich): used without further purification XPhos Pd G2 (Sigma-Aldrich): used without further purification t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

17-O-Methyl-FD-895 (1f): Yield: 81%, 4.21 mg; TLC (1:3 acetone/hexanes): R$_f$=0.40 (CAM stain); NMR data provided in Table S9; FTIR (film) $v_{max}$ 3447, 2963, 2930, 2875, 1739, 1457, 1374, 1239, 1176, 1089, 1021 cm$^{-1}$; HR-ESI-MS m/z calcd. for C$_{31}$H$_{50}$IO$_9$Na [M+Na]$^+$: 603.7642, found 603.7643; [α]$^{25}$$_D$=+36.9° (c=1.0, CH$_2$Cl$_2$).

TABLE 7

NMR data for 17S-O-Me-FD-895 (1f) in $C_6D_6$

| Position | $^1$H, δ$_H$, mult (J in Hz) | δ$_C$ | $^1$H-COSY | $^1$H, $^1$H-NOSEY | $^1$H, $^{13}$C-HMBC |
|---|---|---|---|---|---|
| 1 | | 172.1 | | | |
| 2' | 2.29, dd (14.8, 3.8) | 38.6 | 2", 3 | 3, 4'w | 1, 3, 4w |
| 2" | 2.20, dd (14.8, 3.0) | | 2', 3 | 3, 5' | 1 |
| 3 | 3.48, m | 69.3 | 2'w, 2"w, 3OH | 2', 2", 4', 5" | |
| 3-OH | 3.62, d (11.1) | | 3 | 3, 6OH | |
| 4' | 1.57, m | 30.4 | 3, 4", 5', 5" | 3, 5", 7, 8 | 5, 6, 3, 24 |
| 4" | 1.26, m | | 4', 5', 5" | 2", 3, 5", 9 | 3 |
| 5' | 1.54, m | 35.9 | 4', 4", 5" | 2", 4", 8 | 4, 6, 24 |
| 5" | 1.18, m | | 4', 4", 5' | 4' | 6, 7 |
| 6 | | 73.6 | | | |
| 6-OH | 1.77, s | | | | |
| 7 | 5.24, d (5.5) | 79.2 | 8 | 4"/5", 8, 9, 24w, 26 | 8w, 9, 24w, 29 |
| 8 | 5.82, dd (15.2, 9.8) | 126.4 | 7, 9 | 4'/5', 7w, 9, 10, 13w | 6w, 9w, 10 |
| 9 | 5.62, dd (15.1, 10.9) | 140.7 | 8, 10 | 4"/5", 7, 8, 10, 11, | 7, 8w, 10, 25 |
| 10 | 2.39, tq (10.4, 6.8) | 41.1 | 9, 11, 25 | 8, 9w, 25, 26 | 8, 9w, 11, 12, 25 |
| 11 | 5.26, d (6.3) | 82.6 | 10 | 10, 13, 25, 26 | 1, 9, 10, 13, 25w, |
| 12 | | 131.7 | | | |
| 13 | 6.12, dd (10.9, 1.5) | 131.4 | 14, 26 | 8w, 11, 14, 15, 25, | 11, 15, 26 |
| 14 | 6.23, ddd (15.1, 10.9, | 125.7 | 13, 15 | 8w, 13, 15, 16, 26 | 13w, 16 |
| 15 | 5.64, dd (15.2, 10.2) | 138.7 | 14, 16 | 13, 14, 16, 17 | 12, 13, 14w, 16, |
| 16 | 2.48, dq (14.4, 7.0) | 42.6 | 15, 17, 27 | 14, 15, 17w, 27w, | 14, 15, 17, 18, 27 |
| 17 | 2.62, t (7.1) | 86.2 | 16, 18 | 15w, 16, 20, 32 | 15, 16, 18, 27, 32 |
| 17-OH | | | | | |
| 18 | 2.68, m | 60.6 | 17 | 15, 16, 20, 32 | 17, 19w, 20 |
| 19 | 2.68, m | 59.1 | 20 | 17, 20, 28w, | 20, 21w |
| 20 | 1.22, m | 39.6 | 19, 28 | 17w, 21w, 22', 22" | 19 |
| 21 | 3.20, m | 83.5 | 20, 22', 22" | 20, 22', 22", 23 | 19w, 20w, 23w |

TABLE 7-continued

NMR data for 17S-O-Me-FD-895 (1f) in $C_6D_6$

| Position | $\delta_H$, mult (J in Hz) | $\delta_C$ | $^1$H, $^1$H-COSY | $^1$H, $^1$H-NOSEY | $^1$H, $^{13}$C-HMBC |
|---|---|---|---|---|---|
| 22' | 1.64, m | 23.7 | 21w, 22'', 23 | 21, 22'' | 20, 21, 23 |
| 22'' | 1.37, dp (17.0, 6.7, | | 22', 23 | 21, 22' | 20, 21, 23 |
| 23 | 0.82, t (7.4) | 10.0 | 22', 22'' | 20, 21, 22'w, 22''w | 21, 22 |
| 24 | 1.01, s | 24.8 | | 4'/5', 7 | 5, 6, 7 |
| 25 | 0.71, d (6.8) | 16.4 | 10 | 9w, 10, 11w, 13, 26 | 9, 10, 11 |
| 26 | 1.59, d (1.3) | 11.8 | 13 | 8, 10, 11, 14, 25 | 11, 12, 13, 14w, |
| 27 | 1.14, d (6.8) | 17.0 | 16 | 14, 15, 16, 17 | 15, 16, 17 |
| 28 | 0.87, d (7.1) | 10.8 | 20 | 22', 22'' | 19, 20, 21 |
| 29 | | 169.0 | | | |
| 30 | 1.61, s | 20.7 | | | 29 |
| 31 | 3.25, s | 57.7 | | 20w, 22', 22''w, | 21 |
| 32 | 3.50, s | 58.5 | | 6OH, 17, 31w | 17 |

I. Synthesis of 3S,17S-FD-895 (1g)

Figure 10A:
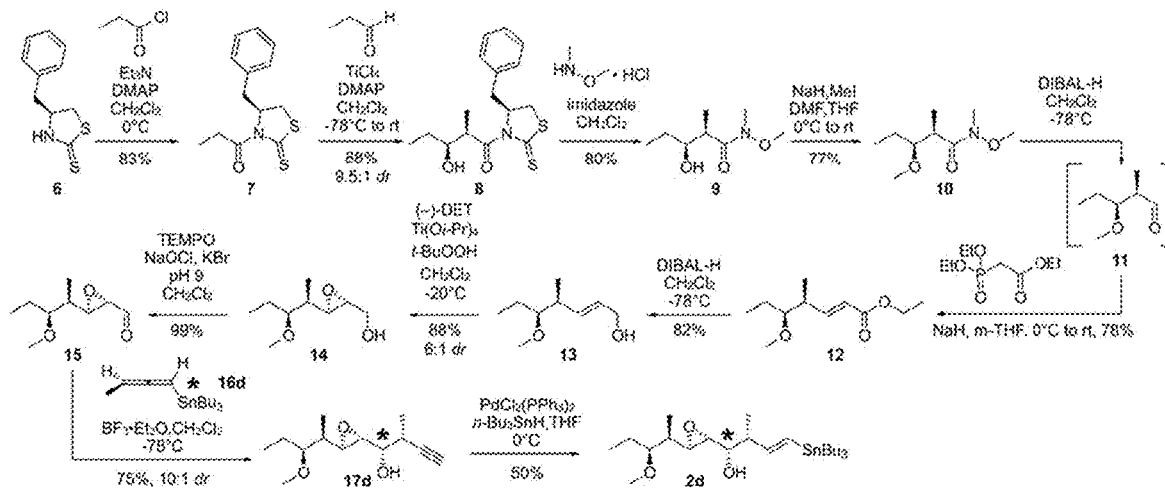
FIGS. 10A to 10C show synthetic scheme of compound 1g (3S, 17S-FD-895) in FIG. 2.
Figure 10B:
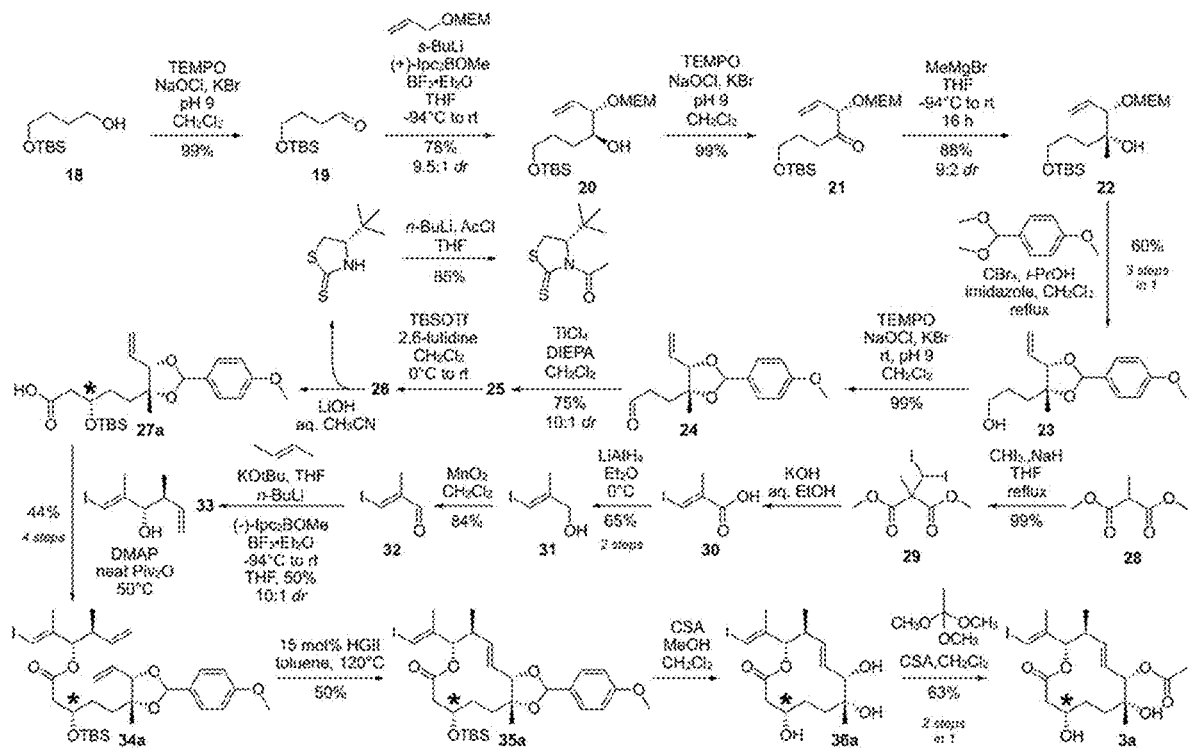
Figure 10C:
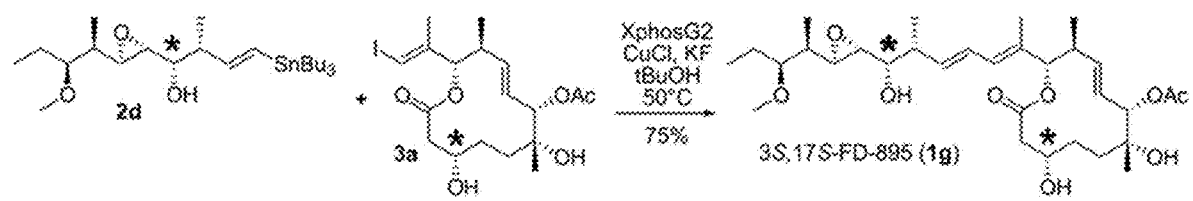

Total synthesis of 3S,17S-FD-895 (1g) is shown in FIGS. 10A through 10C. For this study, 1g was prepared from compounds 2d and 3a reported in Chan 2020. Updated procedures are provided for this step. Asterisks (*) denote the compounds that differ from that used to prepare FD-895 (1).

Stille Coupling of Stannane 2d and Core 3a to Afford 3S,17S-FD-895 (1g).

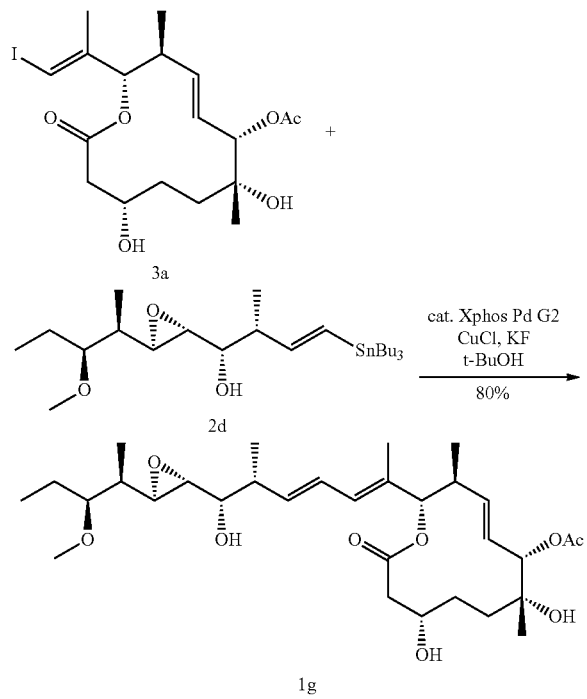

Reagents:
CuCl, anhydrous, beads, 99.99% (Sigma-Aldrich): beads were powdered prior to addition KF, anhydrous, powder, 99.9% (Sigma-Aldrich): used without further purification XPhos Pd G2 (Sigma-Aldrich): used without further purification t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

3S,17S-FD-895 (1g): Yield: 80%, 14.2 mg; TLC (1:3 acetone/$CH_2Cl_2$): $R_f$=0.17 (CAM stain); NMR data provided in Table S7; FTIR (film) $v_{max}$ 3447, 2963, 2930, 2875, 1739, 1457, 1374, 1239, 1176, 1089, 1021 cm$^{-1}$; HR–ESI–MS m/z calcd. for $C_{30}H_{50}O_9Na$ [M+Na]$^+$: 589.3341, found 589.3342; $[\alpha]^{25}_D$=+12.4° (c=1.0, $CH_2Cl_2$).

TABLE 8

NMR data for 3S, 17S-FD-895 (1g) in $C_6D_6$

| Position | $\delta_H$, mult (J in Hz) | $\delta_C$, Type | $^1$H, $^1$H-COSY | $^1$H, $^1$H-NOSEY | $^1$H, $^{13}$C-HMBC |
|---|---|---|---|---|---|
| 1 | | 169.9 | | | |
| 2' | 2.43, dd (13.3, | 40.2 | 2'', 3 | 3w, 5' | 1, 3, 4w |

TABLE 8-continued

NMR data for 3S, 17S-FD-895 (1g) in $C_6D_6$

| Position | $\delta_H$, mult (J in Hz) | $\delta_C$ Type | $^1$H, $^1$H-COSY | $^1$H, $^1$H-NOSEY | $^1$H, $^{13}$C-HMBC |
|---|---|---|---|---|---|
| 2" | 2.30, dd (13.1, 5.4) | | 2', 3 | 3 | 1, 3, 4 |
| 3 | 4.20, m | 67.8 | 2', 2"w | 2'w, 2", 4', 4" | |
| 3OH | | | | | |
| 4' | 1.34 m | 27.6 | 4", 5', 5 " | 3, 5", 7 | |
| 4" | 1.29, m | | 3w, 4', 5'w, | 3, 24 | 2, 3w, 5w |
| 5' | 1.85, td (13.4, 4.0) | 30.9 | 4', 4", 5" | 2', 4", 8 | 4w, 6, 24w |
| 5" | 1.78, td (13.6, 4.8) | | 4', 4", 5' | 4', 4", 24 | 4, 6, 7, 24w |
| 6 | | 73.6 | | | |
| 6OH | 1.92, bs | | | 5", 24 | |
| 7 | 5.25, d (9.8) | 79.3 | 8 | 4', 8, 9, 24 | 8, 9, 29 |
| 8 | 5.91, dd (15.2, 9.8) | 126.5 | 7, 9, 10w | 5', 7, 9, 10 | 6w, 10 |
| 9 | 5.61, dd (15.2, | 140.5 | 8, 10 | 4', 7, 8, 10w, 25 | 7, 10, 25w |
| 10 | 2.47, m | 41.3 | 9, 11, 25 | 8w, 25, 26 | 8, 9, 11, 25w |
| 11 | 5.20, d (10.6) | 82.3 | 10 | 9, 10w, 13, 25, 26w | 1, 9w, 10, 12, |
| 12 | | 131.6 | | | |
| 13 | 6.19, d (10.9, 1.5) | 131.8 | 14, 26w | 11, 15, 25w | 11, 15, 26 |
| 14 | 6.27, ddd (15.1, | 126.6 | 13, 15 | 15, 16, 26, 27 | 12, 13, 16 |
| 15 | 5.81, dd (15.0, 8.4) | 137.6 | 14, 16 | 14, 16, 27 | 12, 13, 16, |
| 16 | 2.36, m | 41.5 | 15, 17w, 27 | 14, 15, 17, 27 | 14, 15, 17w, |
| 17 | 3.44, t (3.4) | 73.0 | 16, 18 | 15, 16, 18, 19, 27 | 15, 16w, 18, |
| 17OH | | | | | |
| 18 | 2.57, dd (3.8, 2.2) | 59.7 | 17, 19 | 17, 20, 27, 28 | 17w |
| 19 | 3.02, dd (8.2, 2.3) | 57.7 | 18, 20 | 17, 20w, 28 | 20 |
| 20 | 1.33, m | 39.2 | 19, 21, 28 | 18, 21, 28 | 18w, 19, 21w, |
| 21 | 3.14, td (6.2, 4.4) | 83.8 | 20, 22', 22" | 20, 22'w, 22", 23 | 19, 20w, 23 |
| 22' | 1.63, m | 23.9 | 21, 22", 23 | 21w, 22", 23 | 20, 21 |
| 22" | 1.41, m | | 21, 22', 23 | 22', 23 | 20, 21, 23 |
| 23 | 0.86, t (7.4) | 10.2 | 22', 22" | 20, 21, 22', 22" | 21, 22 |
| 24 | 1.08, s | 24.8 | | 5", 7 | 5, 6, 7 |
| 25 | 0.73, d (6.8) | 16.5 | 10 | 9, 10, 11 | 9, 10, 11 |
| 26 | 1.61, d (1.3) | 12.0 | 13 | 10, 14 | 11, 12, 13 |
| 27 | 1.12, d (7.0) | 17.3 | 16 | 14, 15, 16, 17, 18w | 15, 16, 17 |
| 28 | 0.89, d (7.0) | 10.9 | 20 | 18w, 19w, 20, 22' | 19, 20, 21 |
| 29 | | 169.4 | | | |
| 30 | 1.64, s | 20.9 | | | 29 |
| 31 | 3.23, s | 57.7 | | 19w, 21, 22", 23 | 21 |

J. Synthesis of 7R,17S-FD-895 (1h)

Figure 11A:
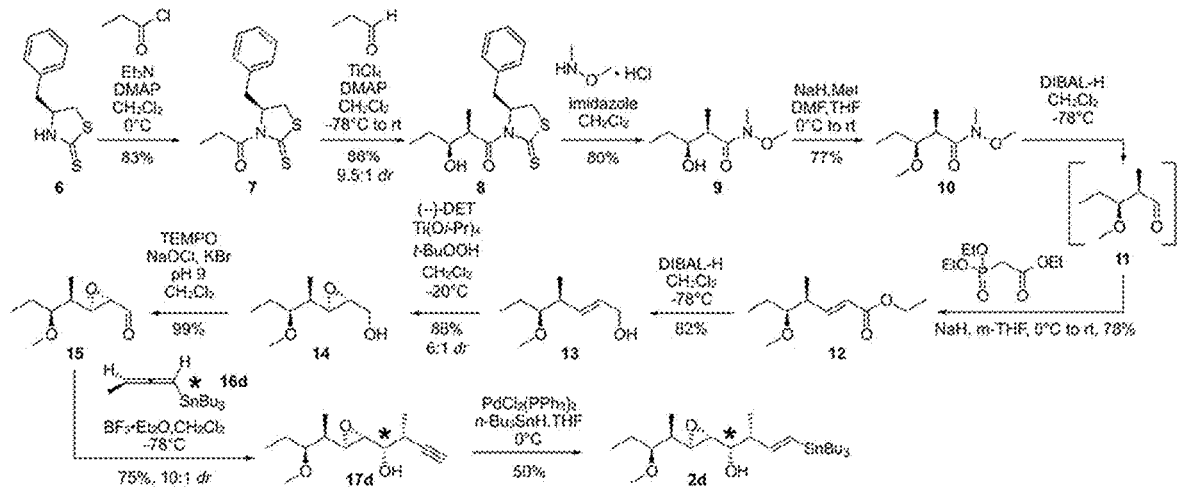
FIGS. 11A to 11C show synthetic scheme of compound 1h (7R, 17S-FD-895) in FIG. 2.
Figure 11B:
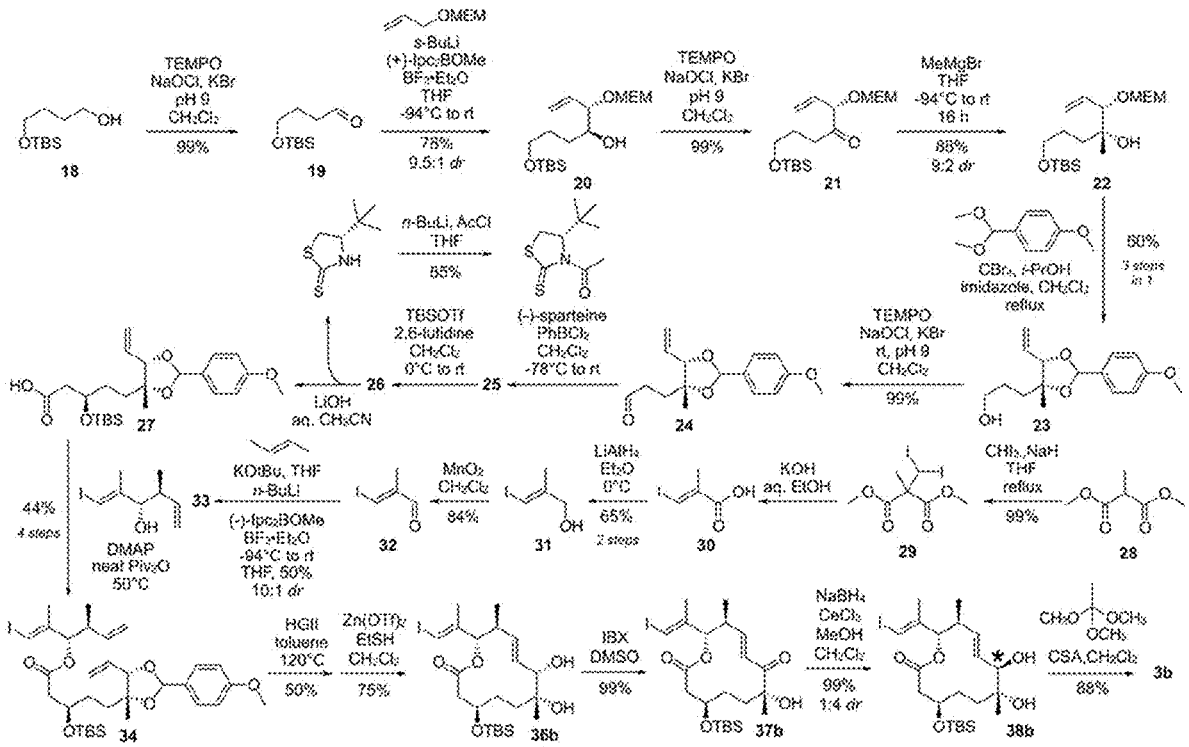
Figure 11C:
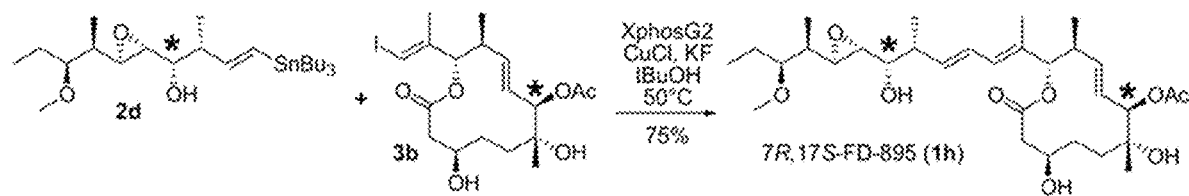

Total synthesis of 7R,17S-FD-895 (1h) is shown in FIGS. 11A through 11C. For this study, 1h was prepared from compounds 2d and 3b reported in Chan 2020. Updated procedures are provided for this step. Asterisks (*) denote the compounds that differ from that used to prepare FD-895 (1).

Stille Coupling of Stannane 2d and 3b to Afford 7R,17S-FD-895 (1h).

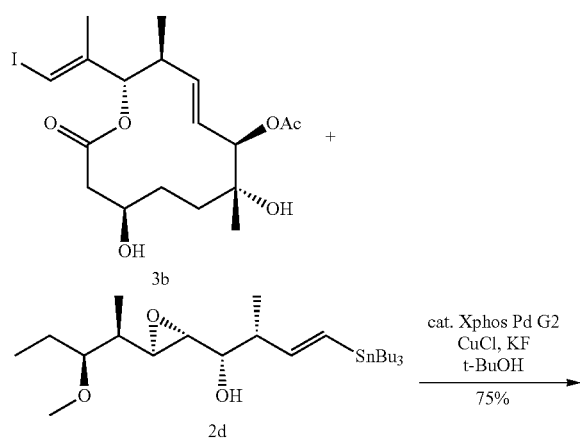

Reagents:
  CuCl, anhydrous, beads, 99.99% (Sigma-Aldrich): beads were powdered prior to addition
  KF, anhydrous, powder, 99.9% (Sigma-Aldrich): used without further purification
  XPhos Pd G2 (Sigma-Aldrich): used without further purification
  t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

7R,17S-FD-895 (1h): Yield: 75%, 5.01 mg; TLC (1:3 acetone/CH$_2$Cl$_2$): R$_f$=0.28 (CAM stain); NMR data provided in Table S8; FTIR (film) $v_{max}$ 3447, 2963, 2930, 2875, 1739, 1457, 1374, 1239, 1176, 1089, 1021 cm$^{-1}$; HR–ESI–MS m/z calcd. for C$_{30}$H$_{50}$O$_9$Na [M+Na]$^+$: 589.3341, found 589.3345; [α]$^{25}_D$=+20.1° (c=1.0, CH$_2$Cl$_2$).

Epoxidation of Alcohol 13

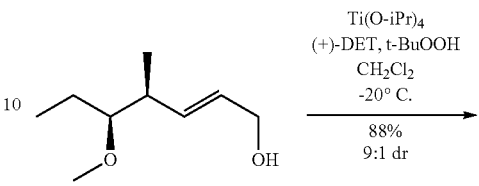

Table 9, NMR Data for 7R,17S-FD-895 (1h) in C$_6$D$_6$

TABLE 9

NMR data for 7R,17S-FD-895 (1h) in C$_6$D$_6$

| Position | $\delta_H$, mutt (J in Hz) | $\delta_C$ | $^1$H, $^1$H-COSY | $^1$H,$^1$-H-NOESY | $^1$H, $^{13}$C-HMBC |
|---|---|---|---|---|---|
| 1 | 4.65, d (9.3) | 172.3 | | | |
| 2' | 2.35, m | 39.3 | 2', 3 | 3, 4"w | 1, 3, 4 |
| 2" | 2.30, dd (14.6, 3.2) | | 2", 3 | 3, 4" | 1, 3, 4w |
| 3 | 3.58, ddt (10.8, 7.4, | 69.6 | 2", w3OH, 4', | 3OH, 4", 17OH, | |
| 3-OH | 3.70, d (10.7) | | 3 | 2', 2", 3, 17OH, 24 | 2w, 3 |
| 4' | 1.80, m | 30.6 | 3, 4", 5', 5" | 3OHw, 5', 7w, 24 | conformers |
| 4" | 1.62, m | | 3w, 4', 5', 5" | 2'w, 5" | conformers |
| 5' | 1.58, m | 36.5 | 4'w, 4", 5" | 4', 5" | conformers |
| 5" | 0.97, m | | 4', 4", 5' | 3w, 4" | conformers |
| 6 | | 73.8 | | | |
| 6-OH | 1.68, bs | | | 3OH, 24 | |
| 7 | 5.41, m | 82.9 | 8 | 8, 10w, 24, 26 | 5, 6, 8, 9, |
| 8 | 5.93, dd (15.3, 2.5) | 127.9 | 7, 9 | 4"/5', 7, 9, 10 | 7, 10 |
| 9 | 5.39, m | 130.7 | 8, 10 | 4', 8, 10, 25 | 7, 8, 10 |
| 10 | 2.48, tq (10.3, 6.7) | 41.1 | 11, 25 | 8, 9w, 25, 26 | 8, 9, 11, |
| 11 | 5.36, d (10.6) | 78.0 | 10 | 10w, 13, 25, 26w | 1, 10, 12, |
| 12 | | 131.6 | | | |
| 13 | 6.17, d (10.7) | 131.6 | 14, 26w | 11, 14, 15, 16, 25, | 11, 15, 26 |
| 14 | 6.29, dd (15.1, 10.8) | 126.4 | 13, 15 | 15, 16, 26, 27 | 12, 13, 16 |
| 15 | 5.80, dd (15.1, 8.4) | 137.8 | 14, 16 | 13, 14, 16, 17w, 27 | 12, 13, 14, |
| 16 | 2.38, m | 41.5 | 15, 17, 27 | 14, 15w, 17, 18,27 | 14, 15, 17, |
| 17 | 3.43, m | 72.8 | 16, 17OH, 18 | 15, 16, 17OH, 18, | 15, 18, 19 |
| 17-OH | 1.67, m | | 17 | 3, 3OH, 24 | |
| 18 | 2.57, dd (3.8, 2.3) | 59.6 | 17 | 15, 17, 20, 27, 28 | 17 |
| 19 | 3.02, dd (8.2, 2.2) | 57.6 | 20 | 17, 17OH, 20, 28 | 17w, 18w, |
| 20 | 1.33, m | 39.0 | 19, 28 | 18, 21, 23 | 19, 28 |
| 21 | 3.15, m | 83.7 | 20, 22', 22" | 22', 22", 23 | 19, 20, |
| 22' | 1.63, m | 23.8 | 21, 22", 23 | 20w, 22" | 20, 21, 23 |
| 22" | 1.40, dp (14.2, 7.3) | | 21, 22', 23 | 22', 23 | 20, 21, 23 |
| 23 | 0.85, t (7.4) | 10.0 | 22', 22" | 20, 21, 22'w, 22" | 21, 22 |
| 24 | 1.02, s | 24.7 | | 3, 3OH, 6OH, | 7, 5, 6, 7 |
| 25 | 0.77, d (6.8) | 16.9 | 10 | 9, 10, 11, 26w | 9, 10, 11 |
| 26 | 1.64, d (1.2) | 11.9 | | 10, 14 | 11, 12, 13 |
| 27 | 1.12, d (7.0) | 17.3 | 16 | 14w, 15w, 16, 17 | 15, 16, 17 |
| 28 | 0.89, d (7.0) | 10.8 | 20 | 18, 19, 20, 21 | 19, 20, 21 |
| 29 | | 169.3 | | | |
| 30 | 1.68, s | 20.4 | | | 29 |
| 31 | 3.24, s | 57.7 | | 22', 22", 23 | 21 |

K. Synthesis of 17S,18S,19S-FD-895 (1i)

Figure 12A:
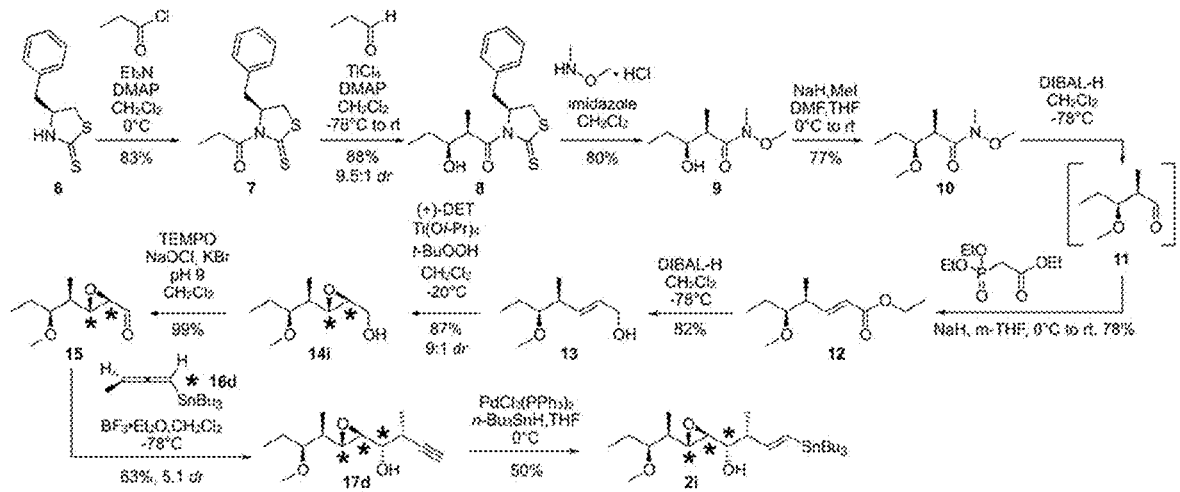
FIGS. 12A to 12C show synthetic scheme of compound 1i (17S, 18S, 19S-FD-895) in FIG. 2.
Figure 12B:
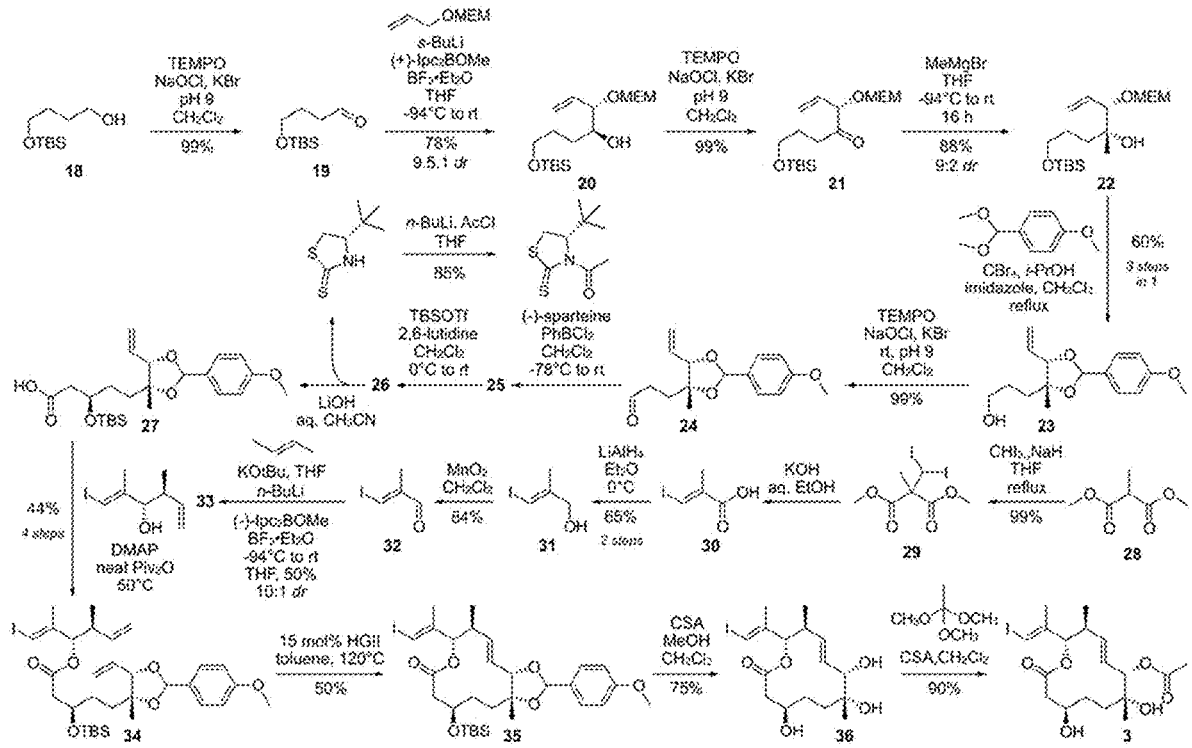
Figure 12C:
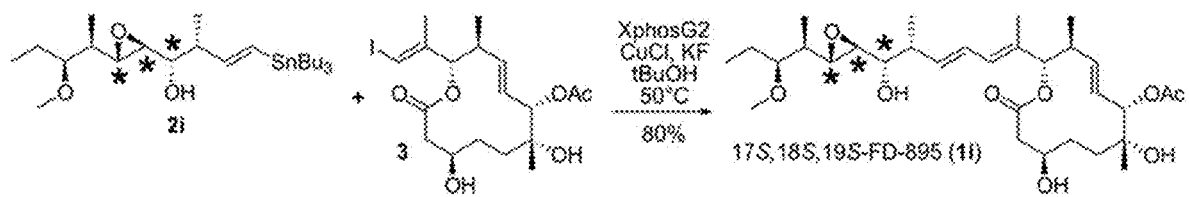

Total synthesis of 17S,18S,19S-FD-895 (1i) is shown in FIGS. 12A through 12C. For this study, 1i was prepared from compounds 13 and 2 reported in Chan 2020. Updated procedures are provided for this step. Asterisks (*) denote the compounds that differ from that used to prepare FD-895 (1).

-continued

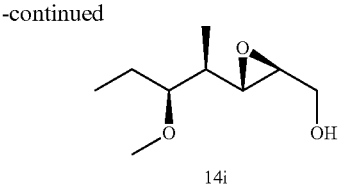

Reagents:
Ti(Oi-Pr)$_4$, 97% (Sigma-Aldrich): vacuum distilled at 90° C., 5 mbar
(−)-Diethyltartrate, 99% (Alfa Aesar): used without further purification
t-Butylhydroperoxide, 3.3 M in toluene: dried from a 70% solution in water according to methods developed by the Sharpless laboratory ((2S,3S)-3-((2R,3S)-3-Methoxypentan-2-yl)oxiran-2-yl)methanol (14i). t-Butylhydroperoxide (3.3 M, 19.2 mL, 65.1 mmol) was added to a 500 mL flask containing a stirring solution of Ti(Oi-Pr)$_4$ (0.650 mL, 3.15 mmol), (−)-diethyl tartrate (0.550 mL, 3.15 mmol) and powdered 4A molecular sieves (1 g) in anhydrous CH$_2$Cl$_2$ (100 mL). The mixture was cooled to −20° C. and stirred for 30 min. A solution of alcohol 13 (5.0 g, 31.9 mmol) in CH$_2$Cl$_2$ (25 mL) was added dropwise. The reaction was stirred at −20° C. for 4 h. The reaction was quenched via addition of 10% NaOH (10 mL). The mixture was then extracted into CH$_2$Cl$_2$ and concentrated on a rotary evaporator. Pure epoxyalcohol 14i (5.50 g, 88%) was obtained as a 6:1 mixture of diastereomers by flash chromatography, eluting with a gradient of hexanes to 1:1 EtOAc/hexanes.

Note 1: Diastereomers were not Separable and Carried on Directly to the Next Step.

Epoxyalcohol 14i: TLC (1:2 EtOAc/hexanes): R$_f$=0.10 (CAM stain); $^1$H NMR (500 MHz, C$_6$D$_6$) δ3.59 (tq, J=15.9, 12.6, 2.7 Hz, 1H), 3.37 (m, 12.0, 7.1, 4.4 Hz), 3.02 (s, 3H), 2.77 (dd, J=7.1, 2.3 Hz, 1H), 2.74 (dd, J=4.7, 2.5 Hz, 1H), 2.70 (dt, J=7.3, 4.8 Hz, 1H), 2.36 (t, J=6.1 Hz, 1H), 1.44 (m, 1H), 1.37 (m, 1H), 1.30 (dtd, J=14.0, 7.5, 5.2 Hz, 1H), 0.96 (d, J=7.0 Hz, 3H) 0.77 (t, J=7.4 Hz, 3H); $^{13}$C NMR (125 MHz, C$_6$D$_6$) δ83.8, 62.2, 58.0, 57.9, 57.7, 38.8, 24.0, 10.4, 10.1; FTIR (film) ν$_{max}$ 3422, 2972, 2930, 2879, 1468, 1103 cm$^{-1}$; HR–ESI–MS m/z calcd. for C$_9$H$_{18}$O$_3$ [M]$^+$: 174.1250, found 174.1249; [α]$^{25}$$_D$=+182.4° (c=1.0, CHCl$_3$).

Oxidation of Epoxyalcohol 14i

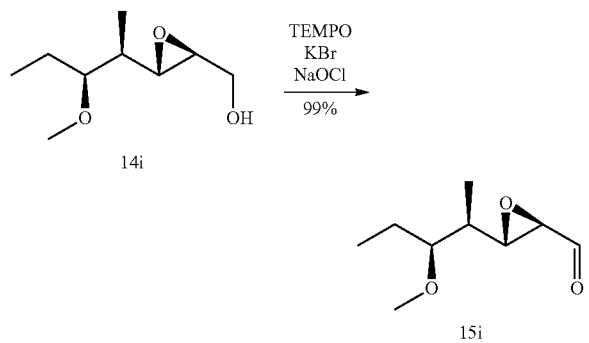

Reagents:
TEMPO, 99% (Oakwood Chemical): used without further purification
KBr, (Spectrum Chemical Mfg. Corp.): used without further purification
NaOCl, 2 M, 10-15% active chlorine (Spectrum Chemical Mfg. Corp.): used without further purification (2R,3S)-3-((2R,3S)-3-Methoxypentan-2-yl)oxirane-2-carbaldehyde (15i). A solution of KBr (0.242 g, 2.04 mmol) in H$_2$O (10 mL), satd. NaHCO$_3$ (20 mL) and TEMPO (0.266 g, 1.70 mmol) were added sequentially to a 500 mL flask containing a solution of epoxyalcohol 14i (4.42 g, 25.4 mmol) in CH$_2$Cl$_2$ (150 mL). The mixture was cooled to 0° C. and a solution of NaOCl (2 M, 17 mL, 34.0 mmol) and satd. NaHCO$_3$ (20 mL) were added dropwise via an addition funnel. The mixture was allowed to warm to rt and stirred for 2 h. The phases were separated, and the aqueous phase was extracted with CH$_2$Cl$_2$ (3×100 mL). The combined organic phases were washed with brine (100 mL), dried over Na$_2$SO$_4$, filtered and concentrated on a rotary evaporator. Aldehyde 15i (4.41 g, 99%) was obtained without further purification and was carried on directly to the next step.

Note 1: Diastereomers Obtained from Epoxidation were not Separable at this Step and Thus Carried Forward.

Aldehyde 15i: TLC (1:2 EtOAc/hexanes): R$_f$=0.55 (CAM stain); $^1$H NMR (500 MHz, C$_6$D$_6$) δ 8.67 (d, J=6.3 Hz, 1H), 2.93 (s, 3H), 2.89 (dd, J=6.4, 2.0 Hz, 1H), 2.82 (dd, J=6.4, 2.0 Hz, 1H), 2.60 (dt, J=7.2, 4.7 Hz, 1H), 1.30 (m, 2H), 1.15 (dqd, J=14.6, 7.4, 5.3 Hz, 1H), 0.75 (d, J=7.0 Hz, 3H), 0.67 (t, J=7.4 Hz, 3H); $^{13}$C NMR (125 MHz, C$_6$D$_6$) δ198.0, 84.2, 58.4, 58.4, 57.3, 37.6, 23.6, 11.4, 10.2; FTIR (film) ν$_{max}$ 2972, 2930, 2879, 2828, 1732, 1468, 1103 cm$^{-1}$; HR–ESI–MS m/z calcd. for C$_9$H$_{16}$O$_3$ [M+H]$^+$: 173.1172, found 173.1174; [α]$^{25}$D=+36.1° (c=1.0, CH$_2$Cl$_2$).

Marshall Addition of Allenylstannane 16 to Aldehyde 15

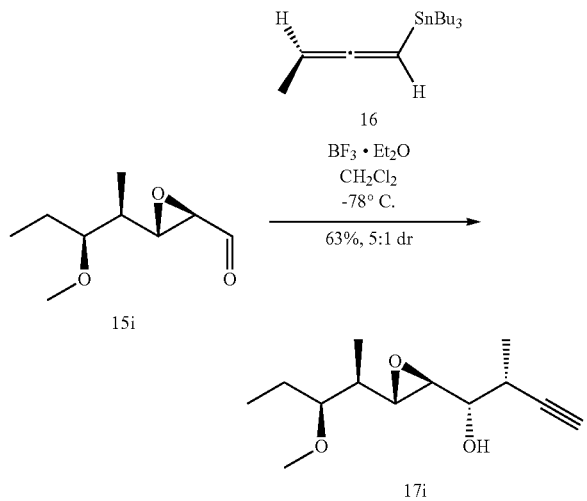

Reagents:
BF$_3$·Et$_2$O, 46.5% BF$_3$ (Alfa Aesar): used without further purification (1R,2R)-1-((2S,3S)-3-((2R,3S)-3-methoxypentan-2-yl)oxiran-2-yl)-2-methylbut-3-yn-1-ol (17i). Aldehyde 15i (70.1 mg, 0.408 mmol) and allenylstannane 16 (0.210 g, 0.610 mmol) in a 50 mL flask were dissolved in anhydrous CH$_2$Cl$_2$ (10.0 mL) and purged with an Ar atmosphere. The mixture was cooled to −78° C. and BF$_3$·Et$_2$O (75.3 µL, 0.610 mmol) was added dropwise over 5 min. The reaction was stirred for 1 h at −78° C. A mixture of MeOH (5 mL) and satd. NaHCO$_3$ (1 mL) was added, and the solution was warmed to rt. The phases were separated, and the aqueous phases were extracted with Et$_2$O (3×50 mL). The organic phases were combined, dried with Na$_2$SO$_4$ and concentrated on a rotary evaporator. Alkyne 17i (69.2 mg, 63%) was obtained in a 5:1 mixture of diastereomers (by NMR) as a colorless oil by flash chromatography, eluting with a gradient of hexanes to 1:3 Et$_2$O/hexanes.

Alkyne 17i: TLC (2:1 hexanes/EtOAc): R$_f$=0.40; $^1$H NMR (500 MHz, C$_6$D$_6$) δ 3.55 (td, J=8.3, 7.6, 4.4 Hz, 1H), 3.18 (q, J=2.7 Hz, 1H), 3.14 (s, 3H), 3.03 (ddd, J=6.8, 4.6, 2.3 Hz, 1H), 2.92 (dt, J=7.5, 4.8 Hz, 1H), 2.55 (dqd, J=10.0, 7.1, 3.4 Hz, 1H), 1.86 (m, 1H), 1.54 (m, 2H), 1.39 (m, 1H), 1.30 (d, J=7.1 Hz, 3H), 1.06 (d, J=6.8 Hz, 3H), 0.83 (t, J=7.3

Hz, 3H); $^{13}$C NMR (125 MHz, C$_6$D$_6$) δ 85.4, 84.6, 71.9, 71.2, 59.0, 58.9, 57.4, 57.3 38.4, 31.0, 23.7, 17.4, 12.2, 10.3; ESI-MS m/z 249.14 [M+Na]$^+$; FTIR (film) vmax 3430, 3310, 2967, 2935, 2878, 1457, 1379, 1260, 1093 cm$^{-1}$; HR-ESI-MS m/z calcd. for C$_{13}$H$_{22}$O$_3$Na [M+Na]$^+$: 249.1461, found 249.1462. [α]$^{25}$D=+24.2° (c=1.0, CH$_2$Cl$_2$).

Hydrostannylation of Alkyne 17i

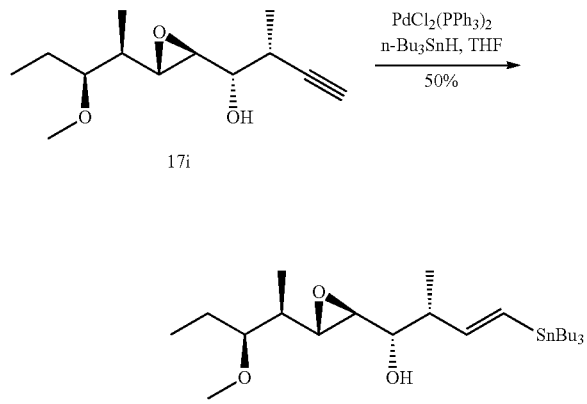

Reagents:
- n-Bu$_3$SnH, 97% contains 0.05% BHT as stabilizer (Acros Organics): used without further purification
- PdCl$_2$(PPh$_3$)$_2$ (Oakwood Chemical): dried via azeotropic distillation of benzene (1R,2R,E)-1-((2R,3R)-3-((2R,3S)-3-Methoxypentan-2-yl)oxiran-2-yl)-2-methyl-4-(tributylstannyl)but-3-en-1-ol (2). PdCl$_2$(PPh$_3$)$_2$ (15.5 mg, 0.0221 mmol) was added to a solution of alkyne 17i (50.1 mg, 0.221 mmol) in a 10 mL flask in anhydrous THF (5 mL). The mixture was cooled to 0° C. and n-Bu$_3$SnH (0.179 mL, 0.663 mmol) was added dropwise. The mixture was stirred for 45 min at 0° C., at which point the resulting mixture was concentrated to yield a black crude oil. The material was extracted into hexanes, filtered through a pad of Celite and was eluted with hexanes. The eluant was concentrated on a rotary evaporator, and this process was repeated twice until a clear black solution was achieved. Pure vinylstannane 2 (22.0 mg, 50%) was obtained as a mixture of 1:5 α:β regioisomers by flash chromatography, eluting with a gradient of hexanes to CH$_2$Cl$_2$ to 1:20 Et$_2$O/CH$_2$Cl$_2$. The desired regioisomer and diastereomer can be obtained in 95+% purity by additional flash chromatography, eluting with a gradient of hexanes to CH$_2$Cl$_2$ to 1:20 Et$_2$O/CH$_2$Cl$_2$.

Vinylstannane 2i: TLC (10:1 hexanes/Et$_2$O): R$_f$=0.25 (CAM stain); $^1$H NMR (C$_6$D$_6$, 500 MHz) δ 6.16 (m, 2H), 3.54 (m, 1H), 3.16 (s, 3H), 3.07 (d, J=7.2, Hz, 1H), 2.93 (m, 2H), 2.49 (m, 2H), 1.98 (s, 1H), 1.60 (m, 9H), 1.39 (dt, J=15.5, 8.5 Hz, 6H), 1.28 (d, J=7.0 Hz, 3H), 1.07 (d, J=6.9 Hz, 3H), 0.96 (m, 12H), 0.87 (t, J=7.4 Hz, 3H); $^{13}$C NMR (C$_6$D$_6$, 500 MHz) δ 151.5, 84.8, 72.7, 59.4, 57.4, 46.5, 38.4, 29.6, 27.7, 23.8, 16.2, 14.0, 12.2, 10.5, 9.8; HR-ESI-MS m/z calcd. for C$_9$H$_{17}$O$_3$[M+H]$^+$519.2843, found 519.2839; [α]$^{25}$D=+10.1° (c=1.0, CH$_2$Cl$_2$).

Stille Coupling of Stannane 2i and Core 3 to Afford 17S, 18S,19S-FD-895 (1i).

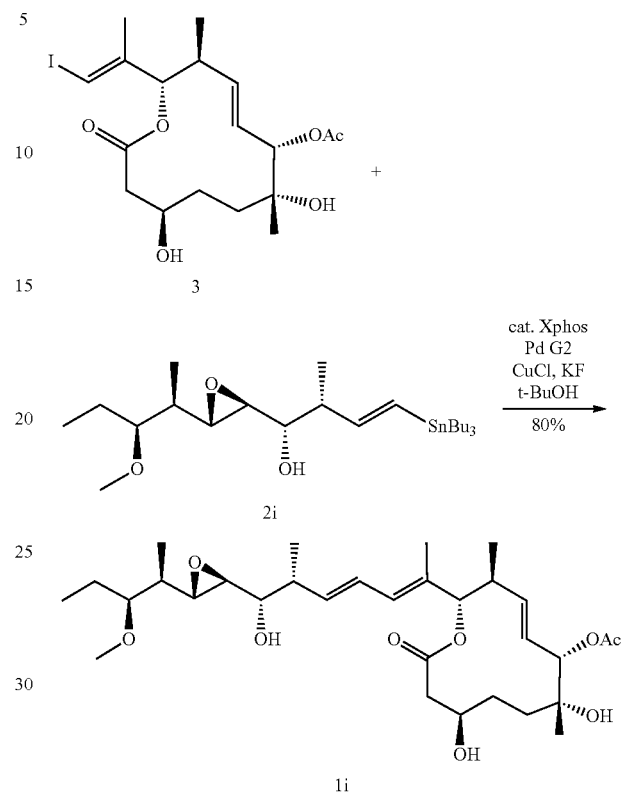

Reagents:
- CuCl, anhydrous, beads, 99.99% (Sigma-Aldrich): beads were powdered prior to addition
- KF, anhydrous, powder, 99.9% (Sigma-Aldrich): used without further purification
- XPhos Pd G2 (Sigma-Aldrich): used without further purification
- t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

17S,18S,19S-FD-895 (1i): Yield: 80%, 7.24 mg; TLC (1:3 acetone/CH$_2$Cl$_2$): R$_f$=0.28 (CAM stain); NMR data provided in Table S10; FTIR (film) v$_{max}$ 3447, 2963, 2930, 2875, 1739, 1457, 1374, 1239, 1176, 1089, 1021 cm$^{-1}$; HR-ESI-MS m/z calcd. for C$_{31}$H$_{50}$IO$_9$Na [M+Na]$^+$: 589.3345, found 589.3347; [α]$^{25}$D=+4.2° (c=1.0, CH$_2$Cl$_2$).

TABLE 10

| | | | | ¹H, | ¹H, |
|---|---|---|---|---|---|
| Position | $\delta_H$, mult (J in Hz) | $\delta_C$ | ¹H-COSY | ¹H, ¹H-NOSEY | ¹³C-HMBC |
| 1 | | 172.1 | | | |
| 2' | 2.31, dd (14.8, 3.8) | 38.5 | 2', 3 | 3w | 1, 3, 4 |
| 2" | 2.22, dd (14.8, 2.8) | | 2", 3 | 3w, 4'/5' | 1 |
| 3 | 3.52, m | 69.3 | 2', 2", 4'w, | 2", 4'/5'w, 5" | |
| 3-OH | | | 3 | 3, 24, 30 | |
| 4' | 1.58, m | 30.2 | 4", 5', 5" | 2", 5", 24 | 3w, 4w, 6, 24 |
| 4" | 1.33, m | | 3, 4' | 4', 5' | 3, 5 |
| 5' | 1.55, m | 35.8 | 4'w, 4", 5" | 2", 4', 8w | 4, 6, 24w |
| 5" | 1.27, m | | 4' | 7 | 4, 6, 7, 24w |
| 6 | | 73.3 | | | |
| 6-OH | | | | 3OH, 24 | |
| 7 | 5.25, d (10.6) | 79.2 | 8 | 4'/5', 5", 8w, 9, 24 | 8, 9, 24, 29 |
| 8 | 5.83, dd (15.2, 9.8) | 126.5 | 7, 9 | 4'/5', 7, 9, 10 | 6w, 10 |
| 9 | 5.64, (15.2, 10.0) | 140.6 | 8, 10 | 5", 8, 10, 11, 25 | 7, 10, 11w, |
| 10 | 2.41, m | 41.0 | 9, 11, 25 | 7w, 8, 25, 26 | 8, 9, 11, 25 |
| 11 | 5.27, d (11.1) | 82.6 | 10 | 10, 13, 25 | 1, 9, 10, |
| 12 | | 131.7 | | | |
| 13 | 6.17, d (10.9) | 131.3 | 14, 26w | 11, 14, 15, 25 | 11, 14, 15, |
| 14 | 6.32, dd (15.1, 10.8) | 126.1 | 13, 15 | 13, 15, 16, 26, 27 | 12, 13, 16 |
| 15 | 5.75, dd (15.1, 8.2) | 138.4 | 14, 16 | 13, 14, 16, 17w, 18w, | 12, z13, 16, |
| 16 | 2.44, m | 41.8 | 15, 17, 27 | 14, 15, 17, 27 | 14, 15, 17, |
| 17 | 3.48, dd (6.6, 3.6) | 72.6 | 16, 18 | 15, 16, 18, 19w, 27 | 15w, 16w, |
| 17-OH | | | | | |
| 18 | 2.78, dd (3.6, 2.3) | 59.2 | 17 | 15w, 16, 17, 20, 27, 28 | 17 |
| 19 | 3.01, dd (7.4, 2.2) | 57.3 | 20 | 17, 20, 28 | 18w, 20, 28 |
| 20 | 1.52, m | 38.0 | 19, 28 | 18, 19w, 21, 28 | 19, 28 |
| 21 | 2.83, dt (7.5, 4.6) | 84.7 | 20w, 22' | 20, 22', 22"w, 23, 28, | 23, 31 |
| 22' | 1.49, m | 23.5 | 21, 22", 23 | 21w, 23w | 20, 21, 23 |
| 22" | 1.38, m | | 23 | 21w, 23w | 20w, 21w, |
| 23 | 0.83, t (7.4) | 10.6 | 22', 22" | 21, 22'w, 22" | 21, 22 |
| 24 | 1.02, s | 24.7 | | 4'/5', 7 | 5, 6, 7 |
| 25 | 0.72, d (6.8) | 16.4 | 10 | 9, 10, 11, 26w | 9, 10, 11 |
| 26 | 1.61, d (1.3) | 11.8 | 13 | 10, 11w, 14 | 11, 12, 13, |
| 27 | 1.20, d (6.9) | 16.3 | 16 | 14, 15, 16, 17, 18w | 15, 16, 17 |
| 28 | 1.02, d (6.9) | 12.4 | 20 | 20, 21 | 19, 20, 21 |
| 29 | | 169.1 | | | |
| 30 | 1.63, s | 20.8 | | | 29 |
| 31 | 3.11, s | 57.1 | | 20, 21 | 21 |

L. Synthesis of 17S,20S,21R-FD-895 (1j)

Figure 13A:
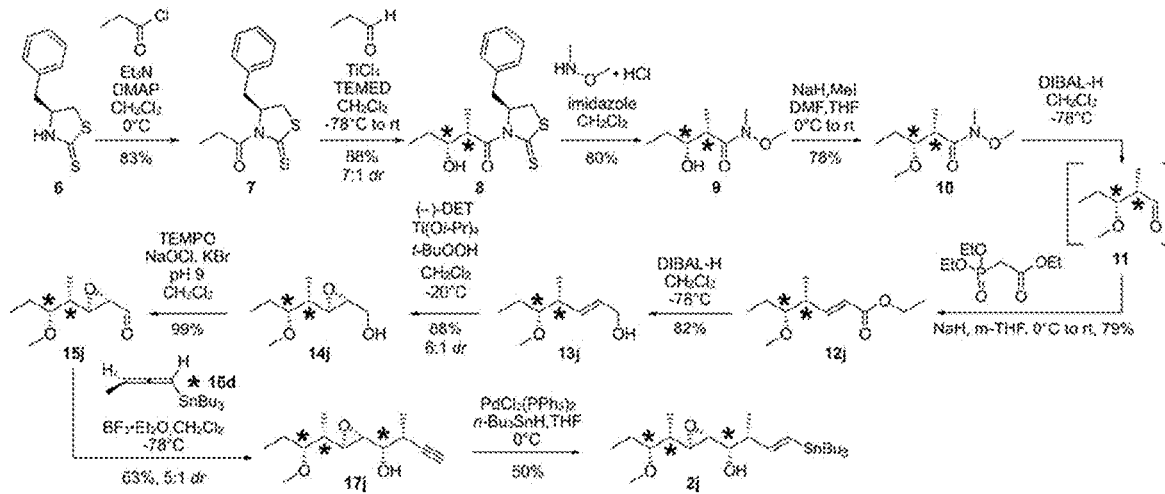
FIGS. 13A to 13C show synthetic scheme of compound 1j (17S, 20S, 21R-FD-895) in FIG. 2.
Figure 13B:
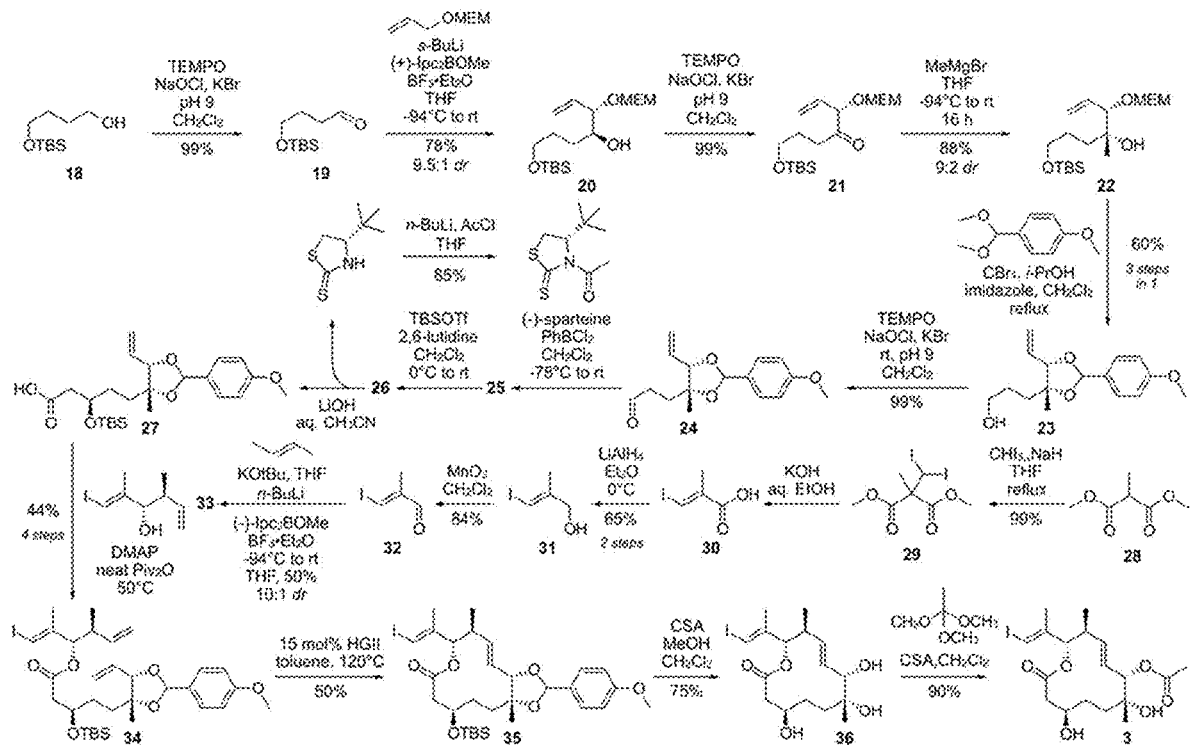
Figure 13C:
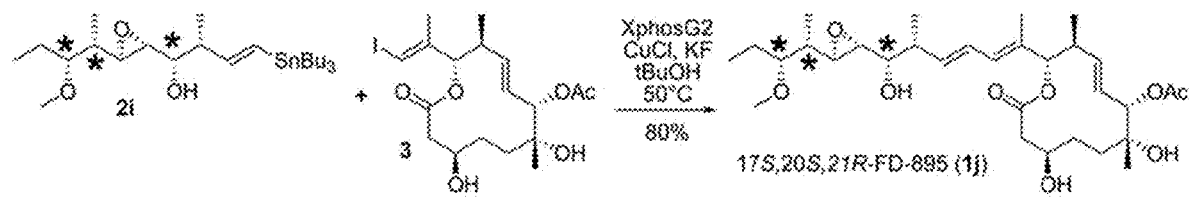

Total synthesis of 17S,20S,21R-FD-895 (1j) is shown in FIGS. 13A through 13C. For this study, 1j was prepared from compound 6 and 3 reported in Chan 2020. The side chain 2j was prepared from 6. Updated procedures are provided for this step. Asterisks (*) denote the compounds that differ from that used to prepare FD-895 (1).

Synthesis of Adduct 8j

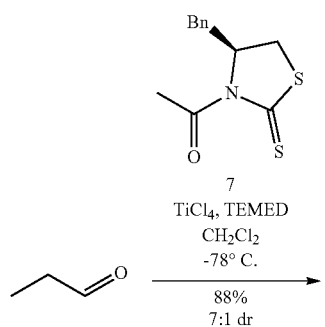

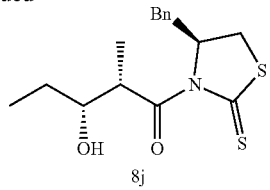

8j

Reagents:
Propionaldehyde, 98% (Alfa Aesar): redistilled before use
EtN(i-Pr)₂, 97% (Fisher Scientific): redistilled before use
TiCl₄, 98% (Alfa Aesar): used without further purification
(2S,3R)-1-((S)-4-Benzyl-2-thioxothiazolidin-3-yl)-3-hydroxy-2-methylpentan-1-one (8j). (S)-1-(4-Benzyl-2-thioxothiazolidin-3-yl)propan-1-one (7) (23.5 g, 88.7 mmol) was added to a 2 L reaction flask and dissolved in CH₂Cl₂ (700 mL) with mechanical stirring. The mixture was cooled below 0° C. TiCl₄ (10.1 mL, 92.2 mmol) was added dropwise over 1 h, while maintaining the temperature below 0° C., at which point the mixture turned orange. EtN(i-Pr)₂ (13.9 mL, 92.2 mmol) was added dropwise over 30 min, at which point the resulting black mixture was stirred at 0° C. for 15 min. After cooling the reaction to −94° C., a solution of propionaldehyde (7.10 mL, 98.4 mmol) in anhydrous CH₂Cl₂ (50 mL) was added dropwise over 1 h. The mixture was stirred at −94° C. for 30 min before being slowly warmed to rt overnight. The mixture was cooled to 0° C. and satd. NaHCO$_3$ (200 mL) was slowly added. The phases were separated, and the aqueous phase was extracted with CH$_2$Cl$_2$ (3×300 mL). The combined organic phases were washed with brine (300 mL), dried over Na$_2$SO$_4$, filtered and concentrated on a rotary evaporator. Pure adduct 8j (25.0 g, 88%) was obtained in a 9.5:1 dr by flash chromatography, eluting with a gradient of hexanes to 1:3 EtOAc/hexanes.

Adduct 8j: TLC (1:3 EtOAc/heptane): R$_f$=0.63 (CAM stain); $^1$H-NMR (500 MHz, CDCl$_3$) δ 7.35 (m, 2H), 7.30 (m, 3H), 5.36 (ddd, J=4.0, 7.0, 10.5 Hz, 1H), 4.52 (dq, J=3.0, 7.0 Hz, 1H), 3.86 (m, 1H), 3.41 (dd, J=7.0, 11.5 Hz, 1H), 3.24 (dd, J=4.0, 13.5 Hz, 1H), 3.06 (dd, J=10.5, 13.5 Hz, 1H), 2.91 (d, J=11.5 Hz, 1H), 2.64 (d, J=3.0 Hz, 1H), 1.57 (m, 1H), 1.45 (m, 1H), 1.25 (d, J=7.0 Hz, 3H), 0.97 (t, J=7.5 Hz, 3H). $^{13}$C-NMR (125 MHz, CDCl$_3$) δ 201.6, 178.7, 136.6, 129.7, 129.2, 127.5, 73.9, 69.1, 43.1, 37.0, 32.3, 27.5, 10.6, 10.5. FTIR (film) ν$_{max}$ 3444, 3027, 2964, 2937, 2876, 1689, 1455, 1352, 1258, 1191, 1164, 1041, 1029, 960 cm$^{-1}$; LCMS (ES-API) m/z calcd. for C$_{15}$H$_{19}$NO$_2$S$_2$ [M+1]$^+$: 324.40; [α]$^{25}_D$=36.2° (c=1.0 CH$_2$Cl$_2$).

Synthesis of Weinreb's Amide 9j

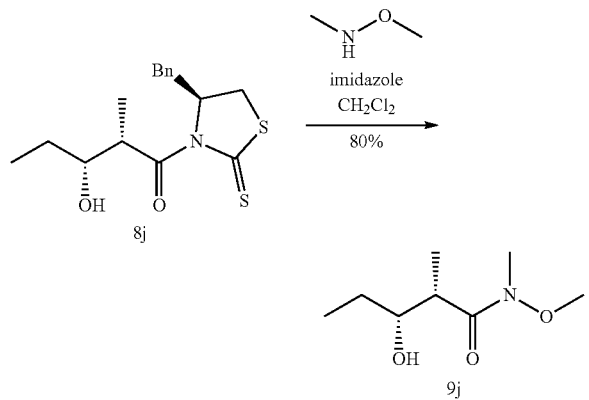

Reagents:
N,O-Dimethylhydroxylamine hydrochloride, 99% (Alfa Aesar): used without further purification
Imidazole, 99% (Sigma-Aldrich): used without further purification
(2S,3R)-3-Hydroxy-N-methoxy-N,2-dimethylpentanamide (9j). N,O-Dimethylhydroxylamine hydrochloride (8.70 g, 44.5 mmol) and imidazole (9.1 g, 134 mmol) were added in succession to a solution of 8j (14.4 g, 44.5 mmol) in CH$_2$Cl$_2$ (500 mL) in a 2 L reaction vessel at rt. The mixture was stirred at rt for an additional 16 h. H$_2$O (300 mL) was added, and the mixture was separated followed by extraction of the aqueous phase with CH$_2$Cl$_2$ (3×500 mL). The combined organic phases were washed with brine (500 mL), dried over Na$_2$SO$_4$, filtered and concentrated on a rotary evaporator to afford a yellow oil. Pure amide 9j (6.60 g, 80%) was obtained by flash chromatography, eluting with a gradient of hexanes to 3:1 EtOAc/hexanes.

Amide 9j: TLC (3:1 EtOAc/heptane): R$_f$=0.17 (KMnO$_4$); $^1$H NMR (500 MHz, CDCl$_3$) δ 3.79 (bs, 1H), 3.76 (td, J=5.4, 2.6 Hz, 1H), 3.69 (s, 3H), 3.17 (s, 3H), 2.90 (bs, 1H), 1.77 (bs, 1H), 1.57 (m, 1H), 1.39 (m, 1H), 1.15 (d, J=7.1 Hz, 3H), 0.95 (t, J=7.4 Hz, 3H); $^{13}$C NMR (125 MHz, CDCl$_3$) δ 178.5, 73.1, 61.7, 38.1, 32.0, 26.8, 10.5, 10.1; FTIR (film) ν$_{max}$ 2969, 2917, 2855, 1719, 1449, 1265, 1178, 1108, 1020, 715 cm$^{-1}$; LCMS (ES-API) m/z calcd. for C$_8$H$_{17}$NO$_3$[M+1]$^+$: 176.40; [α]$^{25}_D$=+7.3° (c=1.0, CH$_2$Cl$_2$).

Methylation of Amide 9j to 10j

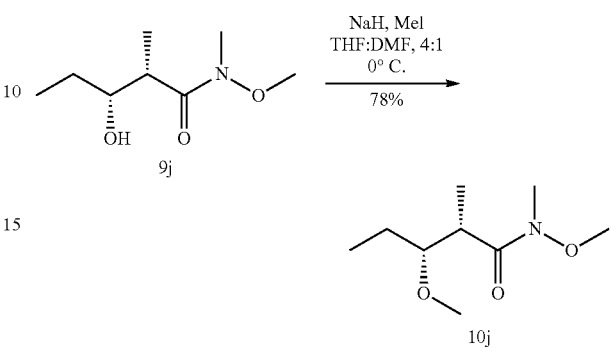

Reagents:
NaH, 60% in mineral oil (Alfa Aesar): used without further purification
MeI, 98% (Sigma-Aldrich): used without further purification
(2S,3R)—N,3-Dimethoxy-N,2-dimethylpentanamide (10j). MeI (35.8 mL, 576 mmol) was added at rt to a solution of amide 9j (5.00 g, 28.4 mmol) in a mixture of anhydrous THF (200 mL) and anhydrous DMF (50 mL) in a 1 L reaction vessel. The mixture was cooled to 0° C. and NaH (60% in mineral oil, 2.83 mg, 70.7 mmol) was added in portions ensuring the mixture remained at 0° C. The mixture was slowly warmed to rt and stirred for 16 h. After cooling the mixture to 0° C., a solution of phosphate buffered saline pH 7 (200 mL) was added dropwise. The volatiles were concentrated on a rotary evaporator. H$_2$O (100 mL) was added to the residue, and the obtained mixture was extracted with t-butyl methyl ether (3×300 mL). The combined organic phases were washed with brine (300 mL), dried over Na$_2$SO$_4$, filtered and concentrated on a rotary evaporator. Pure amide 10j (4.13 g, 77%) was obtained as a colorless oil by flash chromatography, eluting with a gradient of hexanes to 1:1 EtOAc/hexanes.

Amide 10j: TLC (3:1 EtOAc/heptane): R$_f$=0.27 (KMnO$_4$); $^1$H NMR (500 MHz, CDCl$_3$) δ 3.68 (s, 3H), 3.41 (s, 3H), 3.30 (tdd, J=7.0, 4.0, 1.0 Hz, 1H), 3.18 (s, 3H), 3.03 (bs, 1H), 1.58 (dqd, J=14.9, 7.5, 3.9 Hz, 1H), 1.42 (dt, J=14.4, 7.2 Hz, 1H), 1.21 (d, J=6.9 Hz, 3H), 0.93 (t, J=7.4 Hz, 3H); $^{13}$C NMR (125 MHz, CDCl$_3$) δ 176.5, 83.9, 61.6, 58.7, 39.6, 32.2, 25.3, 14.5, 9.6; FTIR (film) ν$_{max}$ 3581, 3502, 2969, 2934, 2882, 2820, 1658, 1457, 1379 cm$^{-1}$; LCMS (ES-API) m/z calcd. for C$_9$H$_{19}$NO$_3$ [M+1]$^+$: 190.40; [α]$^{25}$D=+16.1° (c=1.0 CHCl$_3$).

Conversion of 10 to Ester 12

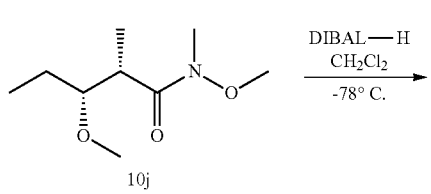

Reduction of ester 12j to alcohol 13j

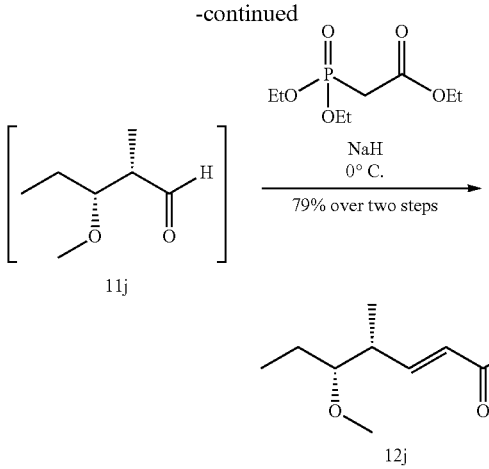

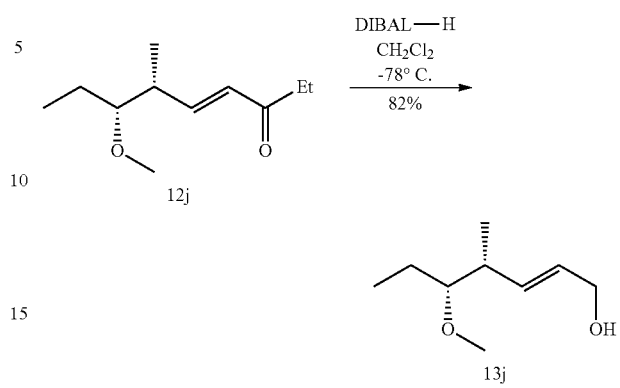

Reagents:

DIBAL-H, 1.0 M in hexanes (Sigma-Aldrich): used without further purification

NaH, 60% in mineral oil, (Alfa Aesar): used without further purification

Triethyl phosphonoacetate, 99% (Oakwood Chemical): used without further purification Ethyl (4R,5R,E)-5-methoxy-4-methylhept-2-enoate (12j) Amide 10j (4.00 g, 21.1 mmol) was dissolved in anhydrous $CH_2Cl_2$ (100 mL) in a 500 mL flask. The mixture was cooled to −78° C. DIBAL-H (1.0 M, 32.8 mL, 32.8 mol) was added dropwise over 45 min at −78° C. and stirred for 1 hr. Acetone (10 mL) was added dropwise over 10 min, and the mixture was warmed to 0° C. Satd. Rochelle's salt (100 mL) was added over 30 min, and the mixture was stirred at rt for 1.5 h. The phases were separated, and the aqueous phase was extracted with $CH_2Cl_2$ (3×150 mL). The combined organic phases were dried over $Na_2SO_4$, filtered and concentrated on a rotary evaporator. The residue was then dried via azeotropic removal of toluene to deliver aldehyde 11j, which was used immediately after preparation. A solution of triethyl phosphonoacetate (21.2 mL, 107 mmol) in anhydrous 2-methyltetrahydrofuran (40 mL) was added dropwise over 30 min to a 500 mL reaction flask containing a suspension of NaH (60% in mineral oil, 3.6 g, 90.3 mol) in anhydrous 2-methyltetrahydrofuran (150 mL) cooled to 0° C. The mixture was stirred at 0° C. for 15 min and a solution of 11j in anhydrous 2-methyltetrahydrofuran (100 mL) was added dropwise over 30 min. The mixture was stirred at rt for 16 h, cooled to 0° C. and quenched with satd. $NH_4Cl$ (250 mL). The organics were concentrated on a rotary evaporator. The mixture was extracted with EtOAc (2×300 mL), and the combined organic phases were dried over $Na_2SO_4$, filtered and concentrated on a rotary evaporator. Pure ester 12j (3.27 g, 78% over two steps) was obtained as a colorless oil by flash chromatography, eluting with a gradient of $CH_2Cl_2$ to 1:10 EtOAc/$CH_2Cl_2$.

Ester 12j: TLC ($CH_2Cl_2$): $R_f$=0.14 (CAM stain); $^1H$ NMR (500 MHz, $CDCl_3$) δ 6.95 (dd, J=15.8, 7.7 Hz, 1H), 5.82 (dd, J=15.8, 1.3 Hz, 1H), 4.18 (q, J=7.1 Hz, 2H), 3.36 (s, 3H), 3.00 (ddd, J=7.4, 5.6, 4.4 Hz, 1H), 2.57 (m, 1H), 1.51 (m, 1H), 1.41 (m, 1H), 1.28 (t, J=7.1 Hz, 3H), 1.07 (d, J=6.8 Hz, 3H), 0.90 (t, J=7.4 Hz, 3H); $^{13}C$ NMR (125 MHz, $CDCl_3$) δ 166.8, 151.3, 121.1, 85.6, 60.4, 58.0, 39.3, 20.0, 14.9, 14.4, 10.0; FTIR (film) $v_{max}$ 2978, 2934, 2882, 2820, 1719, 1650, 1466 $cm^{-1}$; LCMS (ES-API) m/z calcd. for $C_{11}H_{20}O_3$ $[M+NH_4]^+$: 218.6; $[α]^{25}D$=+44.9° (c=1.0, $CH_2Cl_2$).

Reagents:

DIBAL-H, 1.0 M in hexanes (Sigma-Aldrich): used without further purification (4R,5R,E)-5-Methoxy-4-methylhept-2-en-1-ol (13j). DIBAL-H (1.0 M, 37.1 mL, 45.0 mmol) was added dropwise over 60 min to a 5 L reaction flask containing a solution of ester 12j (3.00 g, 14.9 mmol) in anhydrous $CH_2Cl_2$ (150 mL) cooled to −78° C. The mixture was stirred for 1 h at −78° C. Acetone (30 mL) was then added dropwise. The mixture was warmed to 0° C., satd. Rochelle's salt (50 mL) was added, and the mixture was stirred at rt for 2 h. The phases were separated, and the aqueous phase was extracted with $CH_2Cl_2$ (3×100 mL). The combined organic phases were washed with brine (100 mL), dried over $Na_2SO_4$, filtered and concentrated on a rotary evaporator. Pure alcohol 13j (1.93 g, 82%) was obtained by flash chromatography, eluting with a gradient of heptane to 1:1 EtOAc/heptane.

Alcohol 13j: TLC (1:3 EtOAc/heptane): $R_f$=0.26 (CAM stain); $^1H$ NMR (500 MHz, $CDCl_3$) δ 5.65 (m, 2H), 4.10 (bs, 2H), 3.36 (s, 3H), 2.92 (ddd, J=7.5, 5.7, 4.2 Hz, 1H), 2.44 (m, 1H), 1.52 (m, 1H), 1.40 (m, 1H), 1.01 (d, J=6.9 Hz, 3H), 0.90 (t, J=7.4 Hz, 3H); $^{13}C$ NMR (125 MHz, $CDCl_3$) δ 135.2, 129.0, 86.4, 64.0, 57.7, 38.9, 23.5, 16.0, 10.0; FTIR (film) $v_{max}$ 3388, 2968, 2932, 2876, 2826, 1460, 1375 $cm^{-1}$; LCMS (ES-API) m/z calcd. for $C_9H_{18}O_2$ $[M+1]^+$: 158.20; $[α]^{25}_D$=−33.1° (c=0.2, $CHCl_3$).

Epoxidation of Alcohol 13j

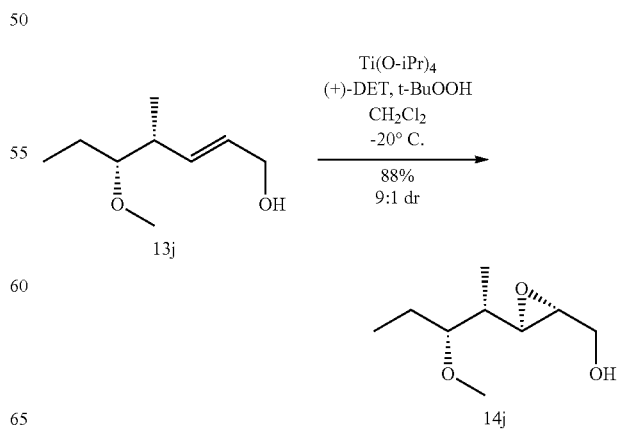

Reagents:

Ti(Oi-Pr)$_4$, 97% (Sigma-Aldrich): vacuum distilled at 90° C., 5 mbar (+)-Diethyltartrate, 99% (Alfa Aesar): used without further purification t-Butylhydroperoxide, 3.3 M in toluene: dried from a 70% solution in water according to methods developed by the Sharpless laboratory ((2S,3S)-3-((2R,3S)-3-Methoxypentan-2-yl)oxiran-2-yl)methanol (14j). t-Butylhydroperoxide (3.3 M, 4.80 mL, 16.3 mmol) was added to a 100 mL flask containing a stirring solution of Ti(Oi-Pr)$_4$ (0.163 mL, 0.788 mmol), (+)-diethyl tartrate (0.550 mL, 3.15 mmol) and powdered 4A molecular sieves (1 g) in anhydrous CH$_2$Cl$_2$ (100 mL). The mixture was cooled to −20° C. and stirred for 30 min. A solution of alcohol 13j (1.25 g, 7.98 mmol) in CH$_2$Cl$_2$ (25 mL) was added dropwise. The reaction was stirred at −20° C. for 4 h. The reaction was quenched via addition of 10% NaOH (10 mL). The mixture was then extracted into CH$_2$Cl$_2$ and concentrated on a rotary evaporator. Pure epoxyalcohol 14j (1.38 g, 88%) was obtained as a 6:1 mixture of diastereomers by flash chromatography, eluting with a gradient of hexanes to 1:1 EtOAc/hexanes.

Oxidation of Epoxyalcohol 14j

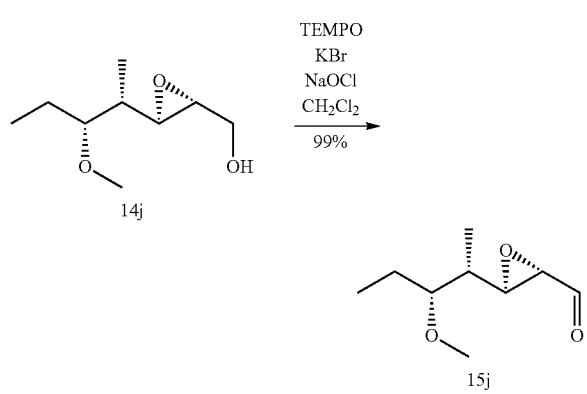

Reagents:

TEMPO, 99% (Oakwood Chemical): used without further purification

KBr, (Spectrum Chemical Mfg. Corp.): used without further purification

NaOCl, 2 M, 10-15% active chlorine (Spectrum Chemical Mfg. Corp.): used without further purification (2S,3R)-3-((2R,3S)-3-Methoxypentan-2-yl)oxirane-2-carbaldehyde (15j). A solution of KBr (60.5 mg, 0.51 mmol) in H$_2$O (3 mL), satd. NaHCO$_3$ (5 mL) and TEMPO (66.5 mg, 0.425 mmol) were added sequentially to a 125 mL flask containing a solution of epoxyalcohol 14j (1.11 g, 6.35 mmol) in CH$_2$Cl$_2$ (50 mL). The mixture was cooled to 0° C. and a solution of NaOCl (2 M, 4.25 mL, 8.50 mmol) and satd. NaHCO$_3$ (5 mL) were added dropwise via an addition funnel. The mixture was allowed to warm to rt and stirred for 2 h. The phases were separated, and the aqueous phase was extracted with CH$_2$Cl$_2$ (3×50 mL). The combined organic phases were washed with brine (30 mL), dried over Na$_2$SO$_4$, filtered and concentrated on a rotary evaporator. Aldehyde 15j (1.10 g, 99%) was obtained without further purification and was carried on directly to the next step.

Marshall Addition of Epoxyaldehyde 15j

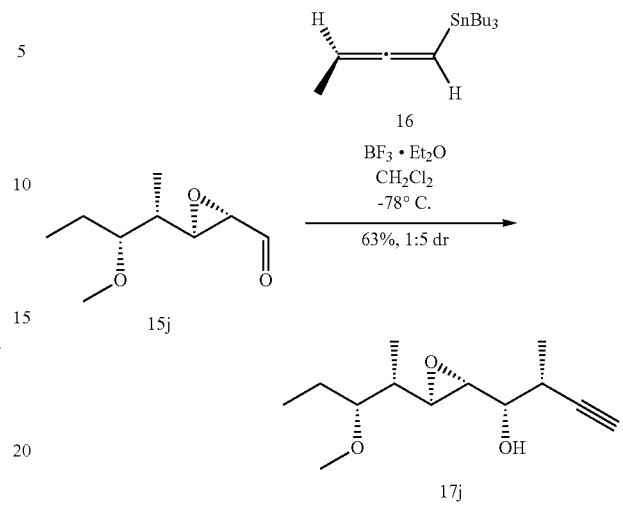

Reagents:

BF$_3$·Et$_2$O, 46.5% BF$_3$ (Alfa Aesar): used without further purification (1R,2R)-1-((2S,3S)-3-((2S,3R)-3-methoxypentan-2-yl)oxiran-2-yl)-2-methylbut-3-yn-1-ol (17j). Aldehyde 15j (70.1 mg, 0.408 mmol) and allenylstannane 16 (0.210 g, 0.610 mmol) in a 50 mL flask were dissolved in anhydrous CH$_2$Cl$_2$ (10.0 mL) and purged with an Ar atmosphere. The mixture was cooled to −78° C. and BF$_3$·Et$_2$O (75.3 µL, 0.610 mmol) was added dropwise over 5 min. The reaction was stirred for 1 h at −78° C. A mixture of MeOH (5 mL) and satd. NaHCO$_3$ (1 mL) was added, and the solution was warmed to rt. The phases were separated, and the aqueous phases were extracted with Et$_2$O (3×50 mL). The organic phases were combined, dried with Na$_2$SO$_4$ and concentrated on a rotary evaporator. Alkyne 17j (69.2 mg, 63%) was obtained in a 5:1 mixture of diastereomers (by NMR) as a colorless oil by flash chromatography, eluting with a gradient of hexanes to 1:3 Et$_2$O/hexanes.

Hydrostannylation of Alkyne 17i

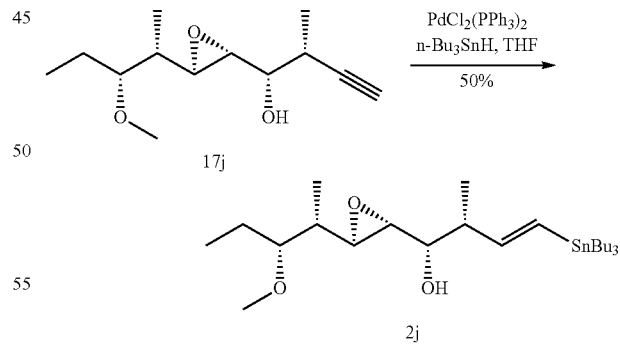

Reagents:

n-Bu$_3$SnH, 97% contains 0.05% BHT as stabilizer (Acros Organics): used without further purification PdCl$_2$(PPh$_3$)$_2$ (Oakwood Chemical): dried via azeotropic distillation of benzene (1R,2R,E)-1-((2R,3R)-3-((2R,3S)-3-Methoxypentan-2-yl)oxiran-2-yl)-2-methyl-4-(tributylstannyl)but-3-en-1-ol (2). PdCl$_2$(PPh$_3$)$_2$ (15.5 mg, 0.0221 mmol) was added to a solution of alkyne 17j (50.1 mg, 0.221 mmol) in a 10 mL flask in anhydrous THF (5 mL). The mixture was cooled to 0° C. and n-Bu₃SnH (0.179 mL, 0.663 mmol) was added dropwise. The mixture was stirred for 45 min at 0° C., at which point the resulting mixture was concentrated to yield a black crude oil. The material was extracted into hexanes, filtered through a pad of Celite and was eluted with hexanes. The eluant was concentrated on a rotary evaporator, and this process was repeated twice until a clear black solution was achieved. Pure vinylstannane 2j (22.0 mg, 50%) was obtained as a mixture of 1:5 α:β regioisomers by flash chromatography, eluting with a gradient of hexanes to $CH_2Cl_2$ to 1:20 $Et_2O/CH_2Cl_2$. The desired regioisomer and diastereomer can be obtained in 95+% purity by additional flash chromatography, eluting with a gradient of hexanes to $CH_2Cl_2$ to 1:20 $Et_2O/CH_2Cl_2$.

Stille Coupling of Vinylstannane 2j and Core 3 to Afford 17S,18S,19S-FD-895 (1i).

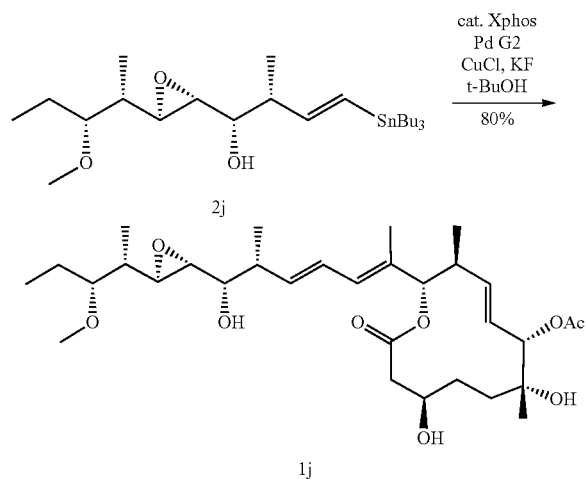

Reagents:
CuCl, anhydrous, beads, 99.99% (Sigma-Aldrich): beads were powdered prior to addition
KF, anhydrous, powder, 99.9% (Sigma-Aldrich): used without further purification
XPhos Pd G2 (Sigma-Aldrich): used without further purification
t-BuOH, anhydrous, 99.5% (Sigma-Aldrich): used without further purification Vinylstannane 2-2j (1.5 eq) and core 3-3f (1 eq) were combined in a 50 mL flask and dried via rotary evaporation of benzene. To the mixture was then sequentially added CuCl (1.5 eq), KF (1.5 eq) and XPhos Pd G2 (0.05 eq) and anhydrous t-BuOH (10 mL). The reaction vessel was purged under Ar, heated to 50° C. and stirred overnight, at which point solution turns into a gray cloudy mixture. The mixture was then filtered through a plug of Celite and eluted with acetone (20 mL). The elutants were concentrated on a rotary evaporator to yield a crude brown semi-solid. Pure 1-1j was obtained as a white semi-solid by flash chromatography over neutral silica gel, eluting with a gradient of hexanes to 1:3 acetone/hexanes.

17S,18S,19S-FD-895 (1i): Yield: 80%, 3.45 mg; TLC (1:3 acetone/$CH_2Cl_2$): $R_f$=0.28 (CAM stain); NMR data provided in Table S11; FTIR (film) $v_{max}$ 3447, 2963, 2930, 2875, 1739, 1457, 1374, 1239, 1176, 1089, 1021 $cm^{-1}$; HR-ESI-MS m/z calcd. for $C_{31}H_{50}IO_9Na$ [M+Na]⁺: 589.3345, found 589.3347; $[α]^{25}D$=−2.3° (c=1.0, $CH_2Cl_2$).

TABLE 11

| NMR data for 17S,20S,21S-FD-895 (1j) in $C_6D_6$ | | | | | |
|---|---|---|---|---|---|
| Position | $δ_H$, mult (J in Hz) | $δ_C$ | ¹H, ¹H-COSY | ¹H, ¹H-NOSEY | ¹H, ¹³C-HMBC |
| 1 | | 172.1 | | | |
| 2' | 2.29, dd (14.8, 3.8) | 38.2 | 3 | 3w | 1, 3, 4 |
| 2" | 2.19, dd (14.8, 2.9) | | 3 | 3, 4'/5' | 1 |
| 3 | 3.50, m | 69.0 | 3OH, 4" | 2', 4'/5', 5" | |
| 3-OH | 3.62, bs | | 3w, 4" | 3 | |
| 4' | 1.56, m | 30.0 | 3, 4", 5' | 2", 8w, 24 | 3w, 6, 24w |
| 4" | 1.25, m | | 3, 4', 5" | 5', 7, 9, 24w | 5 |
| 5' | 1.54, m | 35.6 | 4', 4", 5" | 2", 4", 8w | 3w, 4, 6, 24w |
| 5" | 1.20, m | | 4', 4", 5' | 3, 4', 7, 24w | 4, 6w, 7w |
| 6 | | 73.4 | | | |
| 6-OH | | | | | |
| 7 | 5.24, d (6.6) | 78.9 | 8 | 4', 4", 8w, 9, 24 | 8, 9, 24w, 29 |
| 8 | 5.82, dd (15.2, 12.3) | 126.2 | 7, 9 | 4'/5', 7w, 9, 10 | 6w, 10 |
| 9 | 5.62, dd (15.2, 10.0) | 140.5 | 8, 10 | 4", 8, 10, 11, 25 | 7, 10w, 25 |
| 10 | 2.38, m | 41.0 | 9, 11, 25 | 8, 25, 26 | 11w, 25 |
| 11 | 5.26, d (7.5) | 82.4 | 10 | 9, 10, 13, 25 | 1, 12, 26 |
| 12 | | 131.4 | | | |
| 13 | 6.17, d (10.8) | 131.4 | 14, 26 | 10w, 11, 14, 15, 25 | 11, 14, 15, 26 |
| 14 | 6.32 dd (15.2, 10.8) | 126.2 | 13, 15 | 13, 15, 16, 26, 27 | 13, 16 |
| 15 | 5.83, dd (15.2, 10.4) | 137.9 | 14, 16 | 13, 14, 16, 17w, | 13, 16, 27w |
| 16 | 2.44, tq (6.6, 6.3) | 41.4 | 15, 17, 27 | 17w, 27 | 14, 15, 17, 18w, |
| 17 | 3.36, t (4.9) | 73.4 | 16, 18 | 15w, 16, 18, 19, 27 | 15w, 18 |
| 17-OH | | | | | |
| 18 | 2.74, dd (4.5, 2.3) | 58.6 | 17, 19 | 16, 17, 20, 27, 28 | 17 |
| 19 | 2.95, dd (7.0, 2.3) | 57.4 | 18, 20 | 17, 20, 28 | 20 |
| 20 | 1.55, m | 37.8 | 19, 21, 28 | 18, 21, 28 | 19 |

TABLE 11-continued

NMR data for 17S,20S,21S-FD-895 (1j) in C$_6$D$_6$

| Position | $\delta_H$, mult (J in Hz) | $\delta_C$ | $^1$H, $^1$H-COSY | $^1$H, $^1$H-NOSEY | $^1$H, $^{13}$C-HMBC |
|---|---|---|---|---|---|
| 21 | 2.84, dt (7.4, 4.7) | 84.4 | 20, 22', 22" | 20, 22', 22", 23, | 19 |
| 22' | 1.52, m | 23.4 | 20, 21, 23 | 23w | 23 |
| 22" | 1.38, m | | 20, 21, 23 | 20, 21w, 28 | 23 |
| 23 | 0.85, t (7.4) | 10.2 | 22', 22" | 21w, 22', 22" | 21, 22 |
| 24 | 1.00, s | 24.5 | | 4'/5', 7 | 5, 6, 7 |
| 25 | 0.70, d (6.7) | 16.2 | 10 | 9, 10, 11, 13w | 9, 10, 11 |
| 26 | 1.58, d (1.2) | 11.6 | 13 | 10, 11, 14, 15, 25 | 11, 12, 13 |
| 27 | 1.14, d (6.9) | 16.3 | 16 | 14, 15, 16, 17, 18w | 15, 16, 17 |
| 28 | 1.02, d (7.5) | 12.0 | 20 | 18w, 20, 21w | 19, 20, 21 |
| 29 | | 169.0 | | | |
| 30 | 1.61, s | 20.4 | | | 29 |
| 31 | 3.11, s | 56.9 | | 20w, 21 | 21 |

Example 4: Biological Assays

Cell Culture.

HCT-116 cells was cultured in McCoy's 5a (Life Technologies) supplemented with 10% fetal bovine serum (FBS), 2 mM L-glutamine, and 100 U mL$^{-1}$ of penicillin and 100 µg mL$^{-1}$ of streptomycin at 37° C. in an atmosphere of 5% CO$_2$. Compounds were dissolved in DMSO (MilliporeSigma). Cells were treated with 1-1j in media with ≥0.5% DMSO for 4-72 h.

Cell Viability Assays.

Studies were conducted in 8 welled cell culture plates. HCT-116 plated at 5×10$^3$ cells/well were cultured for 24 h and then treated with analogs 1-1j for 4-72 h, then washed twice with 100 µL PBS. PBS (100 µL) was added to each well, followed by 20 µL of CellTiter Aqueous One Solution (Promega). After 2 h at 37° C., absorbance readings were taken at 490 nm (test wavelength) and 690 nm (reference wavelength). GI$_{50}$ values were calculated in Prism (GraphPad) using greater 3 replicates.

Quantitative Real Time PCR (qPCR) Analyses.

Cells were treated with 1 or 1a-1j in media (McCoy's 5a (Life Technologies) supplemented with 10% FBS, 2 mM L-glutamine, and 100 U mL$^{-1}$ of penicillin and 100 µg mL$^{-1}$ of streptomycin 0.5% DMSO) for 4 h or 24 h. Untreated cells were considered were used as negative control. Total RNA was isolated using mirVana miRNA isolation kit (Life Technologies). A 1 µg sample of RNA was subjected to DNAseI from a TURBO DNA free kit (Life Technologies). The cDNA was prepared by using SuperScript III reverse transcriptase kit (Life Technologies). The amount of unspliced RNA for different genes was determined using Power SYBR Green PCR master mix (Applied Biosystems) by qPCR using specific primers for each gene. qPCR using 2.5 µM of each primer was performed on 5 ng of the obtained cDNA. qPCR conditions were as follows: 95° C. for 10 min for one cycle, then 95° C. for 10 min for one cycle, then 95° C. for 30 s, 55° C. for 60 s, 72° C. for 60 s, for 40 cycles using the MXPro. Quantification cycle (Cq) values were identified for each sample, and then RNA levels were calculated using 2-ΔΔCT method. GAPDH was used as a control for normalization. At least three replicates were conducted for each compound. Namely, all genes explored in this study were evaluated from the same cell cultures. Here, individual cultures were used for each compound explored and at least three replicates were used for each compound. While experimental variation occurred between the different compound treatments, the levels of the different intron retention, exon skipping or RNA expression were collected from the same cellular material. Statistics were calculated using a standard one-way ANOVA; p values were represented so that * signifies p<0.0001. HCT116 were treated with analogs 1-1j ranging from 0.1-5000 nM for 72 hours, then cell viability was measured using the MTS assay. GI$_{50}$ values and confidence intervals were calculated using GraphPad (Table 12).

TABLE 12

GI$_{50}$ values for analogs 1-1j.

| Analog | GI$_{50}$ value (nM) | 95% confidence interval |
|---|---|---|
| FD-895 (1) | 1.72 | 1.004 to 2.828 |
| C3 FD-895 (1a) | 2.21 | 1.148 to 4.044 |
| C7 FD-895 (1b) | 431.8 | 176.9 to 999.4 |
| C10,11 FD-895 (1c) | 36553 | 26507 to 56115 |
| 17S-FD-895 (1d) | 2.06 | 1.466 to 2.858 |
| 17-methoxy FD-895 (1e) | 2.21 | 1.110 to 4.175 |
| 17-methoxy 17S-FD-895 (1f) | 37.65 | 25.77 to 55.17 |
| C3 17S-FD-895 (1g) | 131.2 | 88.69 to 199.0 |
| C7 17S-FD-895 (1h) | 806.2 | 553.9 to 1163 |
| C18,19 17S-FD-895 (1i) | 445.5 | 319.8 to 620.6 |
| C20,21 17S-FD-895 (1j) | 262.2 | 178.6 to 391.8 |

What is claimed is:

1. A compound selected from:

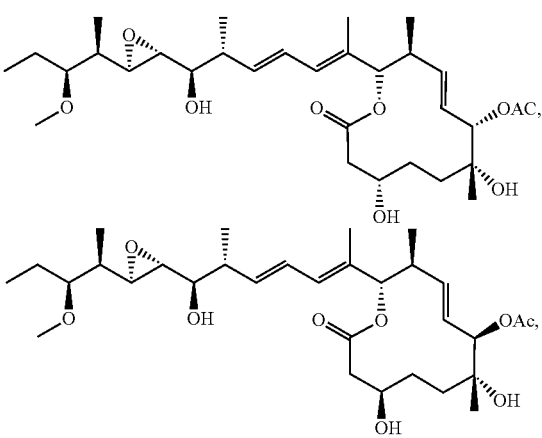

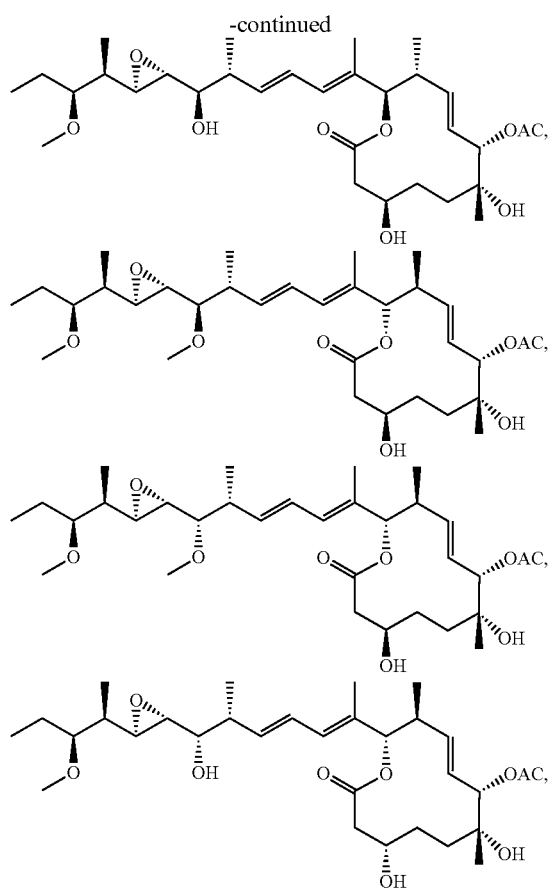

or a pharmaceutically acceptable salt thereof.

2. A pharmaceutical composition comprising the compound of claim 1 and a pharmaceutically acceptable excipient.

3. A method of treating cancer, the method comprising administering to a subject in need thereof a therapeutically effective amount of the compound of claim 1, wherein the cancer is colon cancer.

4. A compound having the formula:

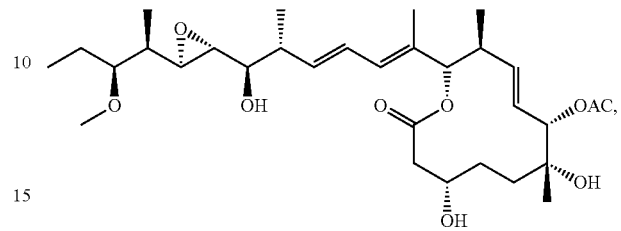

or a pharmaceutically acceptable salt thereof.

5. A compound having the formula:

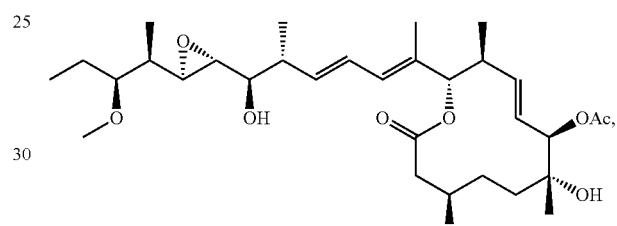

or a pharmaceutically acceptable salt thereof.

6. A compound having the formula:

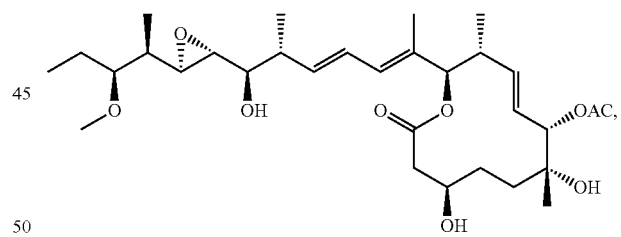

or a pharmaceutically acceptable salt thereof.

7. A compound having the formula:

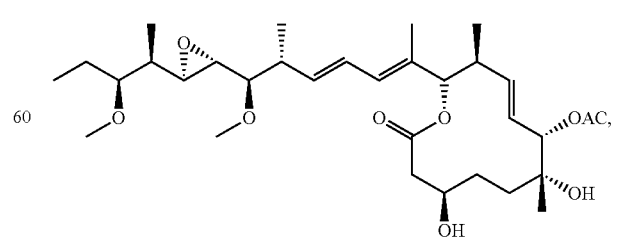

or a pharmaceutically acceptable salt thereof.

8. A compound having the formula:

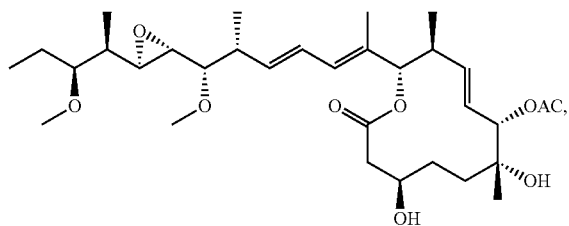

or a pharmaceutically acceptable salt thereof.

9. A compound having the formula:

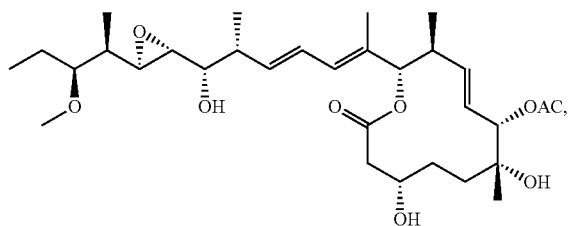

or a pharmaceutically acceptable salt thereof.

10. A compound having the formula:

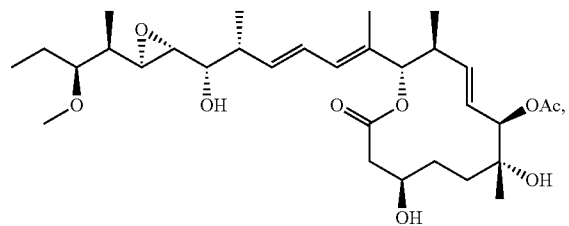 [SMILES: CC[C@H](OC)[C@@H](C)[C@H]1O[C@@H]1[C@@H](O)[C@H](C)/C=C/C=C(\C)[C@H]1OC(=O)C[C@H](O)CC[C@@](C)(O)[C@H](OC(C)=O)/C=C/[C@@H]1C]

or a pharmaceutically acceptable salt thereof.

11. A compound having the formula:

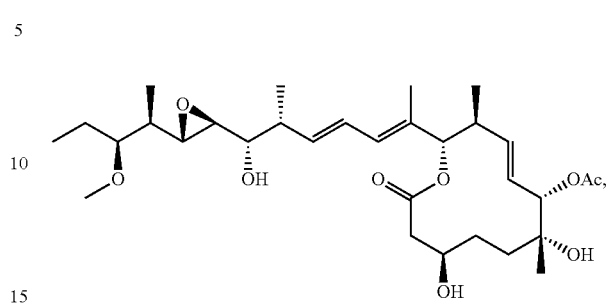

or a pharmaceutically acceptable salt thereof.

12. A compound having the formula:

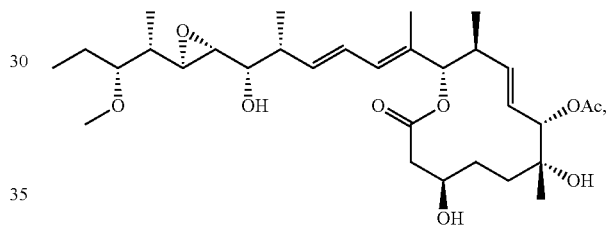

or a pharmaceutically acceptable salt thereof.

* * * * *